(12) United States Patent
Taslim et al.

(10) Patent No.: US 10,782,285 B2
(45) Date of Patent: Sep. 22, 2020

(54) DEVICE AND METHOD FOR CHEMICAL ANALYSIS

(71) Applicants: Rite Taste, LLC, Weston, MA (US); Namal Nawana, Weston, MA (US)

(72) Inventors: Mohammad E. Taslim, Needham, MA (US); Mohammed Fotouhi, Weston, MA (US); Mehdi Abedi, Brighton, MA (US); Reza Mollaaghababa, Natick, MA (US); Bahram Fotouhi, Cupertino, CA (US); Kashayar Javaherian, Lexington, MA (US); Edward Alvin Greenfield, Stoughton, MA (US); Namal Nawana, Weston, MA (US)

(73) Assignee: Rite Taste, LLC, Weston, MA (US)

( * ) Notice: Subject to any disclaimer, the term of this patent is extended or adjusted under 35 U.S.C. 154(b) by 0 days.

(21) Appl. No.: 16/422,770

(22) Filed: May 24, 2019

(65) Prior Publication Data

US 2019/0317081 A1   Oct. 17, 2019

Related U.S. Application Data

(63) Continuation-in-part of application No. 15/357,445, filed on Nov. 21, 2016, now Pat. No. 10,401,352, (Continued)

(51) Int. Cl.
*G01N 33/53* (2006.01)
*G01N 33/544* (2006.01)
(Continued)

(52) U.S. Cl.
CPC ........ *G01N 33/5302* (2013.01); *B01L 3/5027* (2013.01); *G01N 1/286* (2013.01);
(Continued)

(58) Field of Classification Search
CPC .. G01N 33/5302; G01N 33/02; G01N 33/025; G01N 33/5308; G01N 33/54366;
(Continued)

(56) References Cited

U.S. PATENT DOCUMENTS

| 4,983,102 A | 1/1991 | Swain |
| 6,037,168 A | 3/2000 | Brown |
| (Continued) | | |

FOREIGN PATENT DOCUMENTS

| DE | 19600521 A1 | 7/1996 |
| WO | 2001/47704 A1 | 7/2001 |
| (Continued) | | |

OTHER PUBLICATIONS

Huang, Yinxi, et al. "Graphene-based biosensors for detection of bacteria and their metabolic activities." Journal of Materials Chemistry 21.33 (2011): 12358-12362.*

(Continued)

*Primary Examiner* — Robert J Eom
(74) *Attorney, Agent, or Firm* — Nutter McClennen & Fish LLP

(57) ABSTRACT

A processing and detection system for detecting presence of at least one gluten protein in a food sample comprises a food processor including: a reservoir containing a process liquid for processing the food sample; a body that comprises a chamber configured to receive the food sample; and a pressing surface configured to press on the reservoir to cause the process liquid to exit the reservoir and mix with the food sample, thereby generating a processed food liquid; and an exit port configured to conduct the processed food liquid out of the food processor; and a cartridge including: at least one sensor configured to receive the processed food liquid and to generate an electrical signal in response to interaction with the at least one gluten protein in the processed food liquid, (Continued)

and an analyzer in electrical communication with the at least one sensor for detecting the electrical signal and determining the presence of the at least one gluten protein in the food sample based on the detected electrical signal.

19 Claims, 69 Drawing Sheets

Related U.S. Application Data which is a continuation of application No. 14/874,228, filed on Oct. 2, 2015, now Pat. No. 9,664,674.

(60) Provisional application No. 62/059,731, filed on Oct. 3, 2014, provisional application No. 62/206,471, filed on Aug. 18, 2015, provisional application No. 62/676,079, filed on May 24, 2018.

(51) Int. Cl.
| | | |
|---|---|---|
| *G01N 33/02* | (2006.01) | |
| *G01N 27/04* | (2006.01) | |
| *G01N 33/552* | (2006.01) | |
| *B01L 3/00* | (2006.01) | |
| *G01N 33/543* | (2006.01) | |
| *G01N 33/551* | (2006.01) | |
| *G01N 33/68* | (2006.01) | |
| *G01N 1/40* | (2006.01) | |
| *G01N 1/28* | (2006.01) | |

(52) U.S. Cl.
CPC ......... *G01N 1/4044* (2013.01); *G01N 1/4077* (2013.01); *G01N 27/045* (2013.01); *G01N 33/02* (2013.01); *G01N 33/025* (2013.01); *G01N 33/5308* (2013.01); *G01N 33/544* (2013.01); *G01N 33/5438* (2013.01); *G01N 33/54366* (2013.01); *G01N 33/551* (2013.01); *G01N 33/552* (2013.01); *G01N 33/68* (2013.01); *B01L 2200/04* (2013.01); *B01L 2300/023* (2013.01); *B01L 2300/0663* (2013.01); *G01N 2001/2866* (2013.01); *G01N 2001/4088* (2013.01); *G01N 2333/415* (2013.01)

(58) Field of Classification Search
CPC ............. G01N 33/5438; G01N 33/544; G01N 33/551; G01N 33/552; G01N 33/68; G01N 1/4044; G01N 1/4077; G01N 27/045; B01L 3/5027
See application file for complete search history.

(56) References Cited

U.S. PATENT DOCUMENTS

| | | |
|---|---|---|
| 8,575,663 B2 | 11/2013 | Lieber et al. |
| 8,695,810 B2 | 4/2014 | Gao |
| 8,907,384 B2 | 12/2014 | Pace et al. |
| 9,146,209 B2 | 9/2015 | Johnson et al. |
| 9,160,024 B1 | 10/2015 | Moore et al. |
| 9,162,885 B2 | 10/2015 | Lee et al. |
| 9,612,240 B2 | 4/2017 | Johnson, Jr. et al. |
| 9,618,476 B2 | 4/2017 | Goldsmith |
| 9,664,674 B2 | 5/2017 | Taslim et al. |
| 9,735,366 B2 | 8/2017 | Turchanin |
| 9,765,395 B2 | 9/2017 | Goldsmith |
| 9,887,352 B2 | 2/2018 | Bessonov et al. |
| 10,168,297 B2 | 1/2019 | Johnson, Jr. et al. |
| 10,401,352 B2 | 9/2019 | Taslim et al. |
| 2004/0146863 A1 | 7/2004 | Pisharody et al. |
| 2005/0072213 A1 | 4/2005 | Besnard et al. |
| 2006/0188934 A1 | 8/2006 | Chang et al. |
| 2008/0017737 A1 | 1/2008 | So et al. |
| 2009/0092965 A1 | 4/2009 | Weiss et al. |
| 2009/0311727 A1 | 12/2009 | Watkins et al. |
| 2012/0129198 A1 | 5/2012 | Buechler et al. |
| 2012/0156688 A1 | 6/2012 | McAlpine et al. |
| 2012/0264232 A1 | 10/2012 | Kramer et al. |
| 2013/0164859 A1 | 6/2013 | Johnson et al. |
| 2013/0217598 A1 | 8/2013 | Ludwig et al. |
| 2014/0220617 A1 | 8/2014 | Yung et al. |
| 2014/0295406 A1 | 10/2014 | Sundvor et al. |
| 2015/0011020 A1 | 1/2015 | Sundvor et al. |
| 2015/0065363 A1 | 3/2015 | Johnson, Jr. et al. |
| 2015/0307936 A1 | 10/2015 | Goldsmith |
| 2015/0309018 A1 | 10/2015 | Goldsmith |
| 2015/0346141 A1 | 12/2015 | Johnson et al. |
| 2016/0025675 A1 | 1/2016 | Goldsmith |
| 2016/0054312 A1 | 2/2016 | Goldsmith |
| 2016/0097764 A1 | 4/2016 | Taslim et al. |
| 2016/0223538 A1 | 8/2016 | McAlpine et al. |
| 2017/0067888 A1 | 3/2017 | Taslim et al. |
| 2017/0299602 A1 | 10/2017 | Johnson, Jr. et al. |
| 2017/0307562 A1 | 10/2017 | Goldsmith |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0037952 A1 | 2/2018 | Goldsmith |
| 2019/0079068 A1 | 3/2019 | Taslim et al. |
| 2019/0187090 A1* | 6/2019 | Grabbert ................ G01N 27/00 |
| 2019/0284615 A1 | 9/2019 | Fotouhi et al. |
| 2020/0011860 A1 | 1/2020 | Nawana et al. |

FOREIGN PATENT DOCUMENTS

| | | | |
|---|---|---|---|
| WO | 2014/160861 A1 | 10/2014 | |
| WO | 2017/103269 A1 | 6/2017 | |
| WO | WO-2017194746 A1 * | 11/2017 | ......... G01N 27/4146 |

OTHER PUBLICATIONS

Agilent Technologies International sarl, Agilent B1500A Semiconductor Device Analyzer User's Guide, Edition 6, Nov. 2007, p. 1-588.*

Neves, Marta MPS, et al. "Voltannnnetric innnnunosensor for the diagnosis of celiac disease based on the quantification of anti-gliadin antibodies." Sensors and Actuators B: Chemical 163.1 (2012): 253-259.*

Vasilescu, Alina, Alis Vezeanu, and Mihaela Badea. "Electrochemical impedance spectroscopy investigations focused on food allergens." Sensing in Electroanalysis.(K. Kalcher, R. Metelka, I. Švancara, K. Vytřas; Eds.). 2013/2014, vol. 8. (2014).*

Google Machine Translation of WO-2017194746-A1, (https://patents.google.com/patent/WO2017194746A1/en?oq=pct%2fep2017%2f061479) p. 1-15. (Year: 2017).*

[No Author Listed] Agilent Technologies, "Agilent B1500A Semiconductor Device Analyzer User's Guide", Edition 7, Oct. 2008, p. 1-628.

Asad, M., et al., "Surface Acoustic Wave Based H2S Gas Sensors Incorporating Sensitive Layers of Single Wall carbon Nanotubes Decorated With Cunanoparticles," Sensors and Actuators B 198 (2014) pp. 134-141.

Balasubramanian, K, et al., "Chemically Functionalized Carbon Nanotubes," Small (2005) vol. 1, No. 2, pp. 180-192.

Bard, A., et al., "Electrochemical Methods, Fundamentals and Applications," Second Edition, John Wiley & Sons, Inc., New York, Copyright (2001) © John Wiley & Sons, Inc. All rights reserved. ISBN 0-471-04372-9, pp. 1-850.

Bhattacharya, M., et al., "Carbon Nanotube Based Sensors for the Detection of Viruses," Sensors and Actuators B 155, (2011), pp. 67-74.

Bianco, A., Presentation Nanotube Functionalization and Therapeutic Applications, Immunologie et Chimie Therapeutiques, CNRS, Strasbourg, France, Nanosoft (Roscoff), May 21-25, (2007), pp. 1-68.

(56) References Cited

OTHER PUBLICATIONS

Bietz, J.A., et al., "Identity of High Molecular Weight Gliadin and Ethanol-Soluble Glutenin, Subunits of Wheat: Relation to Gluten Structure," Cereal Chem. (1980), vol. 57, No. 6, pp. 415-421.
Capparelli, R., et al., "Quantification of Gliadin Levels to the Picogram Level by Flow Cytometry," Wiley-Liss, Inc., Cytometry Part A 63A, (2005), pp. 108-113.
Chakravarty, P., et al., "Thermal Ablation of Tumor Cells With Antibody-Functionalized Single-Walled Carbon Nanotubes," PNAS, Jun. 24, (2008), vol. 105, No. 25, pp. 8697-8702.
Chopra, S., et al., "Selective Gas Detection Using a Carbon Nanotube Sensor," Applied Physics Letters, vol. 83, No. 11, Sep. 15, 2003, pp. 2280-2282.
Coyle, B., et al., "Carbon-Binding Designer Proteins That Discriminate Between sp2-and sp3-Hybridized Carbon Surfaces," American Chemical Society, Langmuir, (2013), vol. 29, pp. 4839-4846.
de Gracia Villa, M., et al., "Carbon Nanotube Composite Peptide-Based Biosensors as Putative Diagnostic Tools for Rheumatoid Arthritis," Biosensors and Bioelectronics, (2011), vol. 27 pp. 113-118.
De Leo, F., et al., "Structural and Dynamic Properties of Monoclonal Antibodies Immobilized on CNTs: A Computational Study," Chemistry European Journal, (2013), vol. 19, pp. 12281-12293.
Deng, C., et al., "Electrochemical Detection of Nitrite Based on the Polythionine/Carbon Nanotube Modified Electrode," Thin Solid Films 520, (2012), pp. 7026-7029.
Desai, S.C., et al., "Hypergolic Fuel Detection Using Individual Single Walled Carbon Nanotube Networks," Journal of Applied Physics, (2010) vol. 107, pp. 114509-1-114509-17.
Didar, T.F., et al., Improved treatment of systemic blood infections using antibiotics with extracorporeal opsonin hemoadsorption. Biomaterials. Oct. 2015;67:382-92. doi: 10.1016/j.biomaterials/015.07.046. Epub Jul. 26, 2015.
Drouvalakis, K., et al., "Peptide-Coated Nanotube-Based Biosensor for the Detection of Disease-Specific Autoantibodies in Human Serum, Biosensors and Bioelectronics, (2008), vol. 23, pp. 1413-1421.
Efrat, A., et al., Curve Matching, Time Warping, and Light Fields: New Algorithms for Computing Similarity Between Curves, Department of Computer Science, University of Arizona, Suresh Venkatasubramanian, AT&T Labs—Research, (2007), pp. 1-19.
Eissa, S., et al., "A Graphene-Based Electrochemical Competitive Immunosensor for the Sensitive Detection of Okadaic Acid in Shellfish", Nanoscale, (2012), vol. 4, pp. 7593-7599.
Extended European Search Report for Application No. 15846637.5, dated Apr. 3, 2018 (7 pages).
Fadel, T., et al., "Clustering of Stimuli on Single-Walled Carbon Nanotube Bundles Enhances Cellular Activation," Langmuir, (2010), vol. 26 No. 8, pp. 5645-5654.
Fernstrom, J.D., et al., "Mechanisms for Sweetness1-3," The Journal of Nutrition, Supplement May 9, 2012, pp. 1S of 8S.0.
Forsyth, R., et al., Graphene Field Effect Transistors for Biomedical Applications: Current Status and Future Prospects. Diagnostics (Basel). Jul. 26, 2017;7(3), 18 pages. pii: E45. doi: 10.3390/diagnostics7030045.
Fu, B.X., "Salt-Induced Disaggregation/Solubilization of Gliadin and Glutenin Proteins in Water," Journal of Cereal Science 24 (1996) 241-246.
Gao, N., et al., Specific detection of biomolecules in physiological solutions using graphene transistor biosensors. Proc Natl Acad Sol U S A. Dec. 20, 2016;113(51):14633-14638. doi: 10.1073/pnas.1625010114. Epub Dec. 5, 2016.
Garcia-Aljaro, C., et al., "Carbon Nanotubes-Based Chemiresistive Biosensors for Detection of Microorganisms," Biosensors and Bioelectronics 26 (2010) 1437-1441.
Gowda, P., et al., Chemical Vapor Detection Using Nonlinear Electrical Properties of Carbon Nanotube Bundles, Nanotechnology vol. 25 (2014) pp. 1-5.
Greene, F., "In Vitro Synthesis of Wheat (*Triticum aestivum* L.) Storage Proteins1," Plant Physiol. (1981) vol. 68, pp. 778-783.

Heller, D., et al., "Peptide Secondary Structure Modulates Single-Walled Carbon Nanotube Fluorescence as a Chaperone Sensor for Nitroaromatics," PNAS May 24, 2011, vol. 108, No. 21, pp. 8544-8549.
Hnaien, M., et al., "Impedimetric Microbial Biosensor Based on Single Wall Carbon Nanotube Modified Microelectrodes for Trichloroethylene Detection," Electrochimica Acta 56 (2011) pp. 10353-10358.
Hoaglan, R., "The Determination of Gliadin or Alcohol-Soluble Protein in Wheat Flour," The Journal of Industrial and Engineering Chemistry, (1911), Proteins of the Wheat Kernel Pub by Carnegie Inst, pp. 838-842.
Huang, T.S. et al., "Immobilization of Antibodies and Bacterial Binding on Nanodiamond and Carbon Nanotubes for Biosensor Applications," Diamond and Related Materials vol. 13, (2004), pp. 1098-1102.
Hui, Y., et al., "A 2.8 Ghz Combined Mode of Vibration Aluminum Nitride MEMS Resonator With High Figure of Merit Exceeding 45," (2013) Joint UFFC, EFTF and PFM Symposium pp. 930-932.
Hui, Y., et al., "Resonant Infrared Detector Based on a Piezoelectric Fishnet Metasurface," (2015) IEEE, pp. 1-3.
Huntington, M.D., et al., A Portable, Benchtop Photolithography System Based, "On a Solid-State Light Source," Supporting Information, Small, (2011), pp. S1-S7.
Huntington, M.D., et al., A Portable, Benchtop Photolithography System Based, "On a Solid-State Light Source," Small (2011), vol. 7, No. 22, pp. 3144-3147.
International Search Report and Written Opinion for Application No. PCT/US2015/053793, dated Jan. 4, 2016 (12 Pages).
International Search Report and Written Opinion for Application No. PCT/US2019/15579, dated Jun. 18, 2019 (13 pages).
International Search Report and Written Opinion for Application No. PCT/US2019/34043, dated Sep. 30, 2019 (12 Pages).
Jain, S., et al., "Development of an Antibody Functionalized Carbon Nanotube Biosensor for Foodborne Bacterial Pathogens," J Biosens Bioelectron (2012), S:11, pp. 1-7.
Jiang, P., et al., "Molecular Mechanisms of Sweet Receptor Function," Chem. Senses 30 (Suppl 1): (2005), pp. 117-118.
Jin X. et al., "Detection of Human Adenovirus Hexon Antigen Using Carbon Nanotube Sensors," Journal of Virological Methods vol. 171, (2011), pp. 405-407.
Kabbe, G., Presentation "Functionalization: Tailoring Nanocarbons Through Attached Molecules and Particles," Freie Universitat Berlin, (2011).
Kang, J.H., et al., An extracorporeal blood-cleansing device for sepsis therapy. Nat Med. Oct. 2014;20(10):1211-6. doi: 10.1038/nm.3640. Epub Sep. 14, 2014.
Ke, G., et al., "A Novel Strategy to Functionalize Carbon Nanotubes With Cellulose Acetate Using Triazines as Intermediated Functional Groups," Carbohydrate Polymers 79 (2010) pp. 775-782.
Kim, B., et al., "Family-Selective Detection of Antibiotics Using Antibody-Functionalized Carbon Nanotube Sensors," Sensors and Actuators B 166-167 (2012) pp. 193-199.
Kim, K., et al., Presentation "Antibody-Functionalized Carbon Nanotubes in Cancer Therapy," Apr. 28, 2008, pp. 1-72.
Kodali, V.K., et al., "Nonperturbative Chemical Modification of Graphene for Protein Micropatteming," Langmuir (2011), vol. 27, No. (3), pp. 863-865.
Kruss, S., et al., "Neurotransmitter Detection Using Corona Phase Molecular Recognition on Fluorescent Single-Walled Carbon Nanotube Sensors," American Chemical Society J. Am. Chem. Soc. (2014), vol. 136, pp. 713-724.
Kuzmany, H., et al., "Functionalization of Carbon Nanotubes," Synthetic Metals vol. 141, (2004), pp. 113-122.
Lee, P.P., et al., "Targeting Colorectal Cancer Cells With Single-Walled Carbon Nanotubes Conjugated to Anticancer Agent SN-38 and EGFR Antibody," Biomaterials vol. 34, (2013) pp. 8756-8765.
Lerner, M.B., et al., Presentation Detecting Lyme Disease Using Antibody-Functionalized Single-Walled Carbon Nanotube Transistors, Department of Physics and Astronomy, University of Pennsylvania, 209 South 33rd Street, Philadelphia, PA 19104, (2014).

(56) References Cited

OTHER PUBLICATIONS

Li, C., et al., Mass Detection Using Carbon Nanotube-Based Nanomechanical Resonators, Applied Physics Letters vol. 84, No. 25, Jun. 21, 2004, pp. 5246-5248.

Li, R., et al., P-Glycoprotein Antibody Functionalized Carbon Nanotube Overcomes the Multidrug Resistance of Human Leukemia Cells, ACSNANO (2010), vol. 4, No. 3, pp. 1399-1408.

Li, X., et al., Transfer of Large-Area Graphene Films for High-Performance Transparent Conductive Electrodes, NANO Letters, (2009), vol. 9, No. 12, pp. 4359-4363.

Liang, X., et al., "Toward Clean and Crackless Transfer of Graphene," ACSNANO, (2011), vol. 5, No. 11, pp. 9144-9153.

Lillehoj, P.B., et al., Rapid electrochemical detection on a mobile phone. Lab Chip. Aug. 7, 2013;13(15):2950-5. doi: 10.1039/c3lc50306b.

Liu, J., et al., "Visible Light Detection Using Single-Walled Carbon Nanotube Film and Gold Nanoparticles or Nanorods," Journal of Applied Physics, vol. 107, (2010), pp. 1-4.

Ma, P., et al., "Dispersion and Functionalization of Carbon Nanotubes for Polymer-Based Nanocomposites: A Review," Composites: Part A 41 (2010), pp. 1345-1367.

Mairal, T., et al, "Microfluorimeter with disposable polymer chip for detection of coeliac disease toxic gliadin," Lab on a Chip, vol. 9, No. 24, Jan. 1, 2009, pp. 3535-3542.

Mao, S., et al., "Specific Biosensing Using Carbon Nanotubes Functionalized With Gold Nanoparticle—Antibody Conjugates" Carbon, vol. 48 (2010), pp. 479-486.

Mao, S., et al., Graphene-based electronic biosensors. J Mater Res, 2017;32(15):2954-2965.

Marches, R., et al., "Specific Thermal Ablation of Tumor Cells Using Single-Walled Carbon Nanotubes Targeted by Covalently-Coupled Monoclonal Antibodies," Int. J. Cancer: (2009), vol. 125, pp. 2970-2977.

Margolskee, RF., "Molecular Mechanisms of Bitter and Sweet Taste Transduction," The Journal of Biological Chemistry, (Issue of Jan. 4, 2002), vol. 277, No. 1, pp. 1-4.

Maruyama, H., et al., "Evaluation of Thermal Conductivity of Single Carbon Nanotubes in Air and Liquid Using a Fluorescence Temperature Sensor," Applied Physics Letters, 103, (2013), pp. 1-5.

Matsumoto, K. (Ed.), "Frontiers of Graphene and Carbon Nanotubes, Devices and Application," Springer Japan KK is Part of Springer Science+Business Media (2015), (www.springercom).

McDevitt, MR,, et al., "Tumor Targeting With Antibody-Functionalized, Radiolabeled Carbon Nanotubes," The Journal of Nuclear Medicine, (2007), vol. 48, No. 7, pp. 1180-1189.

Menard-Moyon, C., et al., "Functionalized Carbon Nanotubes for Probing and Modulating Molecular Functions," Chemistry & Biology 17, Feb. 26, 2010, pp. 107-115.

Miller, K. et al. "Portable gluten biosensor (Thesis)," University of Arizona, May 31, 2009; pp. FP-45, retrieved Mar. 13, 2018 from <http://hdl.handle.net/10150/192520>.

Moreira, F., et al., "Artificial Antibodies for Troponin T by its Imprinting on the Surface of Multiwalled Carbon Nanotubes: Its Use as Sensory Surfaces," Biosensors and Bioelectronics, vol. 28 (2011) pp. 243-250.

Moreno, M., Analysis of Polyphenols in White Wine by CZE With Amperometric Detection Using Carbon Nanotube-Modified Electrodes, Electrophoresis, (2011), vol. 32, pp. 877-883.

Moron, B., et al., "Sensitive Detection of Cereal Fractions That Are Toxic to Celiac Disease Patients by Using Monoclonal Antibodies to a Main Immunogenic Wheat Peptide1-3," Am J Clin Nutr, (2008), vol. 87 pp. 405-414.

Mulvey. J.J., et al., "Self-Assembly of Carbon Nanotubes and Antibodies on Tumours for Targeted Amplified Delivery," Nature Nanotechnology, (2013), vol. 8, pp. 763-771.

Naguib, N., et al., "Effect of Carbon Nanofibre Structure on the Binding of Antibodies," Nanotechnology, vol. 16, (2005), pp. 567-571.

Nassef, H.M., et al., Electrochemical immunosensor for detection of celiac disease toxic gliadin in foodstuff. Anal Chem. Dec. 1, 2008;80(23):9265-71. doi: 10.1021/ac801620j.

Neves, M.M., et al. An electrochemical deamidated gliadin antibody immunosensor for celiac disease clinical diagnosis. Analyst. Apr. 7, 2013;138(7):1956-8. doi: 10.1039/c3an36728b. Epub Feb. 12, 2013.

Orth, RA., et al., "A Comparative Study of the Proteins of Wheats of Diverse Baking Qualities," American Association of Cereal Chemists, Inc., (1972), pp. 268-275.

Pei-Tzu, C., et al, "Detection of Gliadin in Foods Using a Quartz Crystal Microbalance Biosensor That Incorporates Gold Nanoparticles," Journal of Agricultural and Food Chemistry, v. 60, No. 26, Jul. 4, 2012, pp. 6483-6492.

Penza, M., et al., Carbon Nanotube Acoustic and Optical Sensors for Volatile Organic Compound Detection, Nanotechnology, (2005), vol. 16, pp. 2536-2547.

Pham, X.H., et al., "Electrochemical Characterization of a Single-Walled Carbon Nanotube Electrode for Detection of Glucose," Analytica Chimica Acta, (2010), vol. 671, pp. 36-40.

Pilolli, R., et al., "Advances in biosensor development based on integrating nanotechnology and applied to food-allergen management," Trends in Analytical Chemistry, Jun. 1, 2013, v. 47, pp. 12-26.

Plata, D.L., et al., "Thermogravimetry-Mass Spectrometry for Carbon Nanotube Detection in Complex Mixtures," American Chemical Society Environ. Sci. Technol., (2012), vol. 46, pp. 12254-12261.

Pumera, M., et al., Graphene for electrochemical sensing and biosensing. TrAC Trends in Analytical Chemistry, Oct. 2010, vol. 29, Issue 9, pp. 954-965.

Pumera, M., Graphene in biosensing. materialstoday, Jul.-Aug. 2011;14(7-8):308-315.

Qian, Z., et al., "245 MHZ Graphene-Aluminum Nitride Nano Plate Resonator," Transducers 2013, Barcelona, Spain, (Jun. 16-20, 2013), pp. 2005-2008.

Qian, Z., et al., "Single Transistor Oscillator Based on a Graphene-Aluminum Nitride Nano Plate Resonator," (2013) Joint UFFC, EFTF and PFM Symposium, pp. 559-561.

Qian, Z., et al., High Resolution Calorimetric Sensing Based on Aluminum Nitride MEMS Resonant Thermal Detectors, (2014) IEEE, pp. 1-4.

Qian, Z., et al., "1.27 GHZ Graphene-Aluminum Nitride Nano Plate Resonant Infrared Detector," Transducers (2015), Anchorage, Alaska, pp. 1429-1432.

Qian, Z., et al., Graphene as a Massless Electrode for Ultrahigh-Frequency Piezoelectric Nanoelectromechanical Systems, American Chemical Society Nano Lett. (2015), vol. 15, pp. 4599-4604.

Rajabzade, H., et al., Functionalized Carbon Nanotubes With Gold Nanoparticles to Fabricate a Sensor for Hydrogen Peroxide Determination, E-Journal of Chemistry (2012), vol. 9, No. 4, pp. 2540-2549.

Remaggi, F., et al., "Carbon Nanotube Sensor for Vibrating Molecules," New Journal of Physics vol. 15, (2013) 083016 pp. 1-20.

Resczenski, J., et al., Presentation "Functionalizing Carbon Nanotubes with Antibodies for the Detection of Prostate Cancer Biomarkers," Johnson Group, Sunfest, (2011), pp. 1-14.

Rotariu, L., et al., "Low Potential Thiocholine Oxidation at Carbon Nanotube-Ionic Liquid Gel Sensor," Sensors and Actuators B 150, (2010) pp. 73-79.

Santavicca, D.F., et al., "Bolometric and Nonbolometric Radio Frequency Detection in a Metallic Single-Walled Carbon Nanotube," Applied Physics Letters, (2011), vol. 98, pp. 1-4.

Shampine, L.F., et al., "Solving Index 1 DAES in Matlab and Simulink," Draft Paper Feb. 22, 1999, pp. 1-15.

Sharma, D., et al., Insight into the biosensing of graphene oxide: Present and future prospects. Arabian Journal of Chemistry, Mar. 2016;9(2):238-261.

Sirdeshmukh, R., et al., "Functionalization of Carbon Nanotubes with Antibodies for Breast Cancer Detection Applications," Proceedings of the 2004 International Conference on MEMS, NANO and Smart Systems, (2004), IEEE pp. 1-6.

Song, Y., et al., "Carbon Nanotube Volatile Organic Liquid Sensor," Applied Physics Letters 95, (2009), pp. 1-4.

(56) References Cited

OTHER PUBLICATIONS

Sousa, C., et al., "Sensitive Detection of Cereal Fractions That Are Toxic to Coeliac Disease Patients, Using Monoclonal Antibodies to a Main Immunogenic Gluten Peptide," Celiac Disease—From Pathophysiology to Advanced Therapies, Department of Microbiology and Parasitology, Faculty of Pharmacy, University of Seville, Seville, Spain, (2008).
Stefansson, S., et al., "Targeting Antibodies to Carbon Nanotube Field Effect Transistors by Pyrene Hydrazide Modification of Heavy Chain Carbohydrates," Journal of Nanotechnology vol. 2012, Article ID 490175, pp. 1-8.
Takeda, S., et al., "Application of Carbon Nanotubes for Detecting Anti-Hemagglutinins Based on Antigen—Antibody Interaction," Biosensors and Bioelectronics, vol. 21 (2005) pp. 201-205.
Tooski, S.B., Functionalized Single Wall Carbon Nanotube Sensor in a Perturbed Microwave Resonant Cavity Based Toxin/Pollutant Gas Pressure Sensor, Journal of Applied Physics, vol. 107, (2010), pp. 1-10.
Tooski, S.B., Sense Toxins/Sewage Gases by Chemically and Biologically Functionalized Single-Walled Carbon Nanotube Sensor Based Microwave Resonator, Journal of Applied Physics, vol. 107, (2010), pp. 1-9.
Tooski, SB, et al., "Optical Properties of Carbon Nanotube Gas Sensor," Journal of Applied Physics, vol. 110, (2011), pp. 1-8.
Varghese, et al. "Recent advances in graphene based gas sensors" Sensors and Actuators; 2015; vol. B 218; pp. 160-183.
Venturelli E., et al., "Antibody Covalent Immobilization on Carbon Nanotubes and Assessment of Antigen Binding," Small (2011), vol. 7, No. 15, pp. 2179-2187.
Villamizar, R., et al., "Rapid Detection of Aspergillus Flavus in Rice Using Biofunctionalized Carbon Nanotube Field Effect Transistors," Anal Bioanal Chem, (2011), vol. 399 pp. 119-126.
Vlandas, A., et al., "Enzyme-Free Sugar Sensing in Microfluidic Channels With an Affinity-Based Single-Wall Carbon Nanotube Sensor," Analytical Chemistry, vol. 82, No. 14, (Jul. 15, 2010), pp. 6090-6097.
Volkov, A.N., et al., "Effect of Bending Buckling of Carbon Nanotubes on Thermal Conductivity of Carbon Nanotube Materials," Journal of Applied Physics, vol. 111, (2012) pp. 1-12.
Wang, X., et al., "Transparent, Stretchable, Carbon-Nanotube-Inlaid Conductors Enabled by Standard Replication Technology for Capacitive Pressure, Strain and Touch Sensorst," J. Mater. Chem. A, (2013), vol. 1, pp. 3580-3586.
Wardani, N.I., et al., "Zinc Layered Hydroxide-2(3-Chlorophenoxy) Propionate Modified Multi-Walled Carbon Nanotubes Paste Electrode for the Determination of Nano-Molar Levels Copper (II)," Sensors and Actuators B 198, (2014), pp. 243-248.
Wieser H, "Chemistry of Gluten Proteins," Food Microbiology vol. 24, (2007), pp. 115-119.
Xiao, Y., et al., "Anti-HER2 IgY Antibody-Functionalized Single-Walled Carbon Nanotubes for Detection and Selective Destruction of Breast Cancer Cells," BMC Cancer, 2009, vol. 9 No. 351 pp. 1-11.
Xu, J., et al., "Fabrication of a Magnet-Assisted Alignment Device for the Amperometric Detection of Capillary Electrophoresis Using a Carbon Nanotube/Polypropylene Composite Electrode," Electrophoresis (2013), vol. 34, pp. 2017-2024.
Yang, K., et al., "Preparation and Functionalization of Graphene Nanocomposites for Biomedical Applications," Nature Protocols vol. 8 No. 12, (2013) pp. 2393-2403.
Yang, L, et al., "Carbon Nanotube-Sensor-Integrated Microfluidic Platform for Real-Time Chemical Concentration Detection," Electrophoresis (2009), vol. 30, pp. 3198-3205.
Yun, Y., et al., "A Nanotube Array Immunosensor for Direct Electrochemical Detection of Antigen—Antibody Binding," Sensors and Actuators B vol. 123 (2007) pp. 177-182.
Than, et al. "Graphene Field-Effect Transistor and Its Application for Electronic Sensing" Small; 2014; vol. 10; No. 20; pp. 4042-4065.
Zhao C. et al., "Formation of Uniform Reduced Graphene Oxide Films on Modified PET Substrates Using Dropasting Method," Particuology vol. 17 (2014) pp. 66-73.
International Preliminary Report on Patentability for Application No. PCT/US2015/053793, dated Apr. 13, 2017 (11 Pages).

* cited by examiner

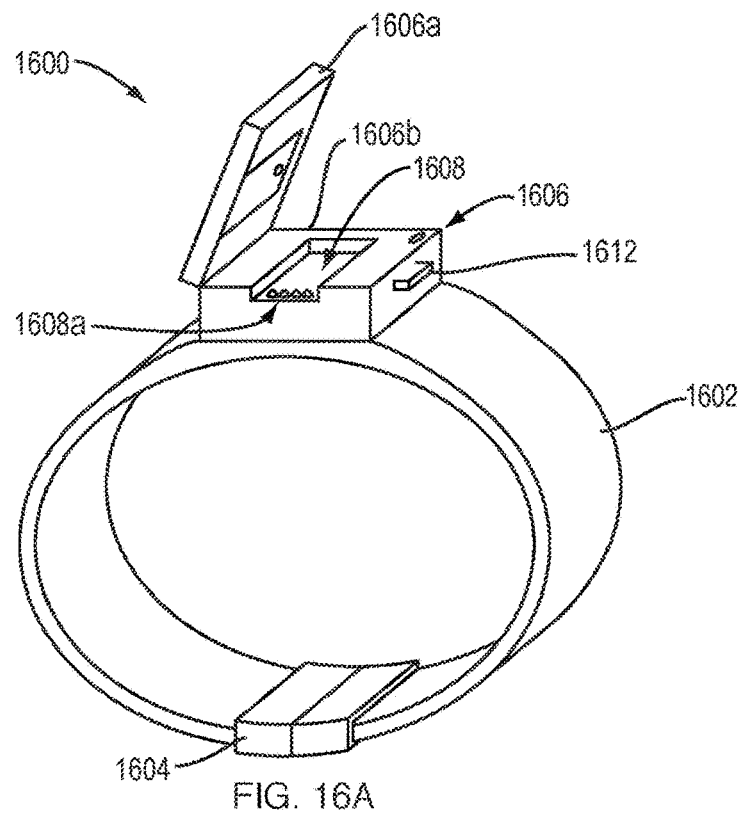
FIG. 16A
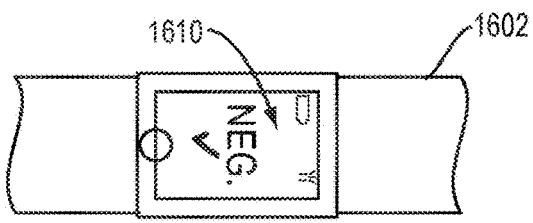
FIG. 16B
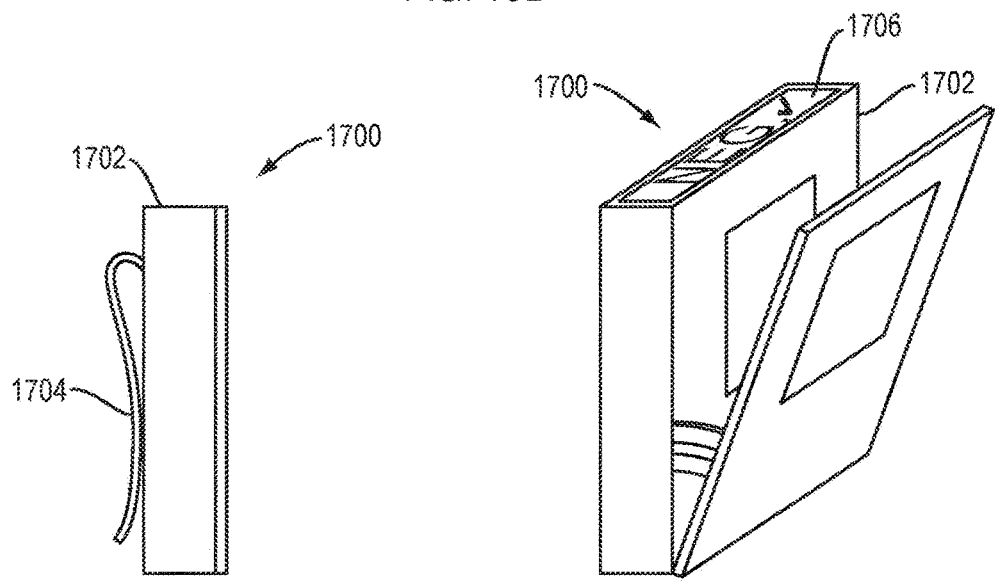
FIG. 17A
FIG. 17B

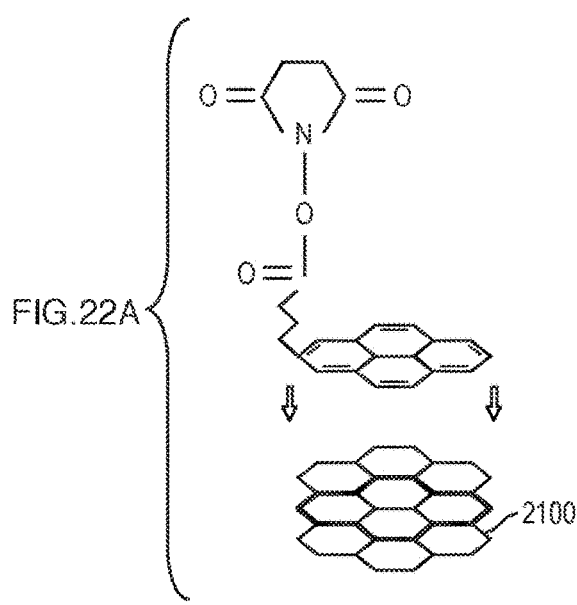
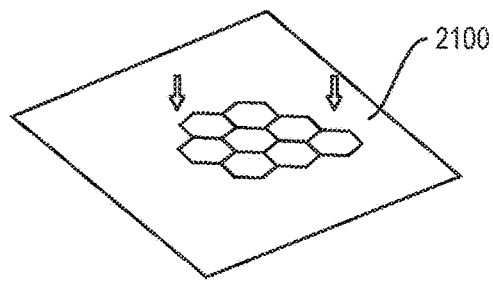
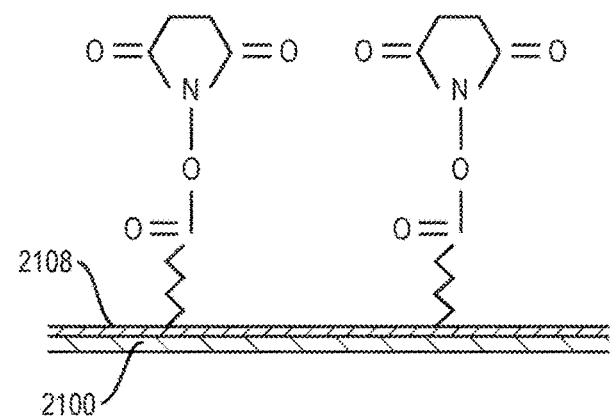
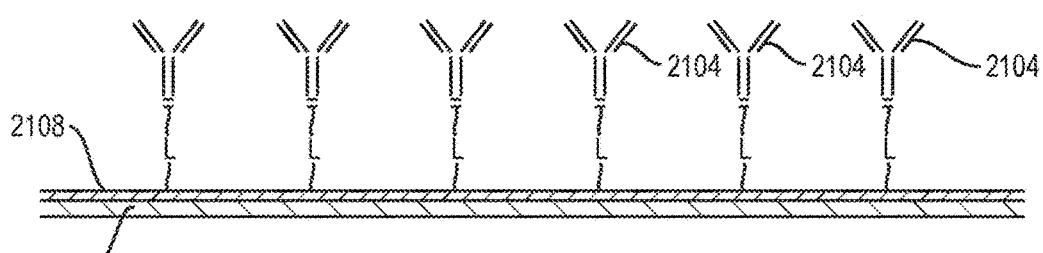
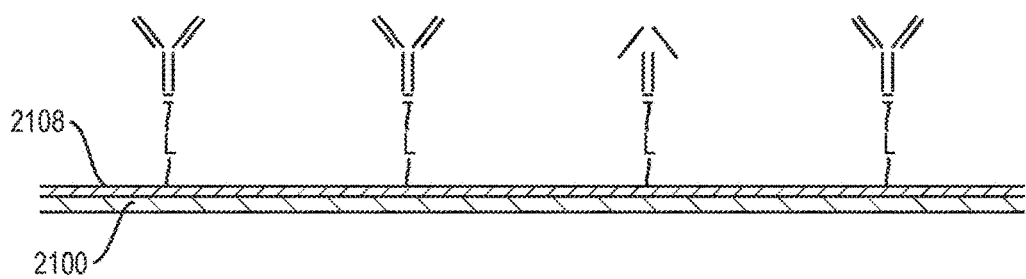
FIG.22A
FIG.22B
FIG.22C
FIG.22D
FIG.22E

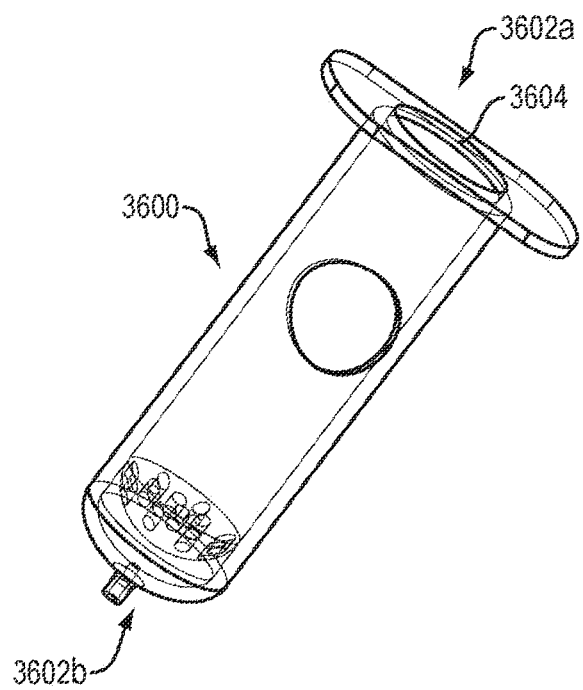
FIG. 36A
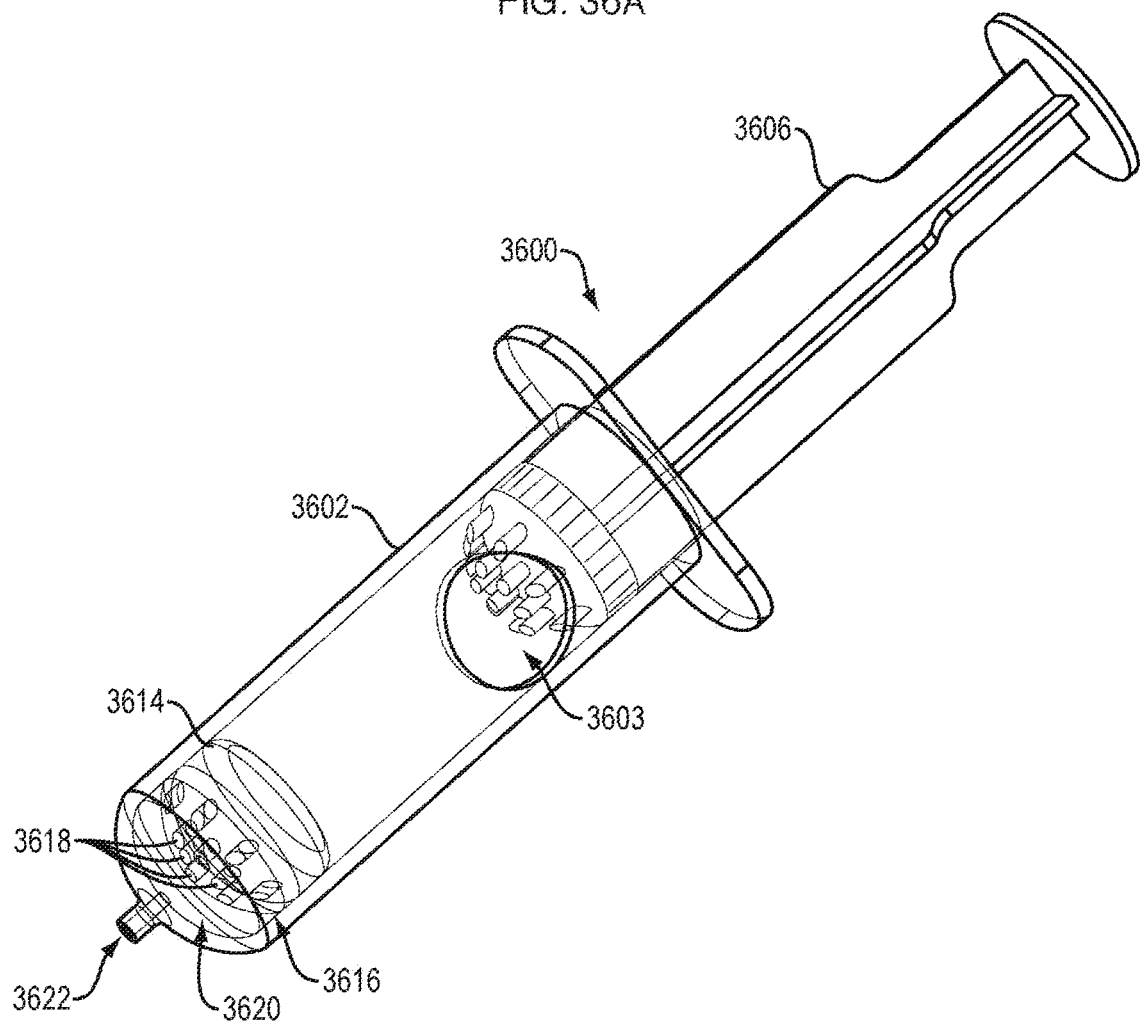

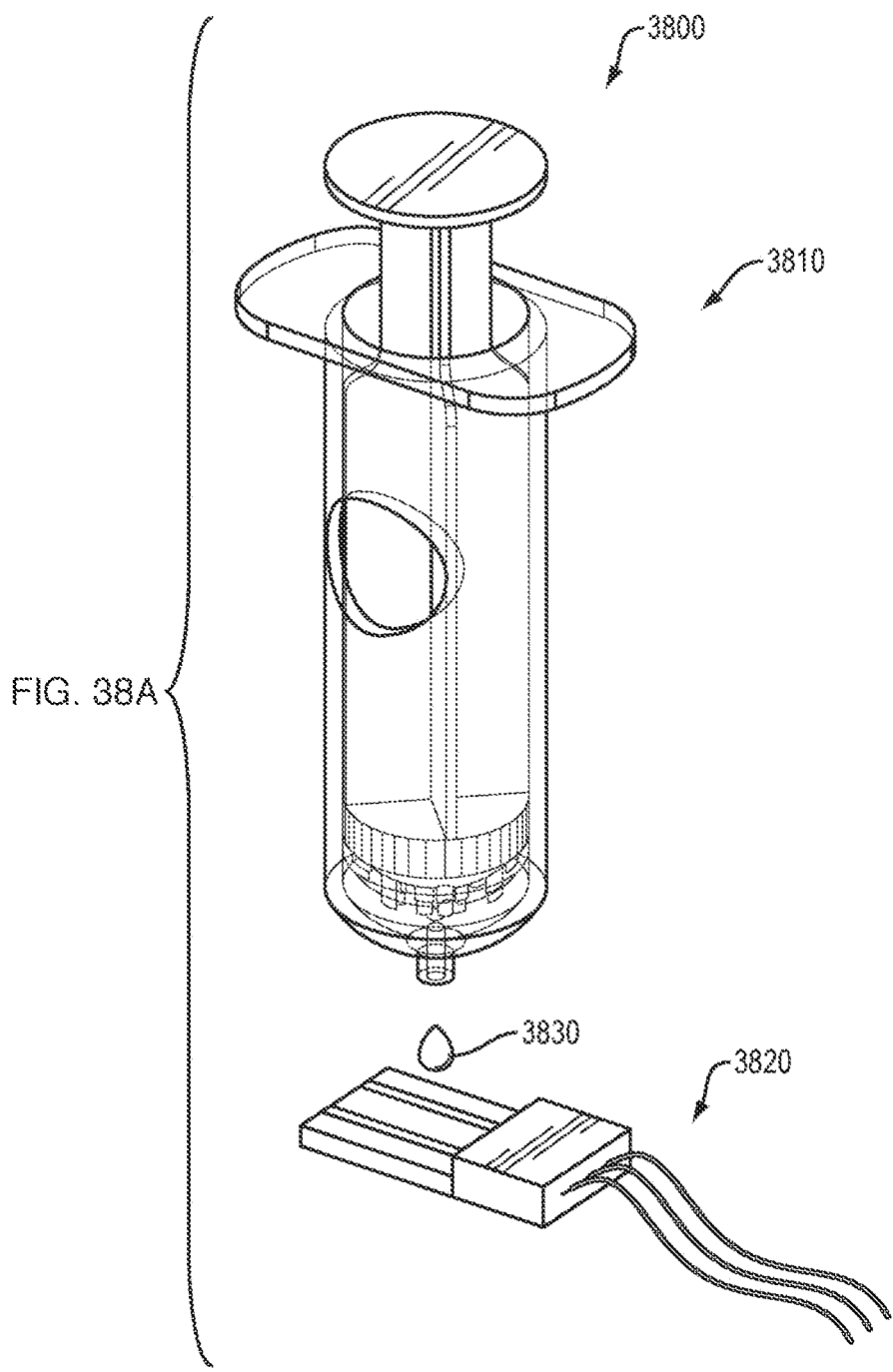

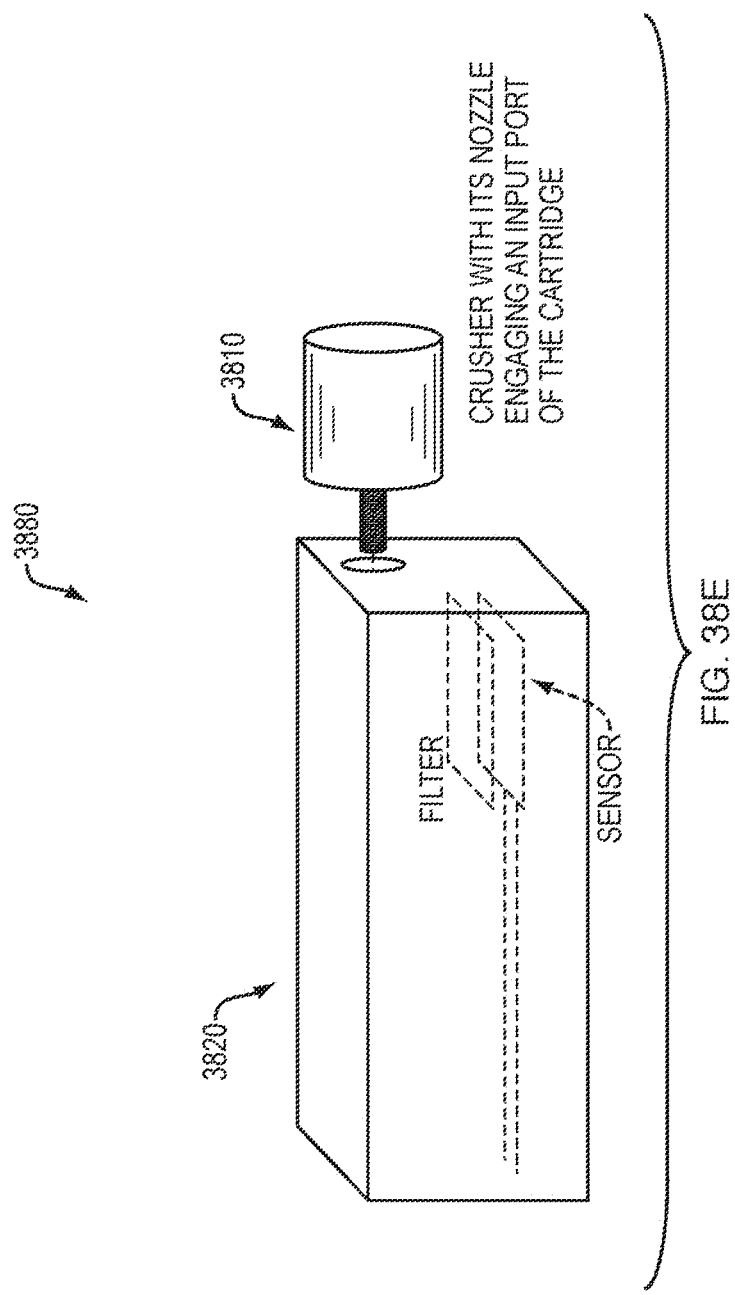

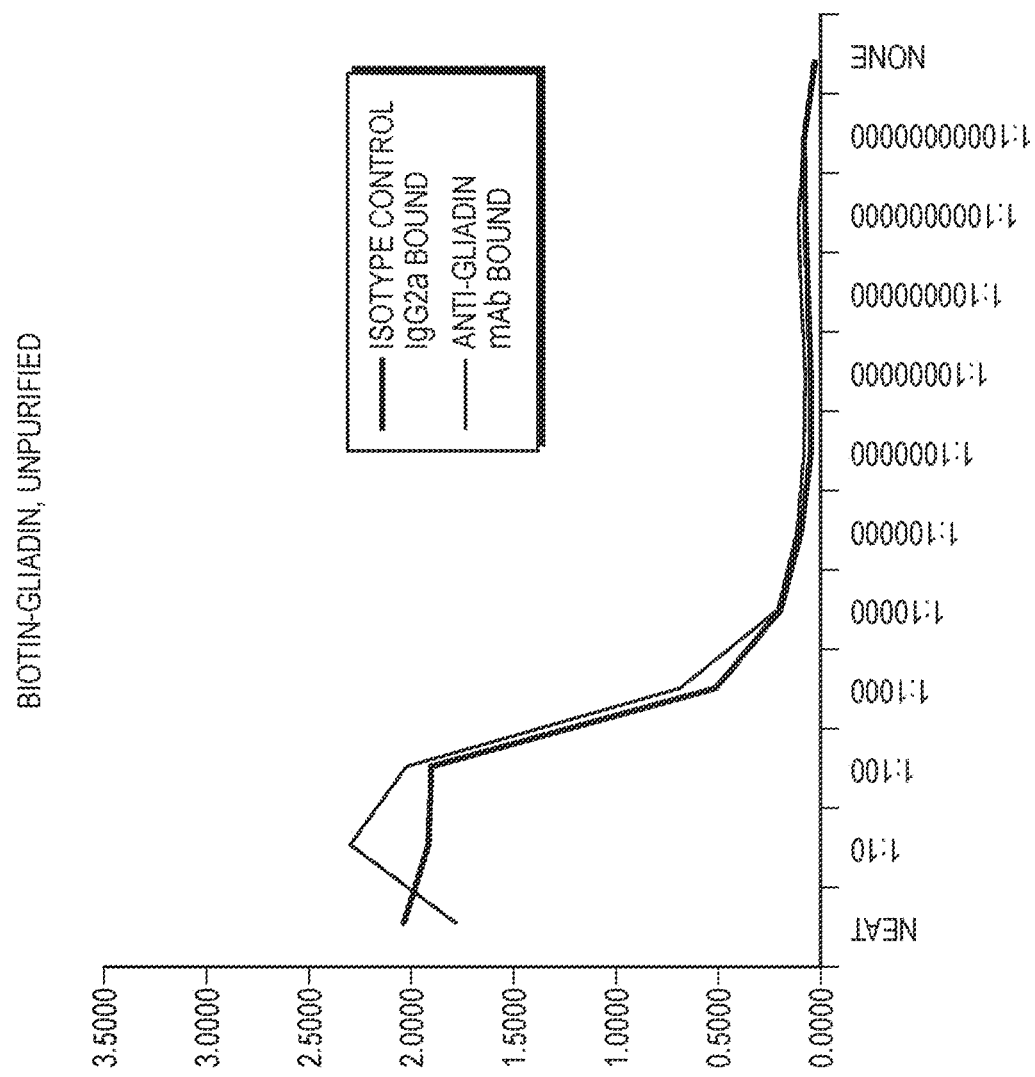

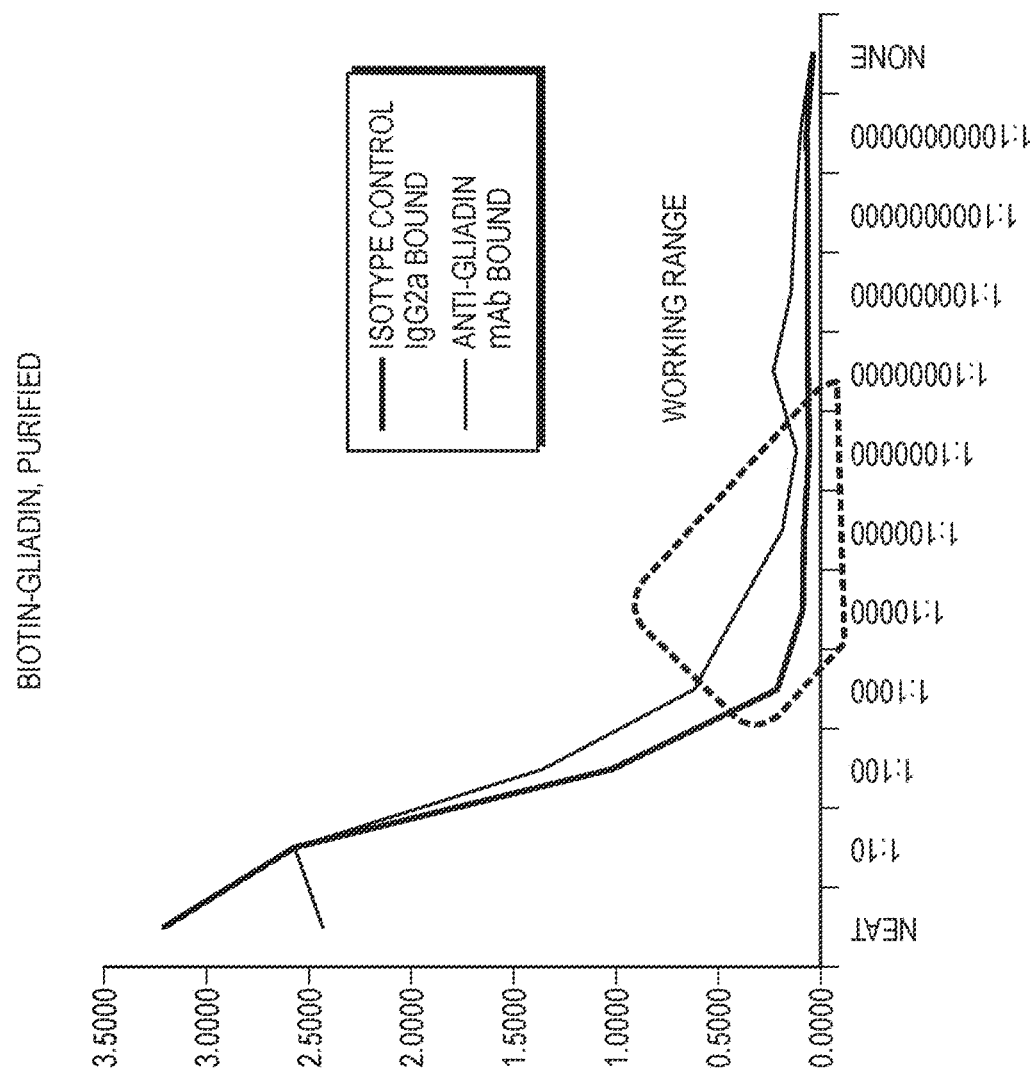

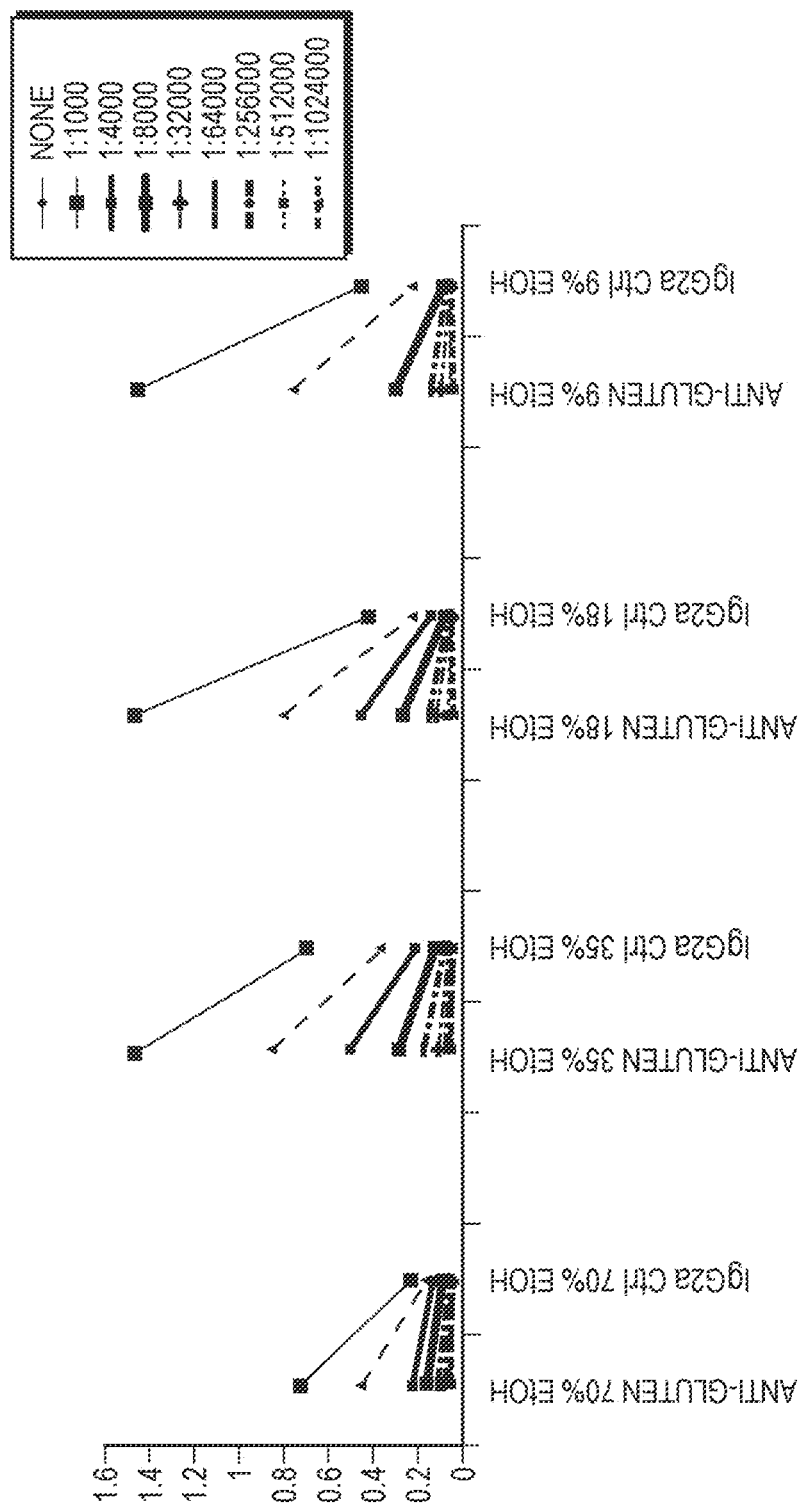

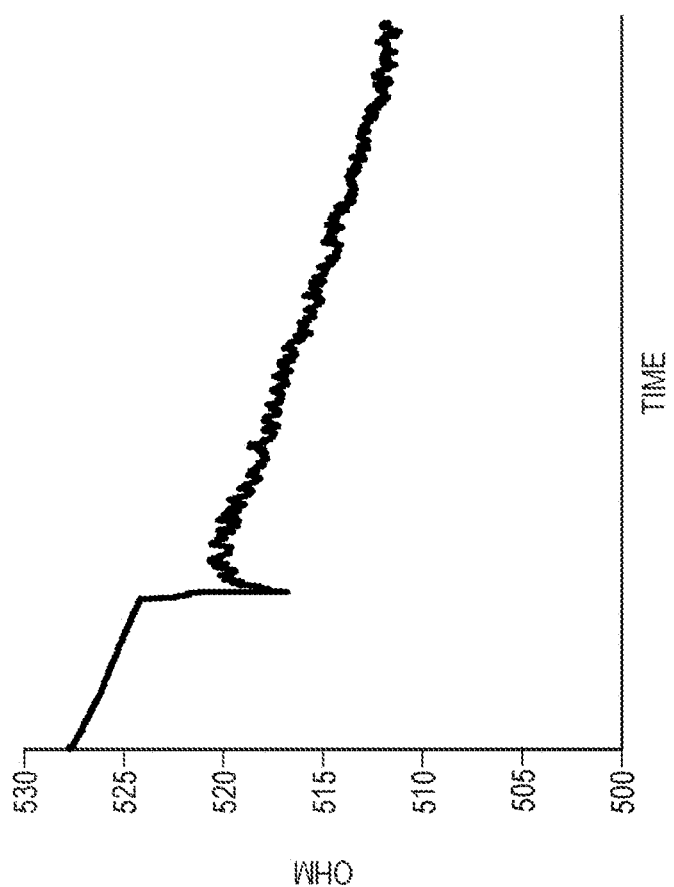

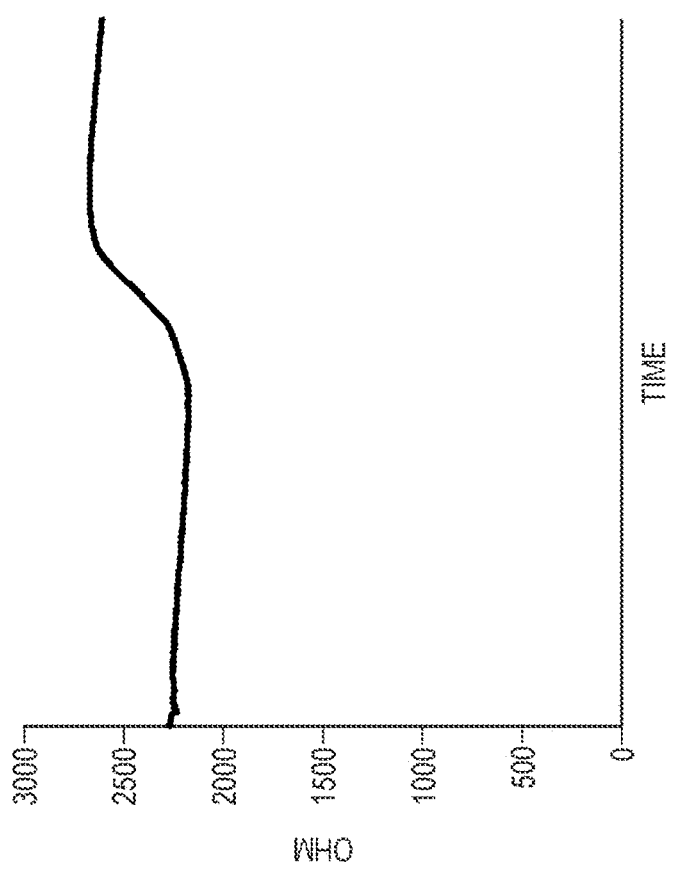

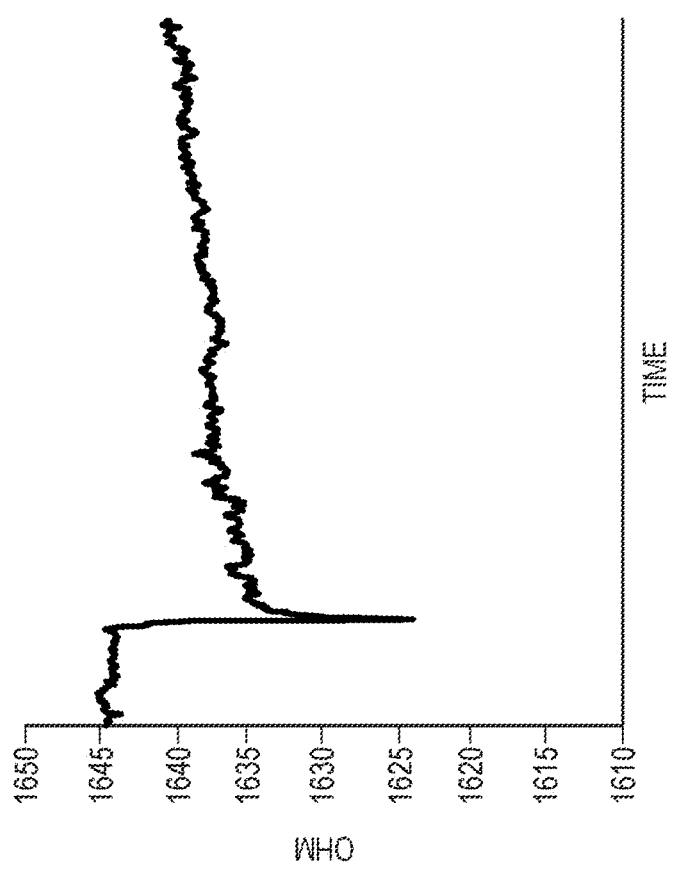

DEVICE AND METHOD FOR CHEMICAL ANALYSIS

CROSS-REFERENCE TO RELATED APPLICATIONS

This U.S. patent application is a continuation-in-part of U.S. application Ser. No. 15/357,445, filed on Nov. 21, 2016. U.S. application Ser. No. 15/357,445 is a continuation of U.S. application Ser. No. 14/874,228, filed on Oct. 2, 2015, and now issued as U.S. Pat. No. 9,664,674. U.S. application Ser. No. 14/874,228 claims the benefit of priority to U.S. Provisional Application No. 62/059,731, filed on Oct. 3, 2014; and U.S. Provisional Application No. 62/206,471, filed on Aug. 18, 2015, both titled "DEVICE AND METHOD FOR CHEMICAL ANALYSIS." This application also claims the benefit of priority to U.S. Provisional Application No. 62/676,079, filed on May 24, 2018 and entitled "A GRAPHENE-FUNCTIONALIZED SENSOR." The entire contents of each of these applications are incorporated herein by reference.

BACKGROUND

The present disclosure is directed to methods, systems, and devices for identifying and quantifying constituents of a sample, e.g., a liquid sample.

A variety of conventional systems are known for analysis of constituents of a sample. Such conventional systems, however, suffer from a number of shortcomings. For example, their applicability can be limited, or they can be expensive or difficult to use.

Accordingly, there is a need for improved systems and methods for analysis of samples, such as food samples, so as to identify and optionally quantify one or more of their constituents.

SUMMARY

In various embodiments, a variety of different compounds, and in particular those that are responsible for the sensation of taste, can modulate the electrical properties of fullerenes, such as carbon nanotubes, in unique ways. In some embodiments, such modulations of the electrical properties of fullerenes in response to interaction with a variety of different compounds provide unique signatures of those compounds. Those signatures may in turn be used for identifying and quantifying those compounds in a sample, e.g., a liquid sample.

By way of example, the interaction, e.g., contact, of a compound (e.g., sugar molecules) with a plurality of carbon nanotubes can change the DC electrical resistance of the nanotubes. Further, the change in the DC electrical resistance of the carbon nanotubes can be correlated with the concentration of that compound in a sample.

In other cases, the signature of a compound can be based on the way its interaction, e.g., contact, with a plurality of carbon nanotubes, or other fullerenes, can change the AC impedance of the carbon nanotubes.

In some embodiments, a sensor according to the present teachings exhibits a temporal change in resistance in response to contact with a species of interest, where the temporal variation of resistance can uniquely identify that species. For example, in response to contact with a species (e.g., a molecular species), the resistance of the sensor can change as a function of time in a manner that is indicative of that species. In some cases, a Fourier transform (e.g., a fast Fourier transform (FFT)) of the resistance of the sensor as a function of time in response to contact with a species can provide the requisite information for identifying that species. In some cases, such temporal variation of the resistance can be employed to identify multiple species that may be simultaneously present in a sample (e.g., a liquid sample). By way of example, the interaction of certain species with the sensor (e.g., the nanotube mesh of the sensor) can result in a temporal variation of sensor's resistance that is characterized primarily by low-frequency components in the Fourier transform spectrum while the interaction of another species with the sensor may result in a temporal variation of the sensor's resistance that is characterized primarily by high-frequency components in the respective Fourier transform spectrum. In this manner, various species, even when concurrently present in a liquid sample, may be identified and quantified.

In some embodiments, sensing elements comprising fullerenes, such as carbon nanotubes, are employed to detect selected compounds within a liquid sample, and to determine their respective concentrations. By way of example, as discussed in more detail below, in some embodiments, a liquid sample can be introduced onto a sensing element, which comprises a plurality of carbon nanotubes, such that one or more of its molecular constituents would interact with the carbon nanotubes. The change in one or more electrical properties of the carbon nanotubes in response to their interaction with the molecular constituents of the liquid sample can then be measured. Such electrical properties can include, e.g., DC electrical resistance, AC electrical impedance, or combinations thereof. For example, in some cases, the change in AC electrical impedance at one or more AC frequencies can be measured. The changes in the electrical properties of the carbon nanotubes can then be correlated to the presence and concentration of selected species (e.g., molecular species) in the liquid sample.

In some cases, the collected data can be compared with calibration data that had been previously obtained in order to analyze the liquid sample for the presence and concentration of selected species (e.g., molecular species). For example, the response of a sensing element to a calibration liquid sample comprising various concentrations of sugar molecules (e.g., fructose and/or glucose) in deionized water can be measured and stored in a database. Such calibration data can then be employed to analyze the electrical response of a sensing element to a liquid sample under study to identify and quantify sugar molecules in that sample. In some cases, the analysis of the sample includes a statistical analysis, such as, principal component analysis, that employs the calibration data corresponding to selected molecular species as basis vectors to determine concentrations of those species in a liquid sample under study. In some cases, such a database can be stored on a central server to be accessible via the Internet so that various devices according to the present teachings can access the database for analyzing a sample under study.

In some embodiments, one or more filters, e.g., nanofilters, are employed to segregate different species present in a liquid sample, e.g., based on their molecular weight, mobility, or other properties. For example, in some embodiments in which the detection and quantification of several molecular species in a liquid sample are desired, a plurality of filters can be employed to segregate those species, if present in the sample, into a plurality of filtrates. Each filtrate can then be analyzed, e.g., by employing the fullerene-based sensors according to the present teachings, to detect the presence and/or concentration of a respective one of those molecular species.

In some embodiments, a sensor according to the present teachings can include a plurality of nanotubes, or other fullerenes, that are functionalized by one or more compounds to selectively interact with a species (e.g., molecular species) of interest. The modulation of one or more electrical properties of the functionalized carbon nanotubes in response to interaction with a liquid sample can then be predominantly due to the species of interest. In this manner, the concentration of the species (e.g., molecular species) of interest can be extracted. In such embodiments, the functionalized carbon nanotubes can be viewed as effectively providing a filtering function, which allows distinguishing the electrical signal associated with a species of interest from contributions of other species in the sample to the modulation of one or more electrical properties of the carbon nanotubes.

By way of example, a sensor according to the present teachings can include carbon nanotubes functionalized to selectively interact with polysaccharides. This can facilitate detecting and measuring the concentration of polysaccharides in a liquid sample. Another sensor can include carbon nanotubes functionalized with receptors for glutamate to selectively interact with glutamate to facilitate the detection of this species in a liquid sample. In some embodiments, in a device according to the present teachings, different groups of sensors can be functionalized for the detection of different species (e g, different molecular species). In this manner, the device can detect several species. In some cases, such detection can be done in parallel via simultaneous introduction of sample portions to each of said groups of sensors.

One application of the present teachings is to determine the "taste" of a food sample by detecting and quantifying molecular species that are responsible for the sensation of taste. In some cases, the food sample can be a liquid sample. In other embodiments, a solid food sample can be dissolved in an appropriate liquid (e.g., water or alcohol) to generate a liquid sample, which can then be analyzed by employing the methods and systems according to the present teachings.

In one aspect, a device is disclosed that can provide an indication of the "taste" of a liquid sample by identifying and quantifying the agents that are responsible for the sensation of taste. The sensation of taste is based on the following basic tastes: sweetness, saltiness, sourness, bitter and umami. Further, certain compounds, such as Capsaicin, which provide a sensation of pain, can nonetheless contribute to the subjective sensation of taste. This sensation is typically referred to as pungency.

For example, as discussed in more detail below, the device can include a plurality of sensors that can be employed in a manner discussed herein to identify and quantify sugars, salts, acids, glutamates, among other species, present in a liquid food sample. The concentration of these species can then be used to assign a taste, e.g., bitter-sweet, to the food sample.

The teachings of the present disclosure can have broad applicability for detecting and quantifying a variety of organic and inorganic compounds. In some embodiments, the species that contribute to the flavor of a food sample, such as mint, tarragon, turmeric, ginger, can be identified and quantified in a food sample using the teachings of the present disclosure.

In another embodiment, the present teachings can be employed to identify one or more gluten proteins in a food sample.

Moreover, in some embodiments, a wearable device for chemical analysis of a food sample is disclosed, which comprises a flexible element configured for removably and replaceably mounting onto a body part or clothing of an individual, and an analyzer that is coupled to said flexible element. The analyzer is configured for removably and replaceably receiving a cartridge, where the cartridge comprises at least one sensor configured for detecting one or more chemical species in a food sample. By way of example, the flexible element can be a wrist band that allows removably and replaceably securing the device to a user's wrist.

The sensor includes one or more sensing elements that can exhibit a change in one or more of their electrical properties in response to interaction with at least one chemical species of interest. For example, the sensor can include a plurality of carbon nanotubes and/or a graphene layer, which can exhibit a change in their electrical resistance in response to interaction with one or more chemical species in a food sample.

The analyzer can measure and analyze the change in one or more electrical properties of the sensing element(s) of the sensor in response to interaction with a food sample to determine if a species of interest is present in the food sample (e.g., whether the species is present in the food sample at a concentration above a detection threshold). By way of example, the analyzer can be configured to compare the temporal variations of at least one electrical property of the sensing element(s) with one or more calibration curves to determine the presence of said one or more chemical species in the food sample.

In a related aspect, a system for detecting one or more gluten proteins in a food sample is disclosed. The system comprises a cartridge for receiving a food sample, where the cartridge comprises a chamber for receiving a food sample and a reservoir for containing a process liquid. The food chamber includes an input port for introducing the food sample into the chamber and an output port. A frangible barrier separates the food chamber from the liquid reservoir such that breakage of the barrier allows at least a portion of the liquid stored in the reservoir to flow into the food chamber. The process liquid extracts at least a portion of the food sample to generate a test liquid containing said portion of the food sample. The cartridge further comprises a sensor, which includes one or more sensing elements positioned relative to the food chamber so as to receive at least a portion of the test liquid. An analyzer in communication with the sensing element(s) of the sensor measures a change, if any, in one or more electrical properties of the sensing element(s) and analyzes that change to determine whether a gluten protein is present in the food sample.

In some embodiments, the sensing element of the sensor comprises a graphene layer functionalized with a plurality of antibody molecules, where the anti-body molecules are capable of selectively binding to a gluten protein, such as gliadin.

In some embodiments, a passivation layer covers at least a portion of the graphene layer that is not functionalized by the anti-body molecules.

In another aspect, a filter is disclosed, which comprises a substrate, and a polymeric material applied to a top surface of the substrate. In some embodiments, the polymeric material comprises a polymer having the following chemical structure:

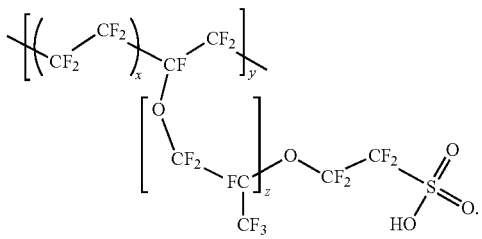

In some embodiments, the substrate is porous having a plurality of pores with sizes in a range of about 1 micrometer to about 100 micrometers. In some embodiments, the substrate can include a plurality of cellulose fibers. The filter can be both oleophobic and hydrophobic. Such a filter can have a variety of applications. For example, as discussed in more detail below, such a filter can be employed in a cartridge in accordance with the present teachings.

In some embodiments, a wearable device for chemical analysis of a food sample, the device comprising: a flexible element configured for removably and replaceably mounting onto a body part or clothing of an individual; and an analyzer coupled to said flexible element, said analyzer being configured for removably and replaceably receiving a cartridge, wherein said cartridge comprises at least one sensor configured for detecting one or more chemical species in the food sample.

In some embodiments, said at least one sensor comprises at least one sensing element exhibiting a change in one or more electrical properties thereof in response to interaction with said one or more chemical species.

In some embodiments, said analyzer is configured to be in communication with said cartridge to detect one or more electrical signals associated with said change in the one or more electrical properties of said at least one sensing element.

In some embodiments, said analyzer is further configured to analyze said one or more electrical signals to determine presence of said one or more chemical species in said food sample. In some embodiments, said analyzer is configured to compare said one or more electrical signals with calibration data to determine the presence of said one or more chemical species in the food sample. In some In some embodiments, said at least one sensing element comprises a plurality of carbon nanotubes. In some embodiments, said at least one sensing element comprises a graphene layer. In some embodiments, said graphene layer is functionalized with a plurality of antibody molecules. In some embodiments, said flexible element comprises a wrist band.

In some embodiments, a system for detecting one or more gluten proteins in a food sample comprises a cartridge for receiving the food sample, said cartridge comprising: a food chamber for receiving the food sample, said chamber having an input port for introducing the food sample therein and an output port, a liquid reservoir for containing a process liquid, a frangible barrier separating said food chamber from the liquid reservoir, and a sensor disposed relative to the output port of the food chamber so as to receive at least a portion of a test liquid exiting the food chamber, wherein the test liquid is generated via interaction of the process liquid and the food sample upon breakage of said frangible barrier; and an analyzer in electrical communication with said sensor to detect temporal variation of at least one electrical property of the sensor in response to interaction with said test liquid.

In some embodiments, said sensor comprises a graphene layer and a plurality of antibody molecules coupled to said graphene layer. In some embodiments, said sensor comprises a plurality of carbon nanotubes and a plurality of antibody molecules coupled to said plurality of carbon nanotubes. In some embodiments, said anti-body molecules are capable of selectively binding to a gluten protein. In some embodiments, said anti-body molecules are capable of selectively binding to a gluten protein. In some embodiments, said gluten protein is gliadin. In some embodiments, said gluten protein is gliadin. In some embodiments, the system further comprises a passivation layer disposed on at least a portion of said graphene layer not functionalized by said anti-body molecules.

In some embodiments, a filter comprises a substrate, a polymeric material applied to a top surface of the substrate, wherein said polymeric material comprises a polymer having the following chemical structure:

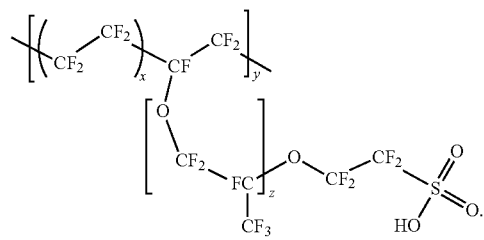

In some embodiments, said substrate comprises cellulose fibers. In some embodiments, said filter is oleophobic. In some embodiments, said filter is hydrophilic. In some embodiments, said substrate is porous. In some embodiments, said substrate includes pores with sizes in about 1 micrometer to 100 micrometers.

In some embodiments, a system for analyzing a liquid sample comprises at least one sensor configured to receive the liquid sample, said at least one sensor comprising a plurality of fullerenes, an analyzer configured to: measure a change in one or more electrical properties of said plurality of fullerenes in response to interaction with said liquid sample, and correlate said change to concentration of at least one species present in said liquid sample. In some embodiments, said plurality of fullerenes comprise a plurality of carbon nanotubes. In some embodiments, said at least one species comprises at least one protein associated with gluten.

In one aspect, a sensor for detecting an analyte in a sample, which comprises a graphene layer, a plurality of antibodies coupled to said graphene layer, said antibodies exhibiting specific binding to said analyte, and a reference electrode disposed in vicinity of said graphene layer. An AC (alternating current) voltage source is provided for applying an AC voltage to said reference electrode so as to generate a time-varying electric field at or near vicinity of the graphene surface. A plurality of electrical conductors is electrically coupled to the functionalized graphene layer for measuring an electrical property of said functionalized graphene layer.

In some embodiments, the AC voltage source is configured to apply an AC voltage with a frequency in a range of about 1 kHz to about 1 MHz to the reference electrode. In some embodiments, the AC voltage has an amplitude in a range of about 1 millivolt to about 3 volts.

In some embodiments, the reference electrode is positioned at a distance in a range of about 1 mm to about 2 mm above the antibody-functionalized graphene layer.

In some embodiments, the analyte comprises an allergen. In some embodiments, the analyte comprises a protein. For example, the analyte can be a gluten protein. In some embodiments, the analyte comprises a pathogen, such as bacteria and/or viruses.

The graphene layer can be deposited on a variety of different substrates. By way of example, in some embodiments, the graphene layer can be deposited on a semiconductor substrate, such as a silicon substrate.

Further understanding of various aspects of the embodiments can be obtained by reference to the following detailed description and the associated drawings.

BRIEF DESCRIPTION OF DRAWINGS

The drawings are not necessarily to scale or exhaustive. Instead, emphasis is generally placed upon illustrating the principles of the embodiments described herein. The accompanying drawings, which are incorporated in this specification and constitute a part of it, illustrate several embodiments consistent with the disclosure. Together with the description, the drawings serve to explain the principles of the disclosure.

In the drawings:

FIGS. 16A and 16B depict a wearable detection device according to an embodiment.

FIGS. 17A and 17B depict a wearable detection device according to another embodiment.

FIGS. 22A-22E depict a sensing element according to an embodiment.

FIGS. 36A-36D schematically depict a food processor according to an embodiment.

FIGS. 38A-38E show processing and detection systems according to various embodiments.

FIGS. 41A and 41B illustrate results of determining a working gliadin concentration range according to one embodiment.

FIGS. 43A-B also illustrate some effects of ethanol concentration on gliadin binding from different perspectives according to some embodiments.

FIG. 47A shows measurements for a sensor functionalized by anti-Gluten antibody, and exposed to none-Gluten solution according to an embodiment.

FIG. 47B shows measurements for a sensor covered with Tween 20 and exposed high dosage of Gluten according to an embodiment.

FIG. 48A shows the ohmic behavior of a sensor functionalized by mouse IgG control antibody, exposed to diluted gluten-alcohol solution according to an embodiment.

DETAILED DESCRIPTION

Figure 1:
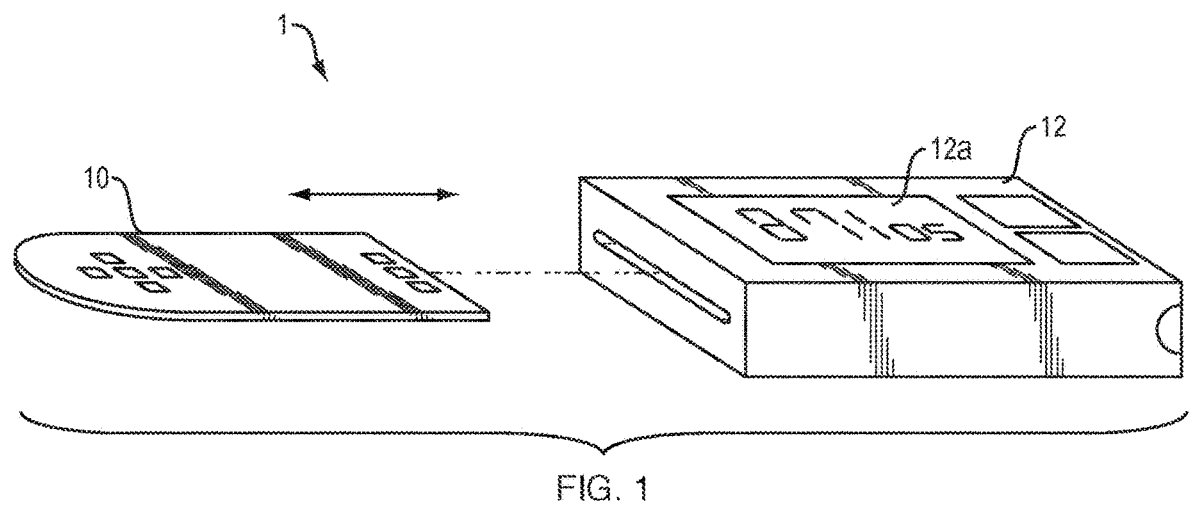
FIG. 1 schematically depicts a detection system according to an embodiment.

The following detailed description refers to the accompanying drawings. The same or similar reference numbers may be used in the drawings or in the description to refer to the same or similar parts. Also, similarly-named elements may perform similar functions and may be similarly designed, unless specified otherwise. Details are set forth to provide an understanding of the described embodiments. The embodiments may be practiced without some of these details. In other instances, well-known techniques, procedures, and components have not been described in detail to avoid obscuring the described embodiments.

SUMMARY OF SECTIONS

In what follows, section A describes various embodiments of detections systems, which detect presence of molecule in a food sample. Section B discloses various embodiments of food grinding systems, which are configured to grind or press a food sample, or mix it with a process liquid. Section C discloses filters utilized in various embodiments. Section D discloses various embodiments of processing and detection systems, which process a food sample and analyze it to detect a molecule of interest. And Section E discloses the experimental results for some embodiments.

A. DETECTION SYSTEMS

Some embodiments employ a detection system for detecting presence of a molecule in a food sample.

FIG. 1 schematically depicts a detection system 1 according to an embodiment of the present teachings. System 1 includes a cartridge 10 for receiving a sample, e.g., a liquid sample, and an analyzer 12 (herein also referred to as a reader unit) that can receive the cartridge to determine the presence and concentration of selected species (e.g., molecular ingredients) in the sample. The analyzer 12 can include a display 12a for presenting the results of the analysis of a sample to a user. The results may indicate whether particular species of interest are present, and if so, at what concentrations.

The cartridge 10 can include one or more sensors that are configured to interact with one or more species within a sample. The species may be molecular or atomic (neutral or charged) species. In many embodiments, the one or more sensors contained in the cartridge include a plurality of sensing elements. The plurality of sensor elements may include carbon nanotubes, graphene, buckyballs or other fullerenes. In some embodiments, electrical properties, e.g., electrical impedance (such as resistance), of the sensing elements can be modulated in response to an interaction, e.g., contact, with one or more species present in a liquid sample. The analyzer unit 12 can determine such modulation of the electrical properties of these sensing elements in response to interaction with one or more species in a sample. In addition, the analyzer unit 12 can determine the concentrations of the species via analysis of such modulation of the electrical properties of the sensing element(s).

Figure 2:
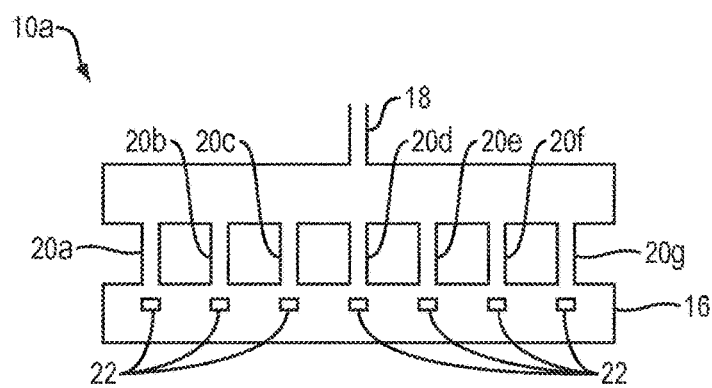
FIG. 2 schematically depicts a cartridge according to an embodiment.

A liquid sample can be introduced into the cartridge to interact with its sensing element(s) in a variety of different ways. By way of example, FIG. 2 schematically depicts an embodiment of a cartridge 10 a according to the present teachings. The cartridge 10 a includes a microfluidic sample delivery component 14 and a sensing component 16. The microfluidic sample delivery component 14 includes an inlet port 18 for receiving a liquid sample, and a plurality of microfluidic channels 20 a, 20 b, 20 c, 20 d, 20 e, 20 f, and 20 g (herein referred to collectively as channels 20). Channels 20 can deliver portions of the received sample to a plurality of sensing elements 22 disposed in the sensing component 16.

Figure 3:
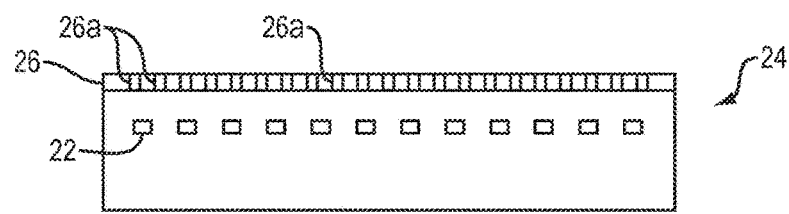
FIG. 3 schematically depicts a cartridge according to another embodiment.

FIG. 3 shows schematics of a cartridge 24 according to another embodiment. The cartridge 24 includes a porous top layer 26, and a plurality of sensing elements 22.

Porous top layer 26 provides one or more channels 26 a. When a liquid sample is disposed on the exposed surface of the porous layer 26, the channels 26 a guide the liquid to sensing elements 22. In some embodiments, the porous layer 26 may be formed of polymeric materials such as porous polyurethane.

Figure 4A:
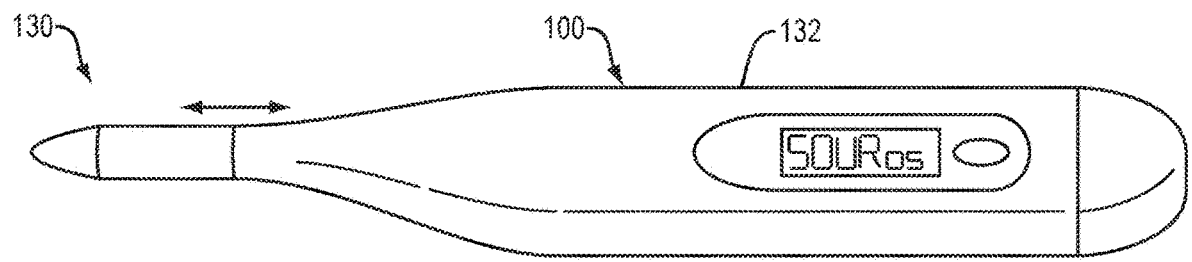
FIG. 4A depicts a handheld device according to an embodiment.

FIG. 4A schematically depicts a handheld device 100 according to an embodiment of the present teachings. Device 100 includes a sensor tip 130 and an analyzer 132, which is in communication with sensor tip 130. While in this embodiment the sensor tip 130 and the analyzer 132 are formed as one integral unit, in other embodiments the sensor tip 130 and the analyzer 132 can be formed as separate devices that communicate with one another. For example, in some embodiments, the sensor tip 130 can transmit data obtained regarding a sample of interest to the analyzer 132 via a wired or wireless connection. In some such embodiments, the sensor tip 130 can communicate with the analyzer 132 wirelessly, e.g., via a plurality of different wireless protocols such as Bluetooth, IEEE 802.11, etc.

In various embodiments, the device 100 can have a variety of different sizes based on the application. By way of example, the device 100 can have a length in a range of about 2 to about 4 inches, and a width in a range of about 0.25 to about 0.5 inches.

Figure 4B:
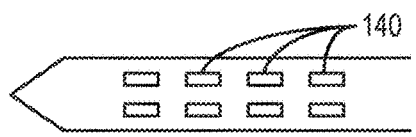
FIG. 4B schematically depicts a sensor tip according to an embodiment.

FIG. 4B further shows a sensor tip according to an embodiment. The sensor tip shown in FIG. 4B includes a plurality of sensing elements 140.

In use, the tip can be exposed to a liquid sample. For example, the tip can be dipped into the liquid sample to draw at least a portion of the sample into the device so as to contact one or more of the sensing elements 140. The sensing elements 140 can then provide signals indicative of the presence and concentration of various species, e.g., molecular species, in the liquid sample. The analyzer 132 can then utilize these measurements in a manner described herein to identify and quantify those species.

Figure 5A:
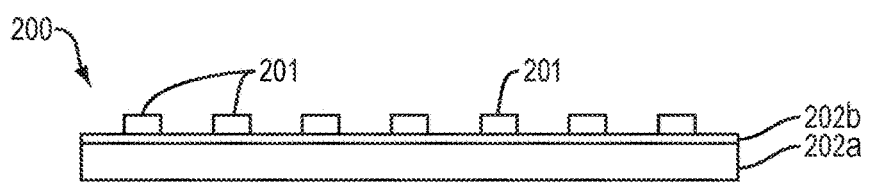
FIG. 5A schematically depicts a sensor device according to an embodiment.

In various embodiments of the present teachings, sensing elements based on fullerenes, e.g., carbon nanotubes, are employed to detect and quantify selected species within a liquid sample. FIG. 5A schematically depicts a sensing device 200 according to an embodiment. Sensing device 200 has a plurality of sensing elements 201. The sensing elements 201 are disposed on an underlying substrate. A variety of materials can be employed for forming the underlying substrate. By way of example, the underlying substrate 202 can include one or more of silicon, silicon-on-insulator (SIMOX) or a variety of other substrates. In the embodiment shown in FIG. 5A, for example, sensing device 200 has an underlying substrate that includes a silicon substrate 202 $a$ with a thin silicon dioxide layer 202 $b$ separating the sensing elements 201 from the silicon substrate 202 $a$.

Figure 5B:
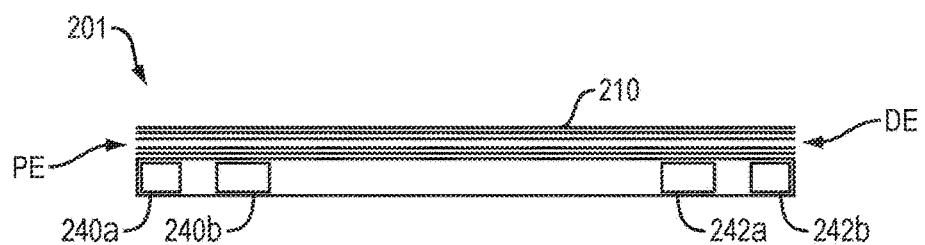
FIG. 5B schematically depicts a sensing element according to an embodiment.

FIG. 5B shows schematics of a sensing element 201 according to some embodiments. Sensing element 201 comprises a plurality of carbon nanotubes 210 (e.g., a mesh of carbon nanotubes) that are disposed on the underlying substrate. Carbon nanotubes 210 extend from a proximal end (PE) to a distal end (DE). In some embodiments, the majority of the carbon nanotubes 210 (and in some cases all of those carbon nanotubes) are single-walled carbon nanotubes (SWCNTs). Some other embodiments use multi-walled carbon nanotubes, or a combination of single-walled and multi-walled carbon nanotubes. In some embodiments, the carbon nanotubes can have a length in a range of 100 nm to about 20 mm.

In FIG. 5B, sensing element 201 includes electrically conductive pads 240 and 242. In particular, two electrically conductive pads 240 $a$ and 240 $b$ are electrically coupled to the proximal end of the carbon nanotubes 210. Two other electrically conductive pads 242 $a$ and 242 $b$ are electrically coupled to the distal end of the carbon nanotubes 210. These pads can allow measuring the impedance of the carbon nanotubes, e.g., the DC electrical resistance of a mesh of carbon nanotubes formed by the plurality of carbon nanotubes 210. By way of example, a current source can be employed to cause the flow of a known current through the carbon nanotubes of a sensor via these pads, and a voltage generated across the carbon nanotubes in response to the current can then be measured. The voltage can be measured via electrical connections of the probes of a voltage measuring device with the electrical pads of a sensor. Such measurements in response to contact of a sample with the carbon nanotubes of a sensor can be employed to identify and quantify selected species within a liquid sample.

In some embodiments, the carbon nanotubes, or other fullerenes, of a sensor can be functionalized so that they can selectively interact with a species of interest, e.g., a molecular species. By way of example, the carbon nanotubes can be functionalized with receptors for glutamate so that the carbon nanotubes can selectively interact with glutamate within a liquid sample.

Figure 6:
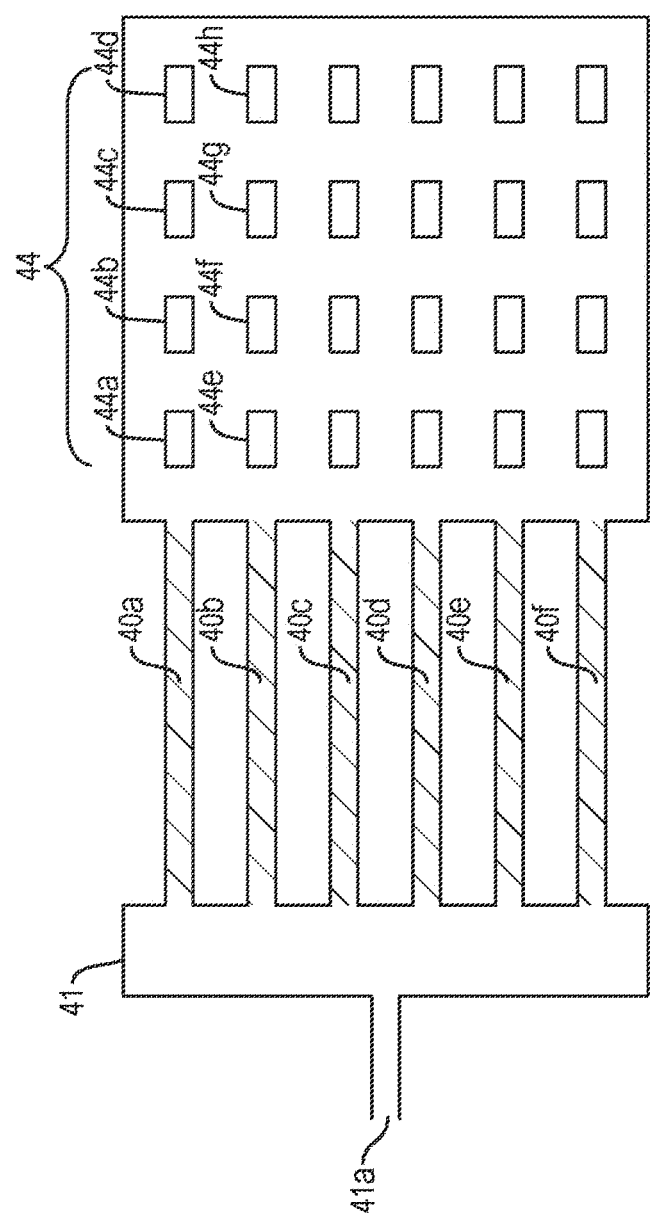
FIG. 6 schematically depicts a device that includes a plurality of filters according to an embodiment, FIG. 7A schematically depicts an analyzer according to an embodiment, FIG. 7B schematically depicts a data acquisition module according to an embodiment, FIG. 8 schematically depicts a data acquisition and analysis system according to an embodiment, FIG. 9 schematically depicts a display of a GUI employed in a device according to an embodiment, FIG. 10 schematically depicts a detection device according to an embodiment, FIG. 11 schematically depicts a detection device according to an embodiment, FIG. 12 schematically depicts an exemplary probe station according to an embodiment, FIG. 13A schematically depicts a detection system according to an embodiment, FIG. 13B schematically depicts an exemplary implementation of the detection system with rotatable wheel according to an embodiment.

In some embodiments, a plurality of filters, e.g., nanofilters, can be employed. The filter can be employed to segregate selected species in a liquid sample from other constituents of the sample and to guide those species to the sensing elements of a device according to the present teachings. By way of example, FIG. 6 schematically depicts such an embodiment. In FIG. 6, a plurality of filters (e.g., nanofilters) 40 $a$, 40 $b$, 40$c$, 40 $d$, 40 $e$, and 40 $f$ (herein collectively referred to as nanofilters 40) are configured to receive a liquid sample via a microfluidic device 41. More specifically, a sample can be delivered to the fluidic device 41 via an input port 41 $a$ thereof. The microfluidic device can then distribute a portion of the sample to each of the nanofilters 40. The passage of the sample portions through the nanofilters may result in a plurality of filtrates, where each filtrate is guided to a selected group of a plurality of sensing elements 44. In this example, the filtrate generated by the nanofilter 40 $a$ is guided to sensors 44 $a$, 44 $b$, 44 $c$, and 44 $d$; and the filtrate generated by the nanofilter 40 $b$ is guided to the sensing elements 44 $e$, 44 $f$, 44 $g$, and 44 $h$. The filtration can be performed based on a variety of different criteria, e.g., molecular weight, mobility, etc. By way of example, one of the nanofilters can segregate sugar molecules from the sample while another can segregate glutamate from the sample. In some embodiments, one or more of the filters can be implemented as liquid chromatography columns (i.e., LC columns).

Figure 7A:
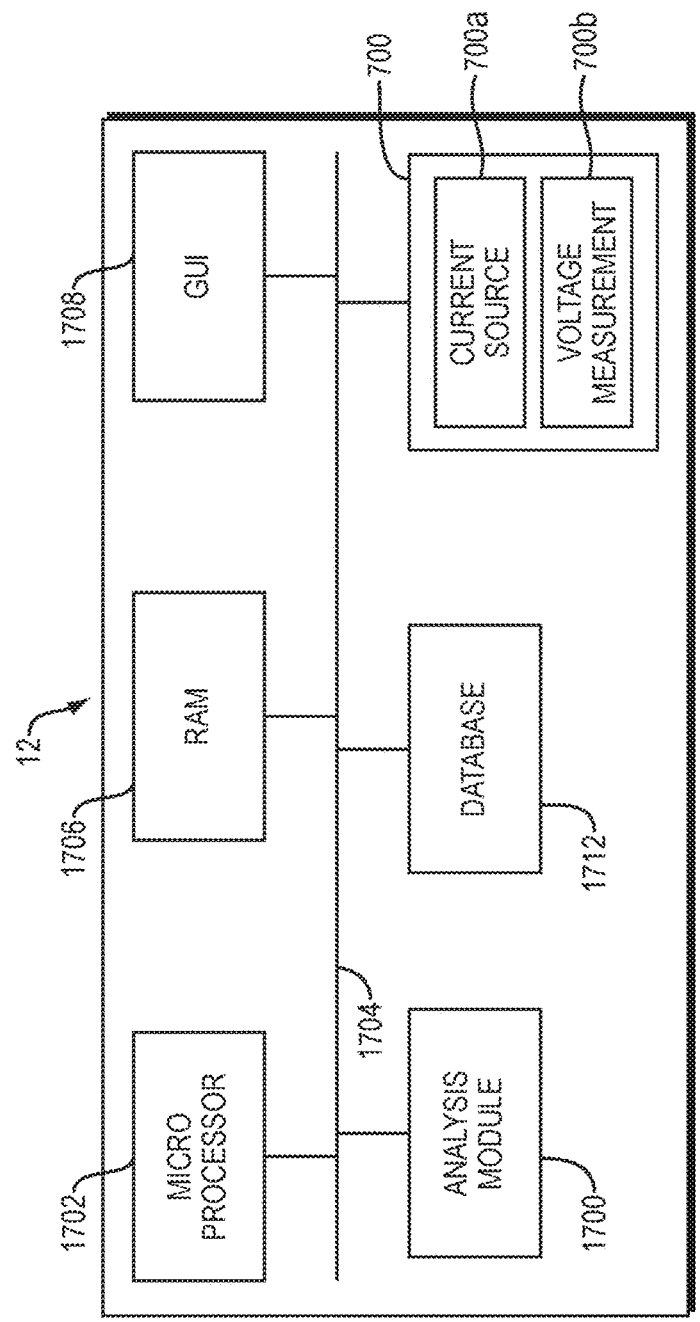

FIG. 7A shows the analyzer 12 according to some embodiments. The analyzer 12 may include a data acquisition unit (herein also referred to as a measurement unit) 700, an analysis module 1700.

The analyzer 12 may further include other components, such as a microprocessor 1702, a bus 1704, a Random Access Memory (RAM) 1706, a Graphical User Interface (GUI) 1708 and a database storage device 1712. The bus 1704 may allow communication among the different components of the analyzer 12. In some embodiments, the analysis module can be implemented in the form of a plurality of instructions stored in the RAM 1706. In other embodiments, it can be implemented as dedicated hardware for performing processing of data obtained by the data acquisition unit 700.

Data acquisition unit 700 may be configured to acquire electrical data from which one or more electrical properties of a sensor (e.g., its DC resistance) can be determined. In this embodiment, the data acquisition unit includes a current source 700 $a$ for supplying electrical currents of selected values to the sensing elements (e.g., to the carbon nanotubes of the sensing elements) and a voltage measuring circuit 700 $b$ that can measure the voltage across each of the sensing elements, e.g., across the carbon nanotubes of each sensing element.

Figure 7B:
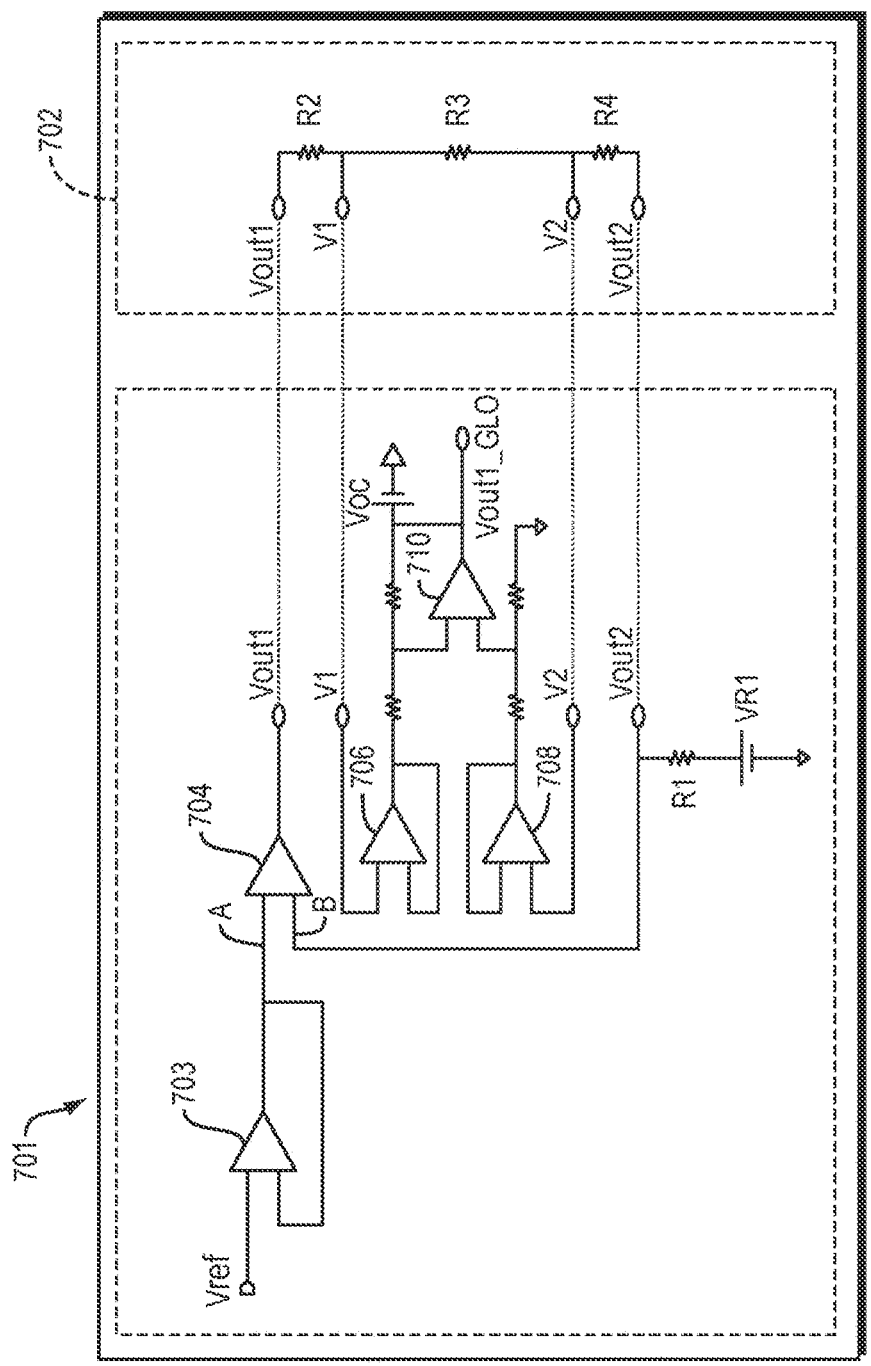

FIG. 7B schematically depicts a voltage measurement circuitry 701 according to some embodiments. Voltage measurement circuitry 701 can be employed as the measurement unit 700 for measuring electrical resistance of a sensor, e.g., sensor 702 that is depicted in this figure as an equivalent circuit diagram of a sensor according to the present teachings. A fixed voltage V (e.g., 1.2 V) is generated at the output of a buffer operational amplifier 703. This voltage is applied to one input (A) of a downstream operational amplifier 704 whose other input B is coupled to VR1 ground via a resister R1. The output of the operational amplifier 704(Vout1) is coupled to one end of the sensor 702 and the non-connected to VR1 end of the resistor R1 is coupled to the other end of the sensor 702 (in this schematic diagram, resistor R2 denotes the resistance between two electrode pads at one end of a sensor, resister R3 denotes the resistance of the nanotubes of a sensor extending between two inner electrode pads of the sensor, and resistor R4 denotes the resistance between two electrode pads at the other end of the sensor).

As the operational amplifier maintains the voltage at the non-connected to VR1 end of the resistor R1 at the fixed voltage applied to its input (A), e.g., 1.2 V, a constant current source is generated that provides a constant current flow through the sensor 702 and returns to ground via the resistor R1 and VR1.

The voltage generated across the nanotubes of the sensor is measured via the two inner electrodes of the sensor. Specifically, one pair of the inner electrode pads is coupled to a buffer operational amplifier 706 and the other pair is coupled to the other buffer operational amplifier 708. The outputs of the buffer operational amplifiers are applied to the input ports of a differential amplifier 710 whose output port provides the voltage difference across the carbon nanotubes of the sensor. This voltage difference (Vout1_GLO) can then be used to measure the resistance exhibited by the sensor. The current forced through R3 is set by I=(Vref−VR1)/R1. The value of VR1 is digitally controlled. For each value of current I, the corresponding voltage (Vout1_GLO) is measured and stored. The resistance of the sensor may be different at any given current so it is calculated as derivative of voltage, Vout1_GLO, with respect to current I, i.e., $R = dV/dI \approx \Delta V/\Delta I$ using the stored voltage versus I. If the sensor has linear constant resistance, the value of R can be found as $R = dV/dI \approx \Delta V/\Delta I = V/I$.

Referring back to FIG. 7A, the analysis module 1700 can be configured to receive the current and voltage values generated and obtained by the measurement unit 700 and can process these values according to the present teachings. The analysis may identify and quantify selected species, e.g., molecular species, present in a liquid sample. Different units in the analyzer 12, as well as other units of the analysis module, can operate under the control of the microprocessor 1702.

By way of example, as discussed in more detail below, in some cases, the analysis of a liquid sample is directed to the identification and quantification of the species that are primarily responsible for the "taste" of a liquid food sample.

For example, in some embodiments, the analysis unit employs the values of currents and voltages that it receives from the measurement unit for a sensor and calculates the change in one or more electrical properties of the carbon nanotubes (or other sensing elements) of that sensor in response to interaction with a liquid sample. For example, the analysis module can calculate a change in the DC electrical resistance and/or AC electrical impedance of the carbon nanotubes. The change can be calculated relative to calibrated values of such electrical properties obtained in absence of the liquid sample. The calibration can be done once or can be performed for each measurement session.

The analysis module can then correlate the calculated change in one or more electrical properties of the sensor, exhibited in response to interaction of the liquid sample, with a particular species of interest in the sample. For example, the analysis unit can utilize the calculated change in one or more electrical properties of the sensor to identify and quantify sugar molecules in the sample. By way of example, the analysis unit can compare the change in the electrical properties with a plurality of calibrated values of change previously obtained for selected species, e.g., polysaccharides and stored in a database 1712, to determine whether a particular species is present in the sample, and if so, at what concentration.

While in some embodiments, the various functional modules or components of, the analyzer 12, such as the analysis module 1700, and the database 1712 can be integrated within a single device, in other embodiments, one or more of the modules, e.g., the analysis module 1700 and/or the database 1712, can be provided on a server (e.g., remote server), which can communicate other modules of the analyzer via a network, e.g., the Internet.

Figure 8:
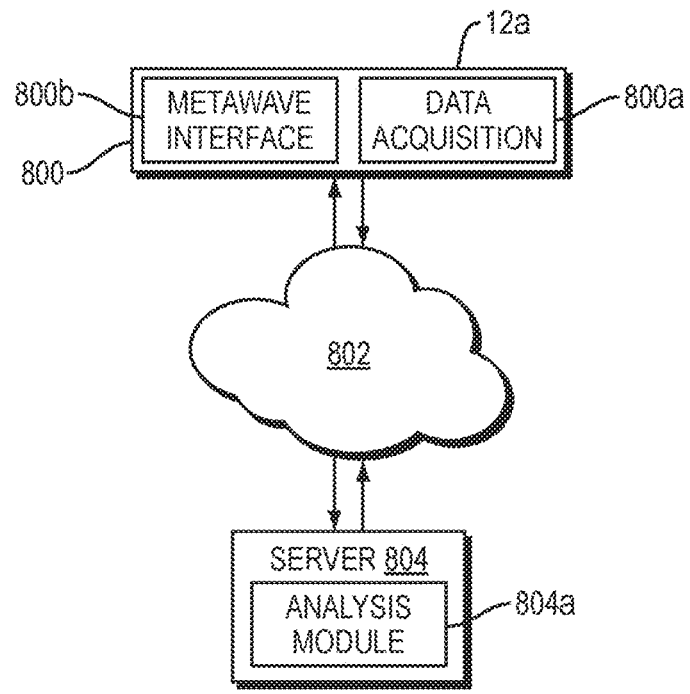

By way of example, FIG. 8 schematically depicts a data acquisition and analysis system according to an embodiment. The system of FIG. 8 includes a device 800 that comprises a data acquisition module 800 *a* for receiving electrical data from a sensor according to the present teachings (not shown in this figure). Device 800 has a network interface 800 *b*. Moreover, the system of FIG. 8 includes a network 802, e.g., the Internet. Through network interface 800 *b* and network 802, device 800 communicates with a server 804. Server 804 may have an analysis module, which can receive the data transmitted by the device 800, process that data according to the present teachings, and transmit the analysis results back to the device 800.

Figure 9:
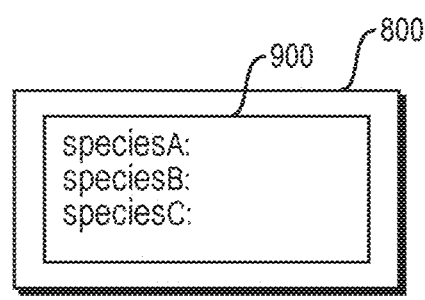

With reference to FIG. 9, in some embodiments, such a device 800 can include a graphical user interface (GUI) 900 for displaying the analysis results to a user. Alternatively or in addition, the server 804 can transmit the analysis results to a user's mobile device that executes an application for presenting the analysis results to a user.

In some embodiments, the analysis results generated by the analysis unit can be stored in a database, such as database 1712 of FIG. 7A, or another database. In some embodiments, the database can store calibration data regarding the signature of certain compounds obtained by employing the teachings of the present disclosure. For example, in some embodiments, the modulation of one or more electrical properties (e.g., DC electrical resistance) of a sensing element according to the present teachings in response to contact with a species (e.g., glucose molecules) can be obtained and stored in the database as the signature of glucose. This signature can then be utilized for identifying and quantifying glucose molecules in a sample under study.

As noted above, in some embodiments, the sensors can comprise multiple groups, where one group is configured, e.g., via functionalization, to be primarily sensitive to one, or several, molecular species. For example, a group of sensors can be configured to be primarily sensitive to polysaccharides. In such a case, the measurement module can transmit the measured results together with information indicating the sensor (or sensors) from which the results were obtained to the analysis module.

As noted above, in some embodiments, the present teachings are employed to determine the "taste" of a liquid food sample. In such embodiments, the analysis module is configured to identify and quantify the species that are primarily responsible for the sensation of taste. In some embodiments, the analysis module can be further configured to assign a "taste score" to the liquid sample based on calculated concentrations of these species.

The five basic tastes comprise sweetness, bitterness (or pungency), saltiness, sourness, and umami. Although pungency is a heat sensation, rather than a taste sensation, it is typically included in the five basic tastes due to its importance in the subjective sensation of taste. Table 1 below lists a number of chemical compounds that can contribute to the sensation of particular taste

TABLE 1

| Item | Taste | Material | Natural Source |
|------|-------|----------|----------------|
| 1 | Pungency | Capsacin | Pepper |
| 2 | Sweetness | Glucose | Fruits, Sugar, Drinks |

TABLE 1-continued

| Item | Taste | Material | Natural Source |
|---|---|---|---|
| 3 | | Fructose | Fruits |
| 4 | | Sucrose | Sugar |
| 5 | Umami | Glutamic acid | Meat, Soy sauce |
| 6 | Saltiness | Sodium chloride | Salt |
| 7 | | Potassium chloride | Synthetic salt |
| 8 | Sourness | Acetic acid | Vinegar |
| 9 | | Citric acid | Lemon juice |
| 10 | | Malic acid | |

In some embodiments, a device according to the present teachings can detect and quantify the above compounds in a sample, e.g., food sample, according to the present teachings.

Figure 10:
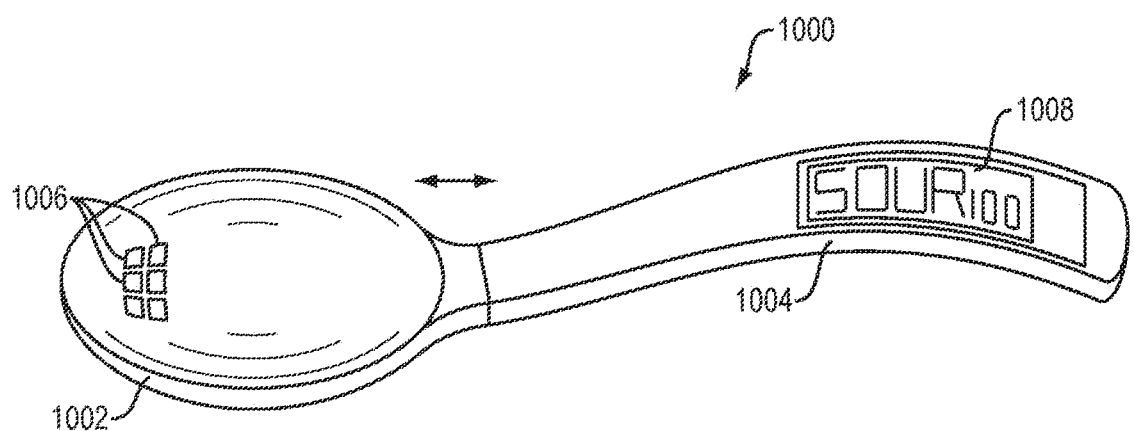

The teachings of the disclosure are not limited to the embodiments discussed above, but can be implemented in a variety of different ways. For example, with reference to FIG. 10, in another embodiment, a detection device according to the teachings of the disclosure can be in the form of a spoon 1000 having a bowl portion 1002 and a handle 1004 extending from the bowl portion 1002. The bowl portion provides a depression configured to receive a liquid sample. A plurality of sensors 1006 according to the present teachings can be incorporated in the bowl portion 1002. In this embodiment, the sensors 1006 are incorporated in the bowl portion substantially in proximity of its tip. In other embodiments, the sensors can be distributed differently along the bowl portion. The sensors 1006 are in communication with an analyzer (not shown), which is incorporated in the handle 1004. The analyzer is configured to receive data (such as electrical data) from the sensors in response to the interaction (e.g., contact) of the sensors with species within the liquid sample received in the bowl portion. The analyzer can analyze, e.g., in a manner discussed above in connection with analyzer 12, the received data in order to identify and quantify selected species within the liquid sample. In this embodiment, the spoon 1000 includes a GUI having a display 1008 incorporated within the handle 1004, which can present the results of the analysis of the liquid sample to a user. For example, the GUI can display the concentration of selected species in the liquid sample, e.g., one or more species responsible for the taste of a liquid sample, to a user.

Figure 11:
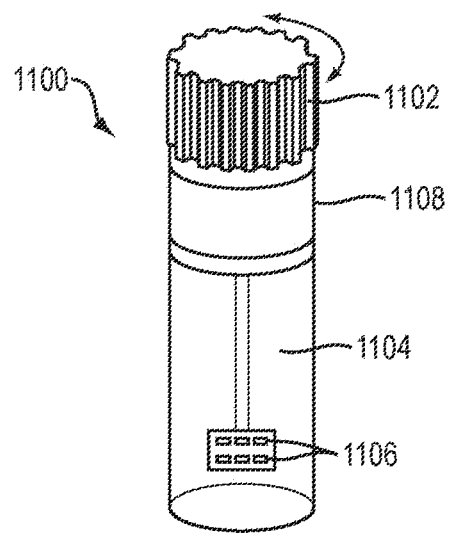

FIG. 11 schematically presents yet another embodiment of a detection device 1100 according to the present teachings. The device 1100 includes a container 1101 (e.g., a vial) for receiving a liquid sample. The device 1100 further includes a cap 1102 and an arm 1104, which extends from a proximal end, coupled to the cap, to a distal end at which a plurality of sensors 1106 is disposed. The cap 1102 can engage with the container so as to place the sensors within the liquid sample. In some embodiments, a measurement module, such as the measurement module discussed above, can be incorporated in the cap, which can measure the response of the sensors to one or more species in the liquid sample. In some embodiments, a plurality of transmission media (e.g., wires) can extend from the sensors to the measurement unit to transfer electrical data thereto. In some embodiments, such transmission media can be disposed on the surface of the arm 1104, or alternatively, incorporated within an internal channel provided in the arm extending from the sensors to the measurement unit.

In some embodiments, a communications interface (e.g., a wireless communication interface) incorporated in the cap 1102 can transmit the measurement data to a remote analysis unit (e.g., a remote server such as that shown in FIG. 8 for analysis). As discussed above, in some embodiments, the analysis unit can be running on a remote server. Alternatively, the analysis unit can be incorporated in the cap 1102 so as to operate on the measurement data generated by the measurement unit. A display 1008 incorporated operated by a GUI can present the analysis results to a user.

A plurality of materials and techniques can be employed to fabricate a sensor according to the present teachings. In one approach, a thin silicon dioxide (SiO2) layer (e.g., a layer having a thickness in a range of about 100 nm to about 200 nm) can be formed on an underlying silicon substrate (e.g., via thermal oxidation). Subsequently, graphene and/or carbon nanotubes can be printed onto the silicon dioxide layer. On each end of the printed line, one or more (typically two) metal electrodes can be formed (e.g., via vapor deposition) to facilitate electrical coupling to the carbon nanotube mesh and/or graphene layers. In some embodiments, a plurality of such sensors can be formed on the underlying substrate.

In some embodiments, the fullerene-based sensing element of a sensor according to the present teachings can be formed by depositing a layer of graphene oxide on an underlying substrate, e.g., a SiO2 coated silicon substrate. The graphene oxide layer can then be exposed to radiation to form a graphene layer.

In one application, the teachings of the present teachings can be employed to detect and quantify gluten in a food sample. It is known in the art that gluten is a protein composite that can be found in wheat or other grains, such as barley and rye. As the number of individuals with gluten allergy increases, especially in North America, there is an increased interest in reliable and efficient methods for detecting gluten in food samples. In general, gluten refers to a family of composite proteins, which includes primarily Prolamins and Glutenins. In many food samples, these two categories of storage proteins are binded by starch molecular strands. The proteins in the Prolamins category include gliadin (wheat), hordein (barley), secalin (rye), zein (corn), kaffrin (sorghum), and avanin (oat). The molecular weight of these proteins varies from about 10 KDa to about 90 KDa.

In some embodiments, one or more of these proteins are identified, and optionally quantified, in a food sample. In some such embodiments, the food sample is dissolved in an alcohol (e.g., ethanol) and the alcohol solution is passed through one or more filters (e.g., micro liquid chromatography columns) to generate a filtrate containing one or more of the above gluten proteins. The filtrate is then allowed to contact with a sensing element according to the present teachings. The change in an electric property of the sensing element (e.g., the DC resistance and/or AC impedance of the carbon nanotubes of the sensing element) is measured and analyzed to determine whether one or more of the above gluten proteins are present in the food sample. By way of example, a temporal variation of DC resistance of the sensing element can be analyzed by reference to previously-determined respective responses of the sensing element to all or a subset of the above gluten proteins to identify one or more of these proteins in a food sample. A Principal Components Analysis (PCA) in which the previously-determined responses are employed as the basis vectors can be employed to identify (and optionally quantify) one or more of the above gluten proteins in a food sample.

In some embodiments, the fullerenes (e.g., carbon nanotubes) of a sensing element can be functionalized with an antibody that can selectively bind to one of the above gluten proteins. When a liquid sample (e.g., a sample of food dissolved in alcohol) is introduced to onto the sensing element, the gluten protein that can selectively bind to the functionalized fullerenes (e.g., functionalized carbon nanotubes) via the antibody. Such binding of the protein to the functionalized carbon nanotubes (or other fullerenes) of the sensing element can modify one or more electrical properties (e.g., DC resistance) of the functionalized carbon nanotubes. The change in the electrical property of the carbon nanotubes can then be detected and analyzed to determine the presence of that protein in the food sample. By way of example, the carbon nanotubes of a sensing element can be functionalized with G12 antibodies, which can selectively bind to gliadin protein, e.g., 33-mer of the gliadin protein (hexapeptide sequence QPQLPY), and similar peptides in the Prolamins. In some embodiments, different groups of sensing elements are functionalized with different antibodies, where each antibody can bind to a different one (or a different group) of the above gluten antibodies. In this manner, in some embodiments, a device according to the present teachings can detect concurrently a plurality of different gluten proteins present in a food sample.

Figure 13A:
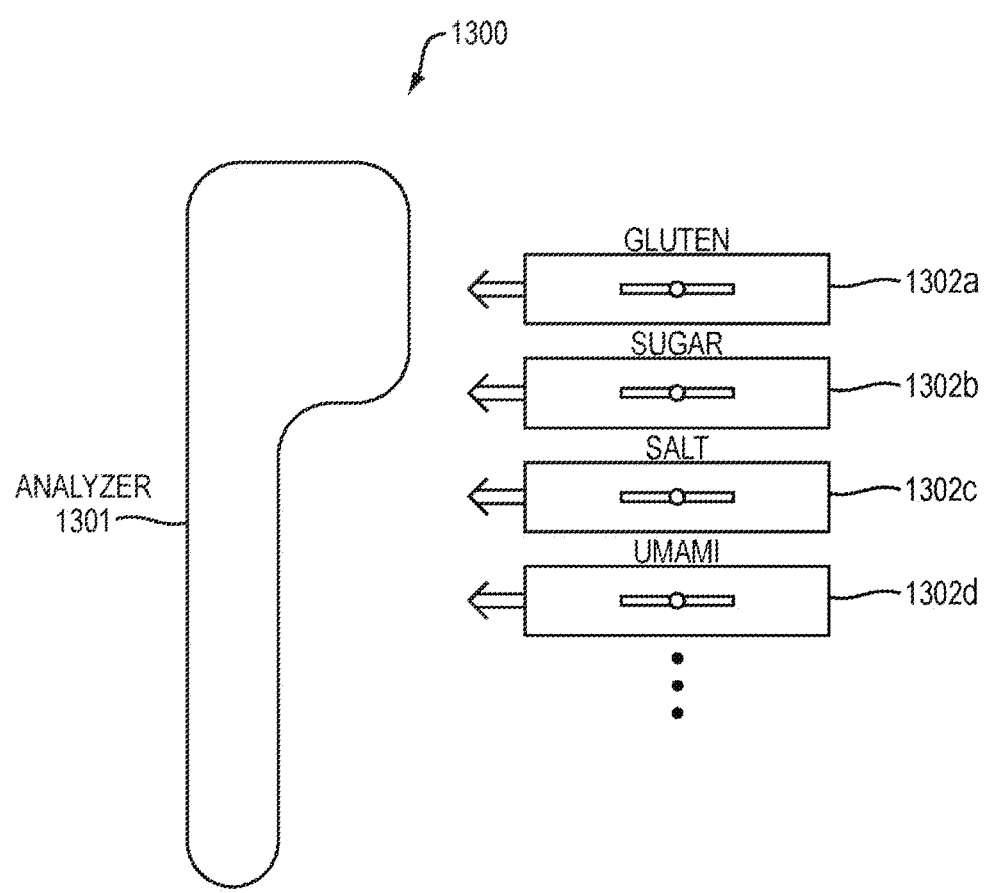

By way of further illustration, FIG. 13A schematically depicts a detection system 1300 according to another embodiment. System 1300 includes an analyzer 1301 and a plurality of cartridges 1302 a, 1302 b, 1302 c, 1302 d, etc. (herein referred to collectively as cartridges 1302). Each of the cartridges 1302 includes one or more sensing elements (such as sensing element 1303 a, 1303 b, 1303 c, 1303 d, etc.), such as those discussed above. The sensing element may be further configured (for example, via functionalization or otherwise) to be primarily responsive to a particular species of interest. For example, in this embodiment, the cartridge 1302 a can be used to detect (and optionally quantify) gluten in a sample while the cartridges 1302 b, 1302 c and 1302 d can be utilized, respectively, for detecting sugar, salt, umami, etc.

In use, a sample (e.g., a liquid sample) can be introduced into one of the cartridges 1302 (e.g., using one of the methods discussed above). The cartridge can then be removably coupled to the analyzer 1301 (e.g., via an inlet) to identify and optionally quantify (if present) the species of interest.

Figure 13B:
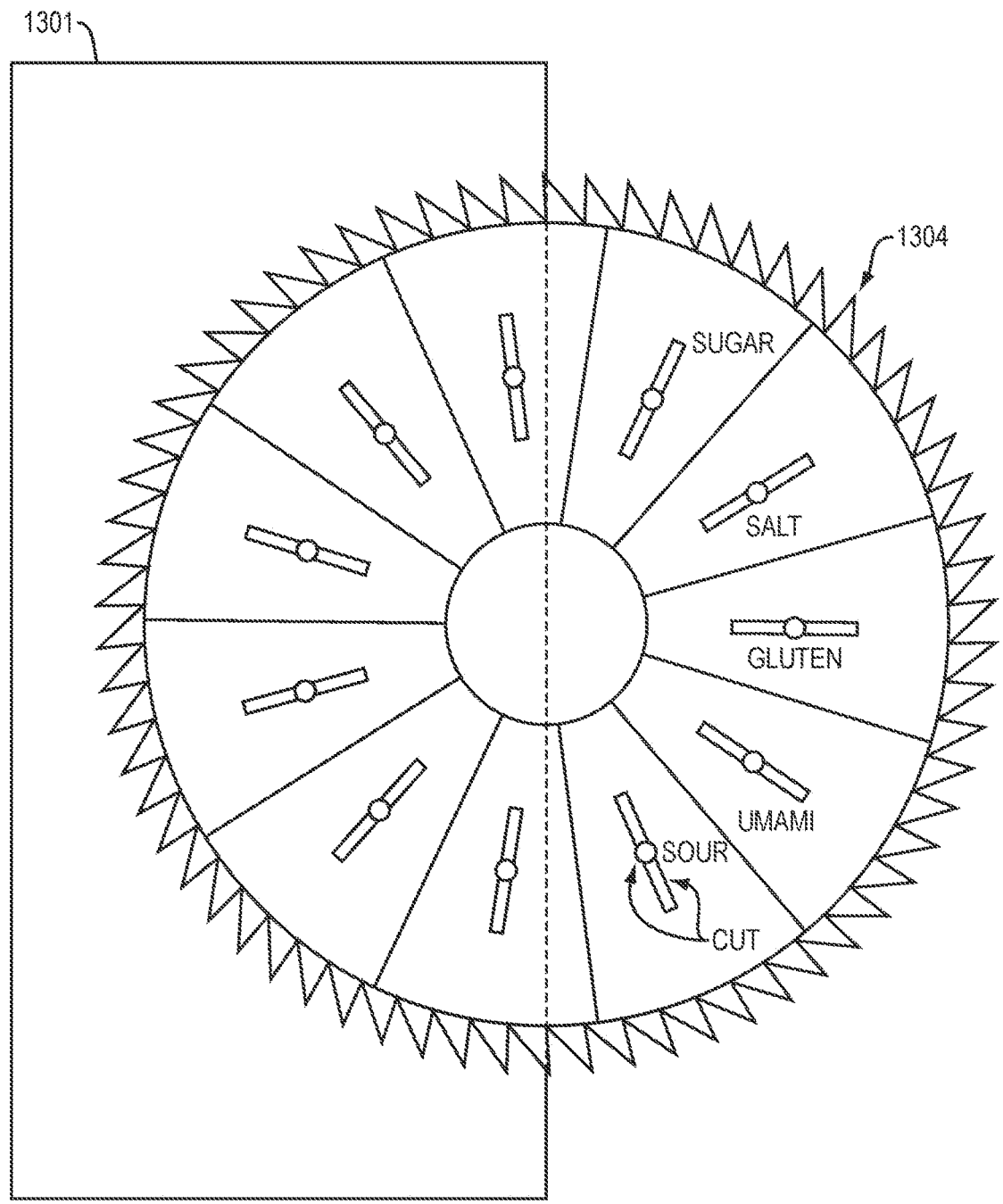

FIG. 13B schematically depicts an exemplary implementation of the detection system 1300 according to another embodiments. In FIG. 13B, the cartridges 1302 are arranged as a wheel 1304 that can be rotatably coupled to the analyzer 1301. By rotating the wheel one or more of the cartridges 1302 onto which one or more samples under study have been introduced can be coupled into the analyzer 1301. The analyzer 1301 can then interrogate the sensing elements of the one or more cartridges, e.g., in a manner discussed above in connection with the previous embodiments, to identify and optionally quantify the species of interest.

The following Examples are provided for further illustration of various aspects of the present teachings and are not intended to necessarily indicate the optimal ways of practicing the disclosure or the optimal results that can be obtained.

Examples

Figure 14A:
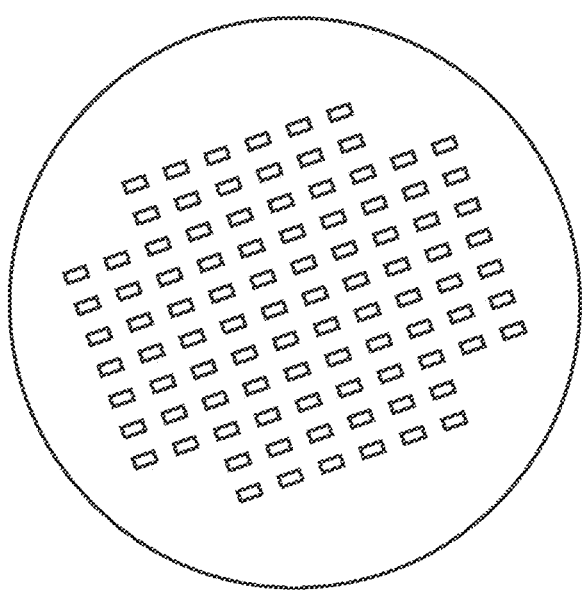
FIG. 14A is an image of a prototype sensor unit fabricated according to the present teachings.

FIG. 14A shows an image of a prototype sensor unit according to the present teachings. The sensor unit includes a plurality of sensors (herein also referred to as sensing elements) according to the present teachings that are disposed on an underlying silicon substrate. A layer of silicon dioxide is present between the underlying substrate and the sensors. Each sensor comprises a plurality of single walled carbon nanotubes, which form a mesh and extend between two pairs of metal pads, which can be used for measuring electrical properties of the nanotubes as discussed below.

Each sensor was fabricated by coating the substrate with mono/multi-layer carbon nanotubes (SWCNT) with a thickness of 20 microns and a maximum line length of 20 mm. Specifically, for each sensor, the CNT layers were printed as a line on the underlying silicon oxide coating of the silicon wafer. On both ends of the printed line, two electrodes of Chromium/Palladium (Cr/Pd) were formed by vapor deposition method to facilitate measuring the electrical resistance of the printed nanostructures in response to exposure to a number of chemical compounds. The thickness of the Cr/Pd electrodes was about 150 nm.

More specifically, a silicon dioxide layer was formed in a silicon substrate by oxidizing the substrate. A photoresist layer was then deposited on the silicon oxide layer. The deposited photoresist layer was then patterned. Metal was then deposited on the patterned layer to form the aforementioned metal electrodes. The photoresist was then removed (washed). Carbon nanotubes were then printed as one or more lines between the metal electrodes to generate a plurality of sensors. Subsequently, another photoresist layer was spin-coated on the substrate and then patterned to provide circular access ports to the carbon nanotubes of each sensor.

Figure 14B:
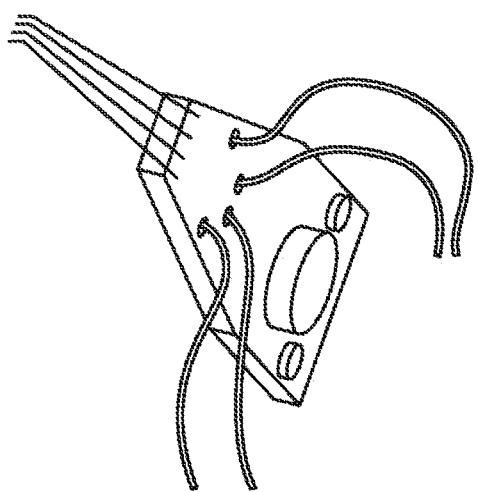
FIG. 14B is an image of a four-point probe used for making measurements shown in FIGS. 15A-15G, according to some embodiments.

The four point measurement method was used for performing resistance measurements in order to eliminate the effects of contact resistances and wire resistances. FIG. 14B shows a four-point probe that was employed to measure the electrical characteristics of the sensing elements of the sensor unit shown in FIG. 14A.

For measurement consistency, a layer of a photoresist material was added to the assembly via spin coating to avoid any electrical short contacts and to limit the exposure of chemical solutions under study to the access circle of 2 mm diameter.

Figure 12:
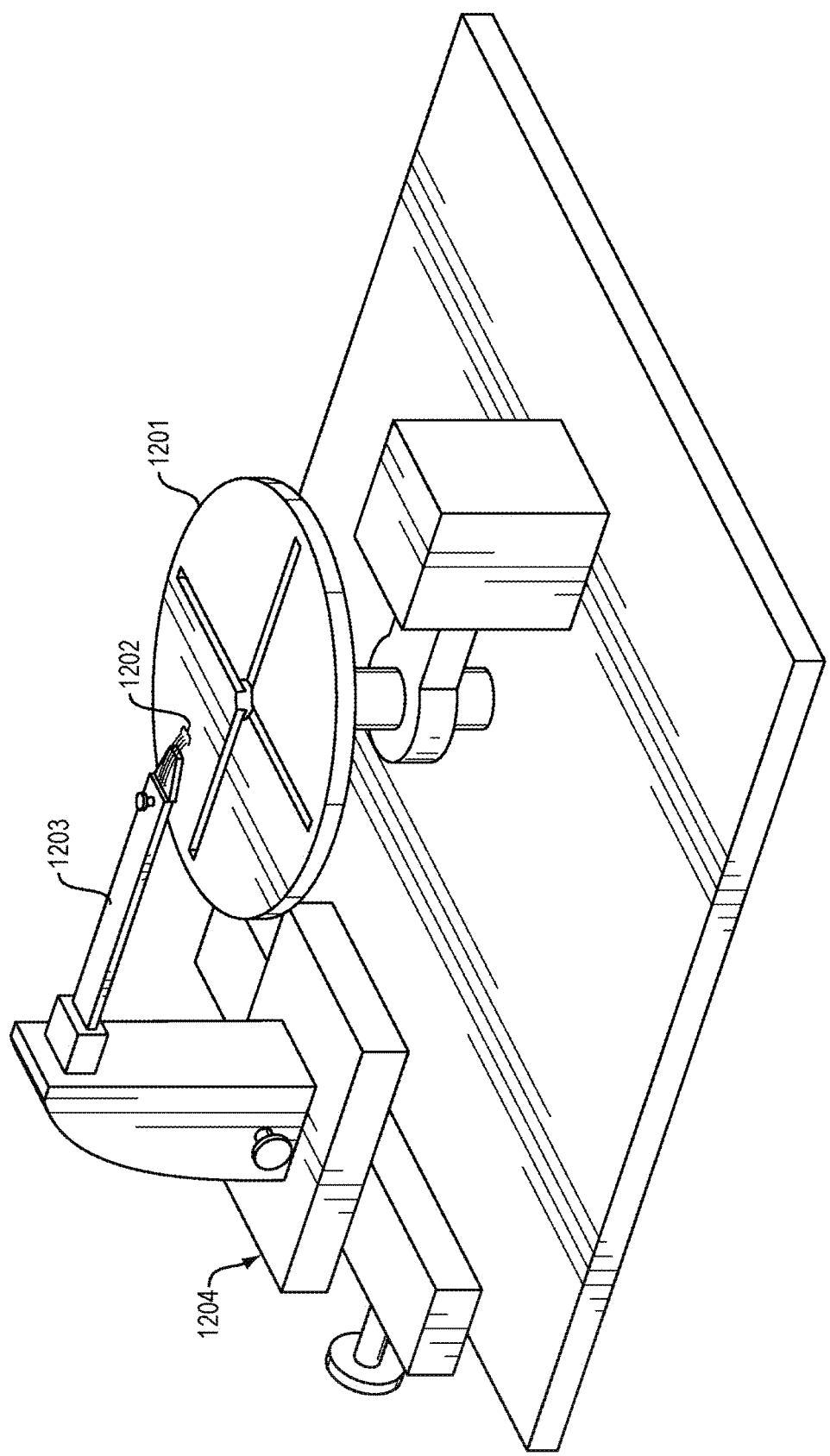

A customized probe station was designed and assembled to facilitate performing the measurements on the specific pattern of the sensors on the underlying wafer. As shown in FIG. 12, the probe station included a platform 1201 for mounting the substrate via vacuum suction. The probe station further included a plurality of multi-contact DC probes 1202 that were coupled to an arm 1203. The arm 1203 in turn was attached to an xyz translation stage 1204 to allow positioning the probes in register with a desired sensor. To perform electrical measurements, the DC probes were then brought into Ohmic contact with the respective pad electrodes.

Figure 15A:
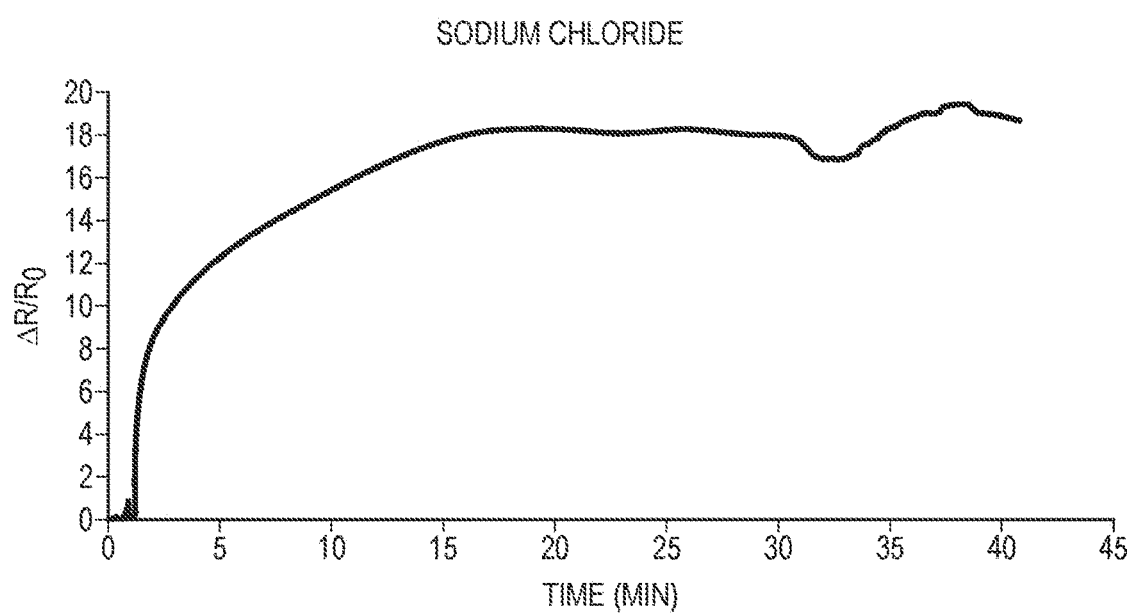
FIGS. 15A-15G show exemplary data obtained for a variety of different compounds according to some embodiments.
Figure 15B:
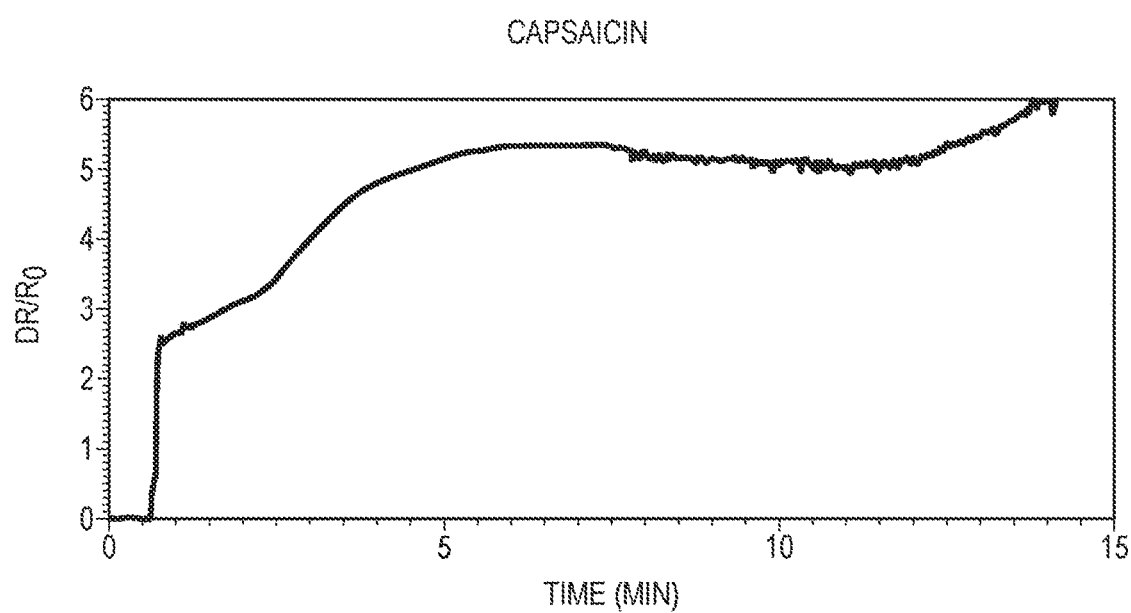
Figure 15C:
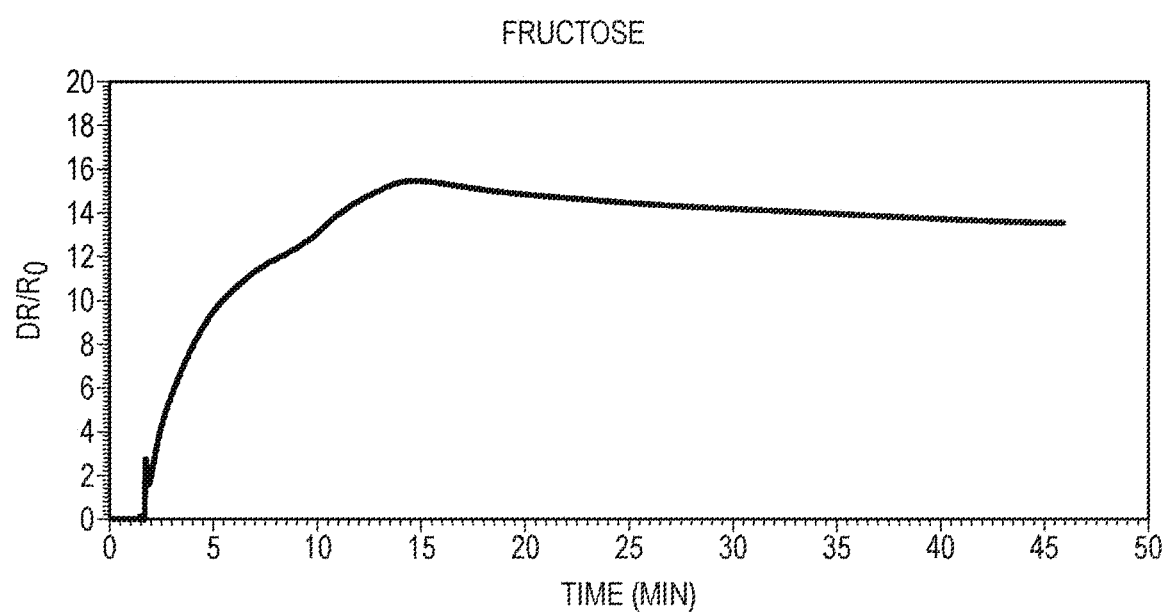
Figure 15D:
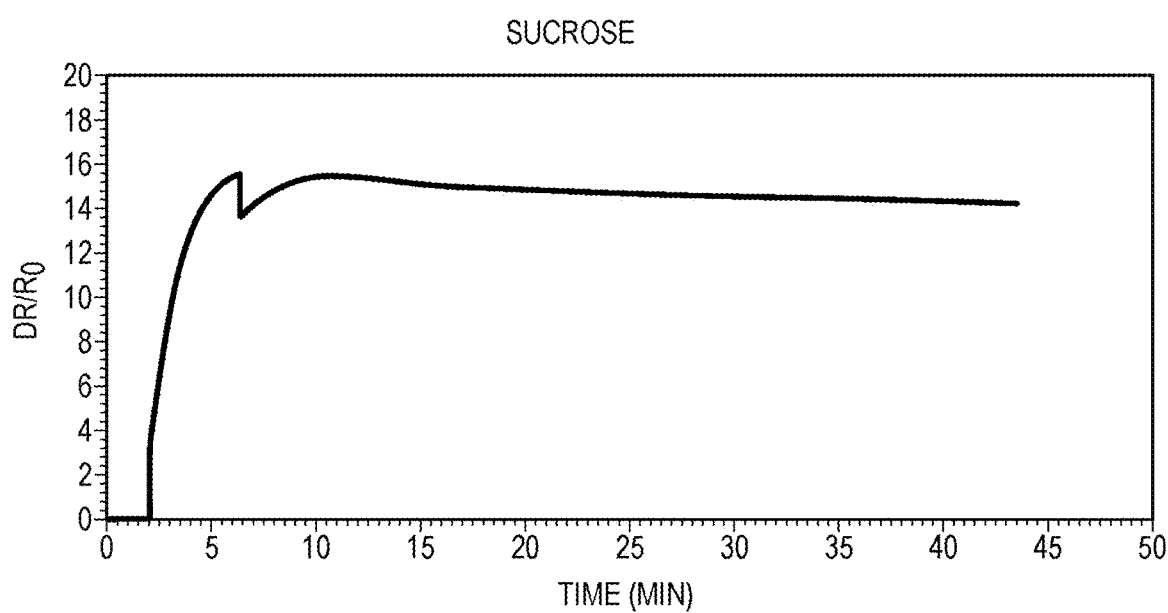
Figure 15E:
Figure 15F:
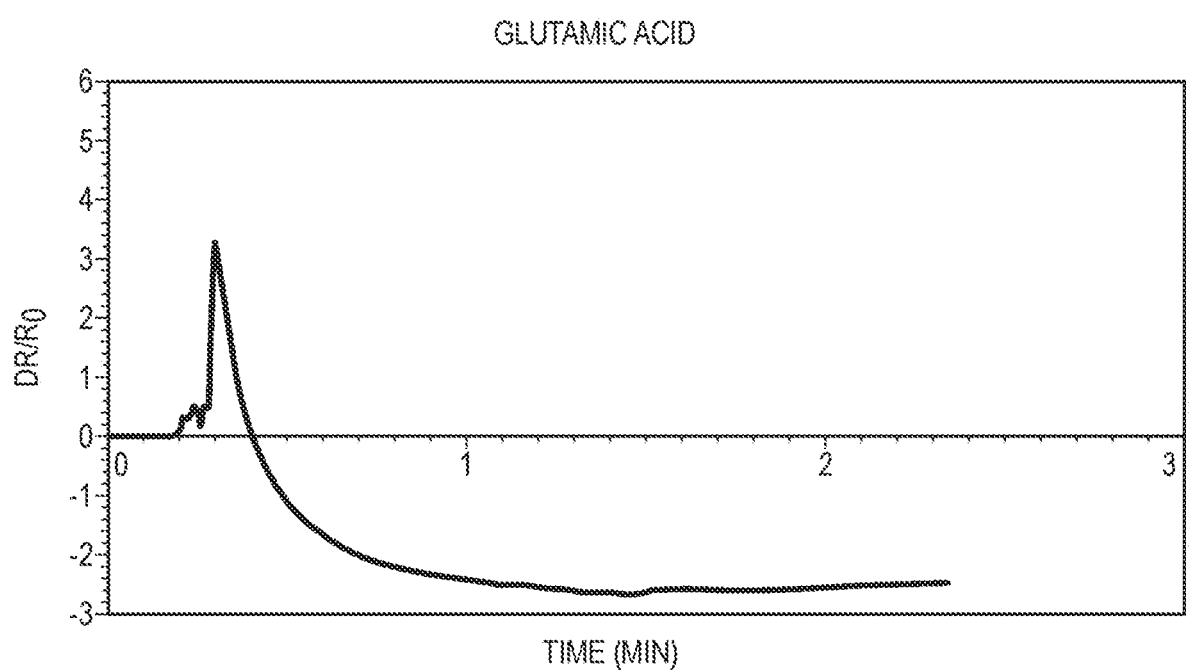
Figure 15G:
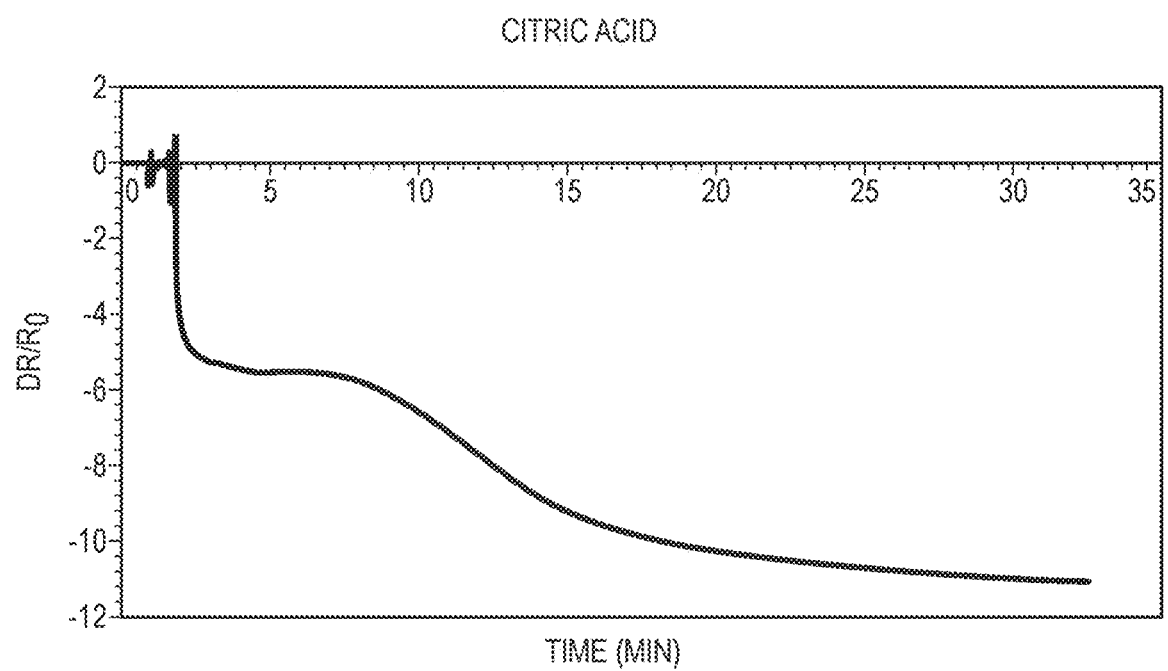

FIG. 15A-15G show graphs of data collected for the performance of the sensing elements according to some embodiments. The graphs show data corresponding to temporal changes in the DC resistance of sensing elements of the prototype sensor unit when exposed to a plurality of different compounds. In the graphs, the horizontal axis shows time and the vertical axis show relative change in resistance ($\Delta R/R0$) measured in percentage. Specifically, FIG. 15A shows the change in the resistance of a sensing element as a function of time when an aqueous solution of sodium chloride with an approximate molarity of 1 was introduced to the sensing element. FIG. 15B shows resistance data obtained by introducing an aqueous solution of capsaicin at an approximate molarity of $6.5 \times 10-5$ to another sensing element. FIG. 15C shows resistance data obtained by introducing an aqueous solution of fructose at an approximate molarity of 1 to a sensing element. FIG. 15D shows resistance data obtained by introducing an aqueous solution of sucrose at an approximate molarity of 1 to a sensing element. FIG. 15E shows resistance data obtained by introducing an aqueous solution of glucose at an approximate molarity of 1 to a sensing element. FIG. 15F shows resistance data obtained by introducing an aqueous solution of glutamic acid at an approximate molarity of 6.8 to a sensing element. FIG. 15G shows resistance data obtained by introducing an aqueous solution of citric acid at an approximate molarity of 1 to a sensing element. Table 2 shows in more detail the specifics of the solutions used to derive the data shown in FIGS. 15A-15G.

TABLE 2

| | Molecular Mass | Volume | Weight | |
|---|---|---|---|---|
| | g/mol | ml | g | Molar |
| Sodium Chloride | 58.44 | 5 | 0.2922 | 1 |
| Capsasin | 305.41 | 50 | 0.001 | 6.54857E−05 |
| Fructose | 180.16 | 5 | 0.9008 | 1 |
| Sucrose | 342.2965 | 5 | 1.71148 | 0.999998539 |
| Glucose | 180.1559 | 5 | 0.90078 | 1 |
| Glutamic Acid | 147.13 | 5 | 5 | 6.796710392 |
| Citric Acid | 192.12 | 5 | 0.9606 | 1 |

The above data indicates that, according to some embodiments, the interaction of the tested compounds with the sensing elements provides unique signatures for identifying the compounds. In particular, the temporal variation of the resistance exhibited for one compound is different from the respective temporal variation exhibited for another compound. Such differences can be employed to uniquely identify the compounds in a sample under study. For example, in some embodiments, such analysis can be facilitated by obtaining the Fourier transform of the time variation of resistance of each compound. The Fourier transform can provide unique spectral signatures for the compounds.

In some embodiments, a device according to the present teachings can be implemented as a wearable device that can be removably and replaceably attached to a body part or clothing.

By way of example, FIG. 16A depicts a wearable detection device 1600 according to an embodiment of the present teachings for chemical analysis of a food sample. The device 1600 includes a flexible member 1602 in the form of a wrist band that allows a user to wear the device similar to a watch. The wrist band includes a fastening element 1604, e.g., a clip or a hook-and-loop element, for removably and replaceably securing it to a user's wrist. The wrist band can be made of a variety of different materials such as leather, plastic, etc.

The wearable device 1600 includes an analyzer 1606 that is mechanically coupled to the wrist band. As discussed in more detail below, the analyzer 1606 can be used to determine whether a chemical species of interest is present in a sample, e.g., a food sample, and optionally quantify the concentration of that species in the food sample.

In other embodiments, a wearable device according to the present teachings can be secured to another body part, e.g., a user's arm, or even to a user's clothing. By way of example, FIGS. 17A and 17B schematically depict a wearable detection device 1700 according to another embodiment. Device 1700 includes an analyzer 1702 for analyzing a food sample, e.g., in a manner discussed below. Device 1700 further includes a clip 1704 for removably and replaceably securing device 1700 to clothing or other places. In this embodiment, the analyzer 1702 includes a display 1706 for presenting the results of the food analysis to a user.

Referring back to FIG. 16A, the exemplary analyzer 1606 includes a lid 1606 a that is hingedly coupled to a casing 1606 b. A user can open the lid 1606 a to access a cavity 1608 provided in the casing 1606 b within which a cartridge, such as cartridge 1900 shown in FIG. 19, can be removably and replaceably engaged. The casing 1606 b further provides housing for circuitry adapted to receive and analyze electrical signals. The electrical signals may be associated with a change in one or more electrical properties of one or more sensors that are disposed in the cartridge. The change may result in response to interaction with a food sample, as further discussed in more detail below.

As shown in FIG. 16B, in this embodiment, the analyzer 1606 includes a display 1610 in the analyzer's lid, which can present the results of a chemical analysis of a food sample to a user. In other embodiments, the analyzer may not include such a display. Rather, the analyzer can send the results of chemical analysis of a food sample to a user's device, e.g., a mobile device, for presentation to the user.

Figure 18:
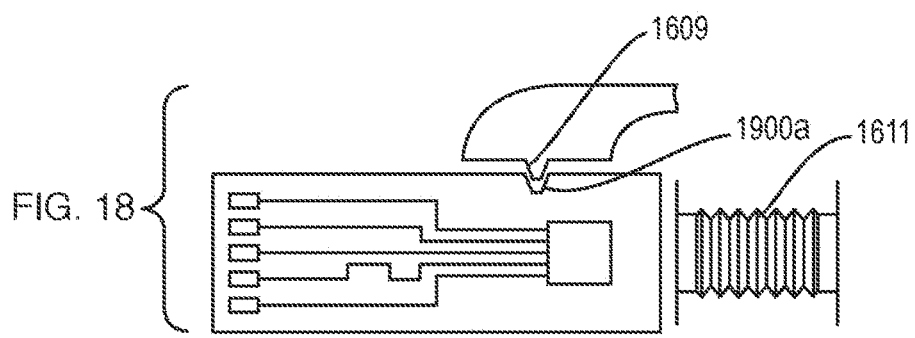
FIG. 18 depicts a mechanism for securing a cartridge in a cavity according to an embodiment.

More specifically, the cartridge 1900 can be inserted into the cavity 1608 of the analyzer 1606 via an aperture 1608 a thereof and secured in place via a plurality of mechanisms. One example of such a mechanism is depicted with reference to FIG. 18. As the cartridge 1900 is advanced into cavity 1608, it pushes against a spring 1611 provided in the distal end of the cavity. Moreover, a pin 1609 in a sidewall of the cavity 1608 can engage with a notch 1900 a provided on a side surface of the cartridge 1900 to secure the cartridge 1900 in place.

Other mechanisms can also be employed for securely engaging the cartridge within the cavity. For example, in some embodiments the cavity can include a plurality of protruding spring-loaded pins (not shown). The bottom surface of the cartridge can, in turn, include a plurality of receptacles (sockets) for engaging with the pins when the cartridge is disposed within the cavity.

Referring again to FIG. 16A, a tab or a button 1612 provided in the casing can be utilized to disengage the pin from the notch, thereby releasing the cartridge for removal from the cavity. More specifically, in order to remove the cartridge from the cavity, a user can open the analyzer's lid 1606 a and use the tab to disengage the cartridge from the analyzer. Other mechanisms known to those skilled in the art can also be used to removably and replaceably disengage the cartridge 1900 from the analyzer 1606.

Figure 19:
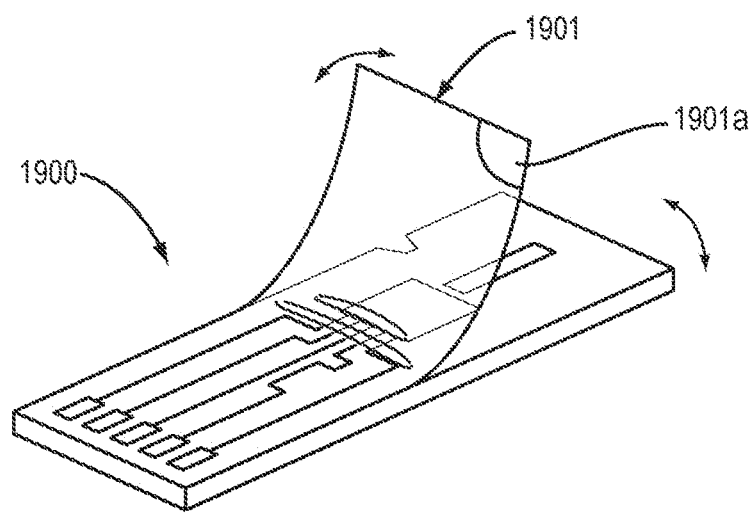
FIGS. 19 and 20 depict a cartridge according to an embodiment.

As shown schematically in FIG. 19, the cartridge 1900 can include a protective peelable layer 1901 (herein also referred to as a protective cover). As discussed in more detail below, the protective layer 1901 can be partially peeled off to allow access to a chamber in the cartridge that is adapted for receiving a food sample. Subsequently, the protective layer can be reapplied to seal the food chamber prior to inserting the cartridge into the analyzer. By way of example, the protective layer 1901 can be formed of a flexible polymeric material, such as polyurethane, or polymethyl methacrylate. A tab 1901 a can facilitate peeling off the protective layer partially or completely.

Figure 20:
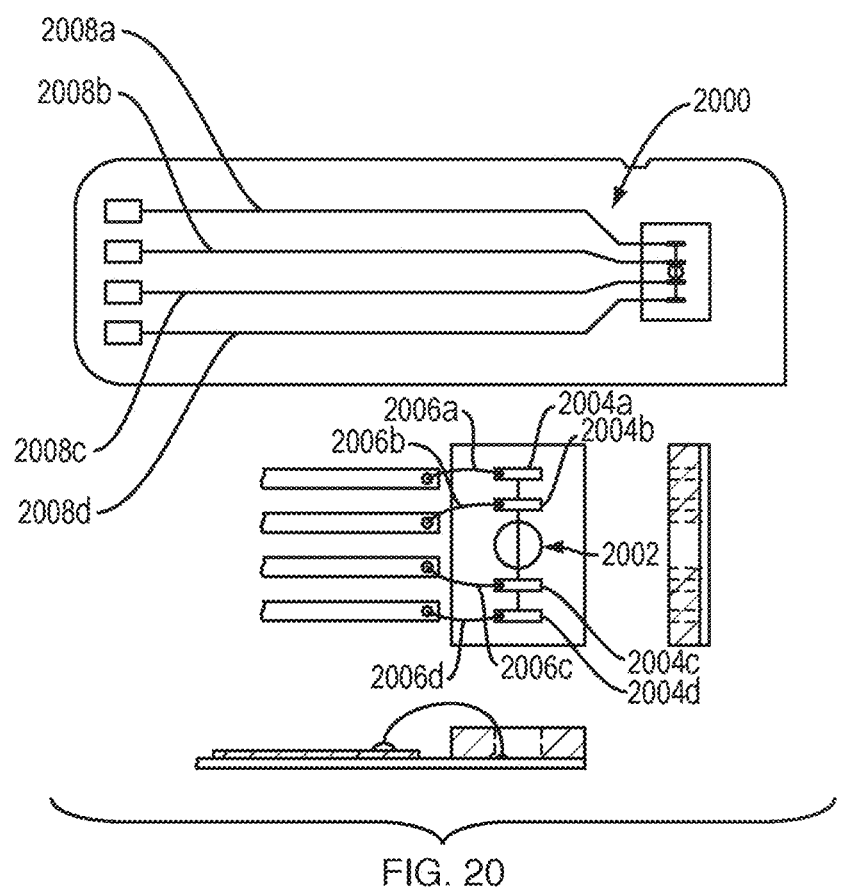

With reference to FIG. 20, the exemplary cartridge 1900 includes a sensor 2000. Sensor 200 comprises one or more sensing element(s) 2002 for detecting and optionally quantifying one or more chemical species of interest, such as one or more gluten proteins, in a food sample. By way of example, the sensor 2000 can be one of the sensors discussed above in connection with the previous embodiments for generating electrical signals in response to interaction with one or more chemical species of interest. In some embodiments, the sensing element of the sensor can include a graphene layer. A plurality of metal pads 2004 a, 2004 b, 2004 c, and 2004 d (herein collectively referred to as metal pads 2004) allow reading one or more electrical signals associated with a change in at least one electrical property of the graphene layer in response to interaction with one or more chemical species. In this embodiment, a plurality of electrical connections 2006 a, 2006 b, 2006 c, and 2006 d electrically couple the metal pads 2004 a, 2004 b, 2004 c, and 2004 d, respectively, to elongated conductive paths 2008 a, 2008 b, 2008 c, and 2008 d, which terminate in electrical pads 2010 a, 2010 b, 2010 c, and 2010 d (herein referred to collectively as "electrical pads 2010"), respectively.

As discussed in more detail below, the analyzer can detect the electrical signals associated with a change in at least one electrical property of the sensing elements via the electrical pads 2010 (and in some embodiments via the electrical pads 2010 and vias connecting the pads to a data acquisition circuitry of the analyzer) and analyze them, e.g., in a manner discussed above in connection with the previous embodiments and further elucidated below. The analysis can determine the presence, and optionally the concentration, of an analyte of interest in a food sample. In some embodiments, a plurality of carbon nanotubes (or other fullerenes) can be employed as the sensing element(s). Further, in some other embodiments, a combination of carbon nanotubes and graphene can be employed as the sensing element.

In some embodiments, the sensing element(s) of the sensor, e.g., carbon nanotubes and/or graphene, can be functionalized with one or more molecular species to facilitate the interaction of the sensing element(s) with one or more chemical species of interest. For example, in some embodiments, the sensing elements can be functionalized with one or more antibodies that can selectively bind to a chemical species of interest so as to facilitate its detection, as discussed in more detail below.

In some embodiments, the sensing elements of a sensor according to the present teachings can be functionalized with one or more antibodies that selectively bind to one or more gluten proteins. By way of example, in some embodiments, the sensing elements (e.g., carbon nanotubes and/or graphene) are functionalized with an antibody that can selectively bind to gliadin. An example of a commercially available antibody that can selectively bind to gliadin is an antibody marketed by Abeam of Cambridge, Mass., U.S.A. under the tradename 14D5. This allows selectively detecting one or more gluten proteins in a food sample against a background of a variety of other species present in that food sample, as discussed in more detail below.

Figure 21A:
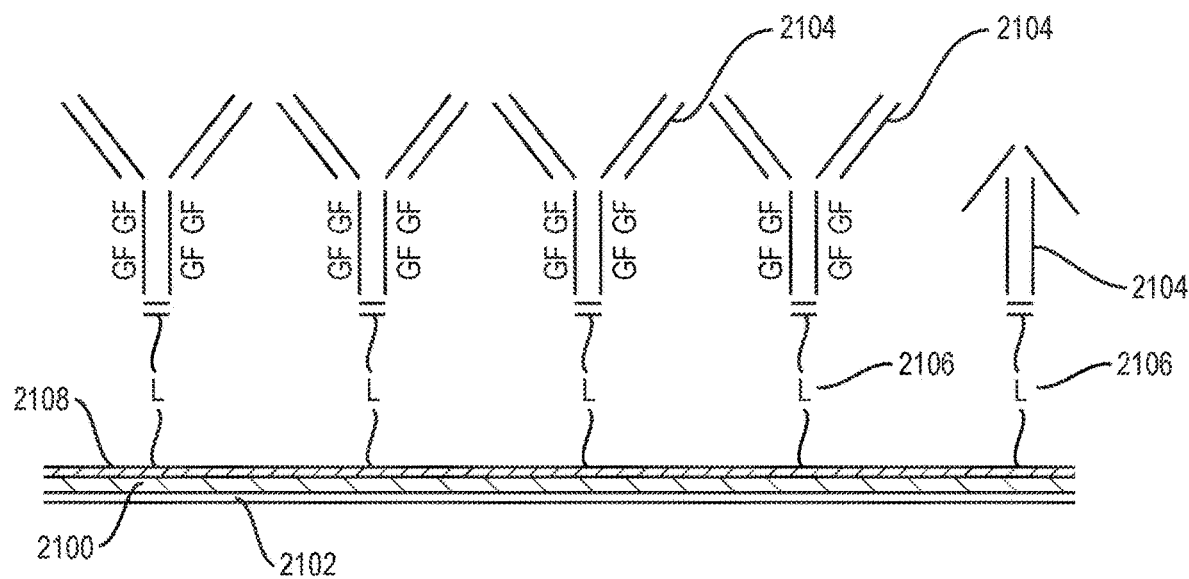
FIGS. 21A and 21B depict a sensing element according to an embodiment.

For example, as shown schematically in FIG. 21A, in one embodiment, the sensing element of a sensor comprises a graphene layer 2100, which is disposed on an underlying substrate 2102. The underlying substrate can be formed of a variety of different materials, such as, silicon, polymeric materials, such as polyurethane, polyethylene terephthalate, or glass, among others. In some embodiments, the graphene layer is disposed over an underlying silicon oxide (SiO2) layer, which is in turn formed as a thin layer in a silicon substrate (e.g., a layer having a thickness in a range of a 200 nm to about 10 microns).

In some embodiments, graphene can be deposited on an underlying silicon substrate by using a variety of techniques known in the art. By way of example, chemical vapor deposition (CVD) can be employed to deposit graphene on an underlying copper substrate. The graphene-coated copper substrate can then be disposed on a silicon oxide layer of a silicon wafer, and the copper can be removed via chemical etching. In some embodiments, the graphene layer is deposited on the underlying substrate as an atomic monolayer, while in other embodiments the graphene layer includes multiple atomic layers.

In this embodiment, the graphene layer is functionalized with a plurality of antibody molecules 2104. More specifically, in this embodiment, a plurality of linker molecules 2016 are attached (e.g., via covalent bonds) at one end thereof to the graphene layer. The linker molecules are adapted to couple (e.g., via covalent bonds) at another end thereof to the plurality of antibody molecules 2014. In this manner, the graphene layer 2100 can be functionalized with a plurality of antibody molecules.

In this embodiment, a plurality of such antibody molecules can cover a fraction of the surface of the graphene layer. In various embodiments, the faction can be at least about 60%, at least about 70%, at least about 80%, or 100% of the surface of the graphene layer. The remainder of the surface of the graphene layer (i.e., the surface areas not functionalized with the antibody) can be passivated via a passivation layer 2108. By way of example, the passivation layer can be formed by using Tween 20, BLOTTO, and/or gelatin. The passivation layer can inhibit, and preferably prevent, the interaction of an analyte of interest in a food sample introduced onto the graphene layer with areas of the graphene layer that are not functionalized with the antibody molecules. This can in turn lower the noise in the electrical signals that will be generated as a result of the interaction of the analyte of interest with the antibody molecules.

Figure 21B:
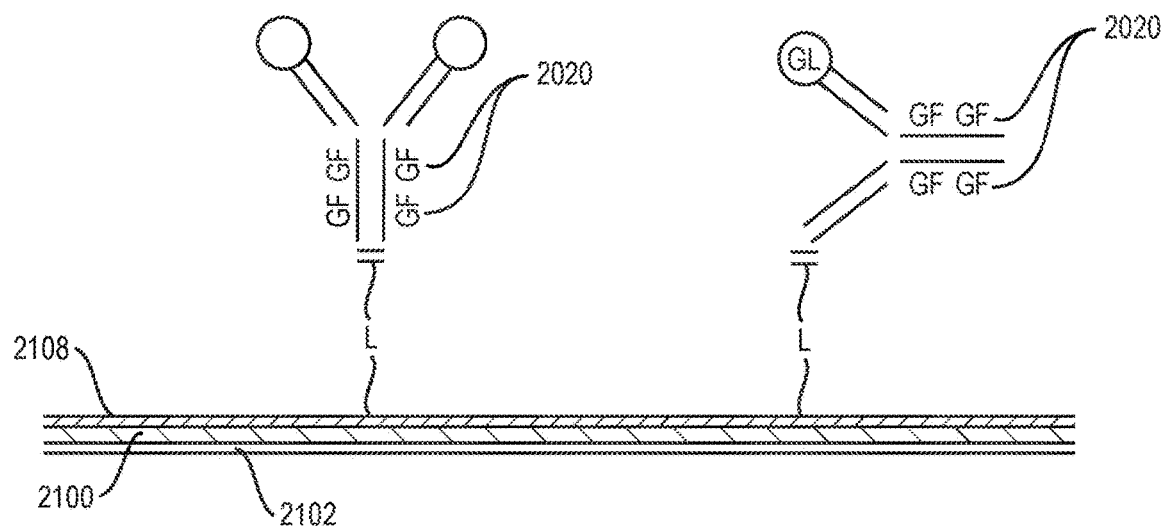

In addition, in this embodiment, at least a portion of the non-binding segments of the antibody molecules can be blocked via a blocking reagent 2020, as seen in FIG. 21B. The blocking reagent 2020 may inhibit the chemical species of interest (gliadin in this embodiment) from binding to those portions and potentially generating false positive signals. In some cases, the blocking reagent can be the same agent employed to passivate the graphene layer, such as those listed above, while in some other cases they can be different. By way of example, in this embodiment, Tween 20 is employed to passivate exposed portions of the graphene layer (i.e., the portions of the graphene layer to which anti-bodies are not attached) and gelatin (GF) is employed to block the non-binding segments of the anti-bodies.

By way of example, with reference to FIGS. 22A-22F, in some embodiments, 1-pyrenebutonic acid succinimidyl ester, depicted in FIG. 22A, is employed as a linker to facilitate the coupling of anti-gliadin antibody molecules 2104 to the underlying graphene (or other fullerenes) layer 2100. As noted above, the anti-gliadin antibody can be 14D5 antibody marketed by Abcam for selectively binding to the gliadin protein. Other linkers and/or antibodies can also be used. The selection of the linker and the antibody depends, at least in part, on the type of application for which the device is employed, the desired bonding level of the antibody to an analyte of interest, the cost of the linker and/or the antibody, etc. The attachment of the linker molecules (1-pyrenebutonic acid succinimidyl ester in this embodiment) is schematically depicted in FIG. 22C.

By way of example, in some embodiments, a graphene layer formed on an underlying substrate (e.g., plastic, a semiconductor, such as silicon, or a metal substrate, such as a copper film) can be incubated with the linker molecule (e.g., a 5 mM solution of 1-pyrenebutonic acid succinimidyl ester) for a few hours (e.g., 2 hours) at room temperature. The linker modified graphene layer can then be incubated with an antibody (e.g., 14D5) in a buffer solution (e.g., NaCO3-NaHCO3 buffer solution (pH 9)) at a selected temperature and for a selected duration (e.g., 7-10 hours at 4 C), followed by rinsing with deionized (DI) water and phosphate buffered solution (PBS). In order to quench the unreacted succinimidyl ester groups, the modified graphene layer can be incubated with ethanolamine (e.g., 0.1 M solution at a pH of 9 for 1 hour). FIG. 22D schematically depicts the coupling of the antibody molecules (in this embodiment anti-gliadin antibody molecules) to the linker molecules previously attached to the graphene layer.

Subsequently, the non-functionalized graphene areas can be passivated via a passivation layer 2108, as shown schematically in FIG. 22E. The passivation of the non-functionalized portions of the graphene layer can be achieved, e.g., via incubation with 0.1% Tween 20.

While in some embodiment a single type of antibody molecule is employed to functionalize the entire graphene layer, in other embodiments, different types of antibody molecules can be used to functionalize the graphene layer.

Figure 23:
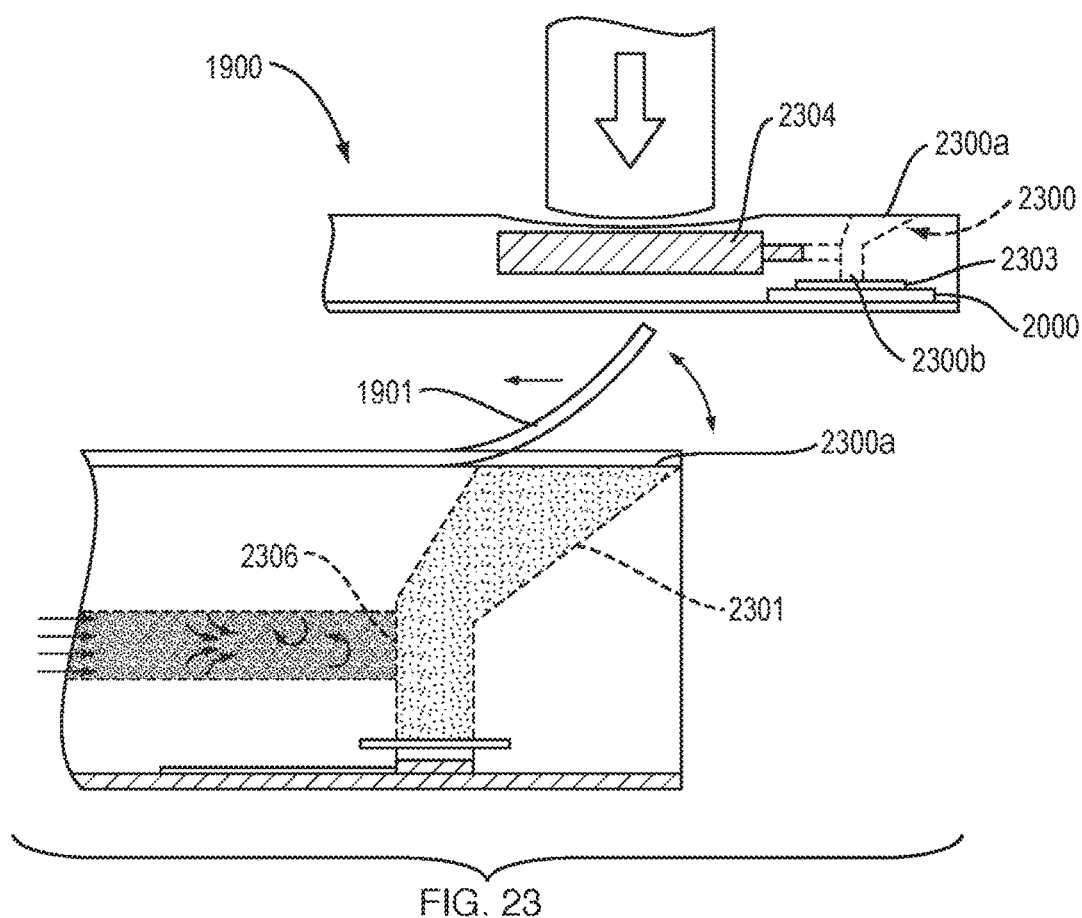
FIG. 23 depicts a cartridge according to an embodiment.
Figure 24A:
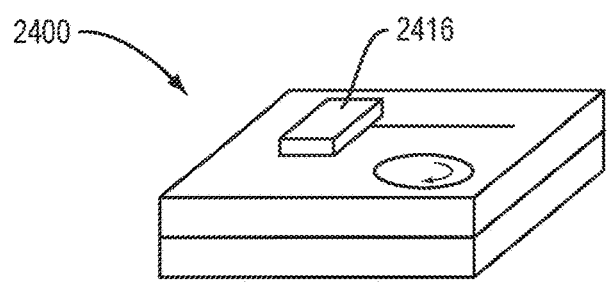
FIGS. 24A-24D, 25, and 26 depict various food grinding mechanisms according to different embodiments.
Figure 24B:
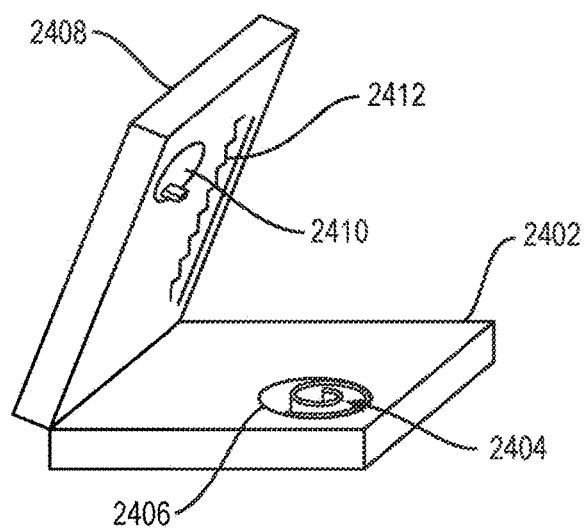
Figure 24C:
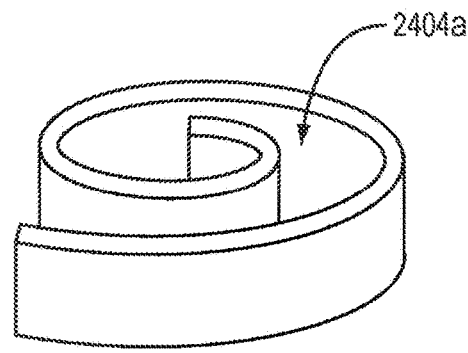
Figure 24D:
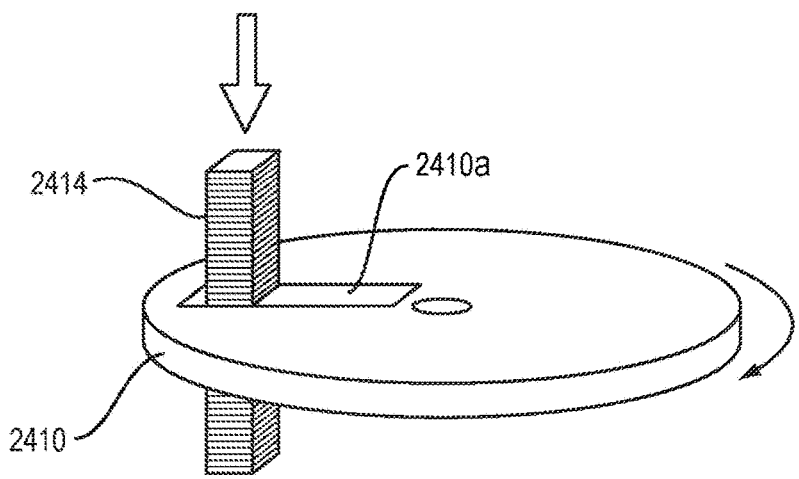

Referring now to FIG. 23, the cartridge 1900 includes a food chamber 2300 for receiving a food sample ("herein also referred to as the food chamber"), which is disposed above the sensor 2000. The food chamber 2300 includes an input port 2300 a through which a food sample can be introduced into the food chamber and an output port 2300 b. In this embodiment, the food chamber 2300 includes a top portion 2301 and a lower portion 2302. The top portion 2301 is slightly slanted relative to the top surface of the cartridge and exhibits a flared cross-section. The lower portion 2302 is substantially vertical and can function as a capillary tube for transferring a liquid mixture of at least a portion of the food sample and a process liquid into the underlying sensor, as discussed in more detail below.

In this embodiment, one or more filters 2303 are disposed between the output port of the food chamber and the underlying sensor. In other embodiments, the cartridge may not include such filters and the liquid mixture, via extraction of a portion of the food sample by a process liquid, can be directed onto the sensor (e.g., onto a functionalized graphene layer) without first passing through one or more filters.

The cartridge further includes a liquid reservoir 2304 in which a quantity of a process liquid is stored. A variety of process liquids can be employed. By way of example, in some embodiments, the process liquid includes an alcohol (e.g., ethanol). In some embodiments, the process liquid can be a mixture of water and alcohol with the volume concentration of alcohol ranging, e.g., from about 10% to about 70%, e.g., in a range of about 15% to about 50%.

In some embodiments, the volume of the liquid reservoir can be in a range of about 0.1 milliliters (ml) to about 0.2 ml, and the volume of the chamber for receiving the food sample can be in a range of about 0.03 ml to about 0.1 ml, although other volumes can also be employed.

The food chamber 2300 is separated from the liquid reservoir by a thin frangible membrane 2306. In some embodiments, the thickness of the frangible membrane can be less than about 5 microns, for example, in a range of about 2 microns about 5 microns.

A variety of different materials can be used to fabricate the cartridge including the frangible membrane. Some examples of such materials include, without limitation, PMMA (polymethymethacrylate), PDMS (polydimethysiloxane). Further, a variety of fabrication techniques, such as molding, can be utilized to fabricate the cartridge.

With continued reference to FIG. 23, in use, a user can peel back the peelable layer 1901 to expose the input port 2300a of the food chamber. The user can introduce a food sample into the food chamber and reapply the peelable cover 1901. The cartridge 1900 can then be placed in the analyzer. The user can apply a compressive pressure to the liquid reservoir 2304 (as shown schematically by the vertical arrow) to cause the rupture of the frangible membrane 2306, thereby allowing at least a portion of the process liquid stored in the liquid reservoir 2304 to enter the food chamber. In some embodiments, the closing of the cover of the analyzer can result in application of the compressive pressure (e.g., via a protrusion provided in the cover adapted to be in register with a thin upper wall of the liquid reservoir) on the liquid in the reservoir. The liquid can in turn transfer the applied pressure to the thin frangible membrane, which separates the liquid reservoir from the food sample chamber.

Once the pressure exceeds a threshold, the membrane ruptures allowing the process liquid to enter the food chamber. The process liquid can extract, e.g., via solvation, certain constituents of the food sample stored in the food chamber. The resultant mixture can exit the food chamber via its output port to be introduced onto the underlying sensor, e.g., after passage through one or more filters. In some embodiments, such a mixture can be in the form of a solution or a colloidal mixture. As discussed in more detail below, in some embodiments, the food sample solution can be drawn via capillary forces to one or more filters disposed between the food chamber and the sensor.

Figure 27A:
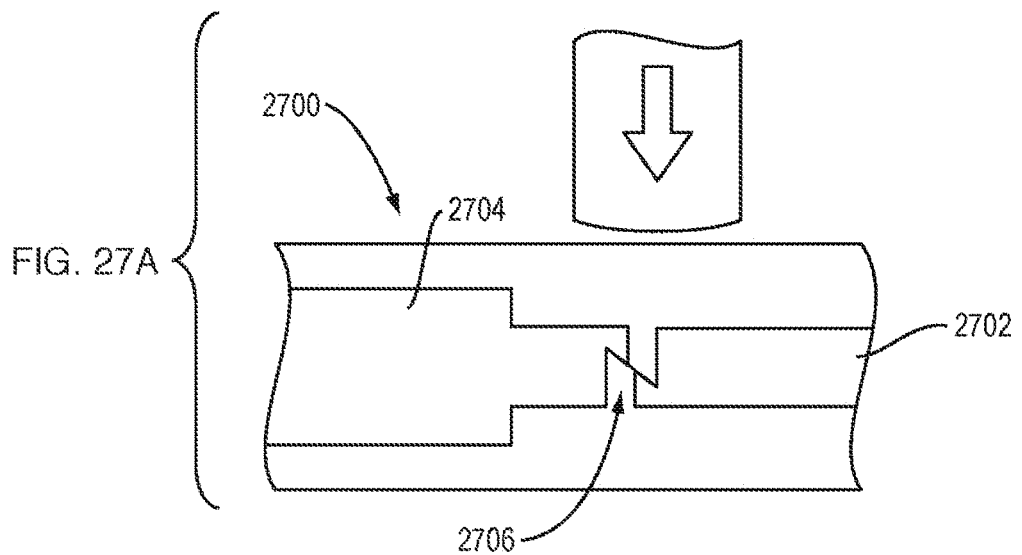
FIGS. 27A and 27B show partial schematic views of a cartridge according to an embodiment.
Figure 27B:
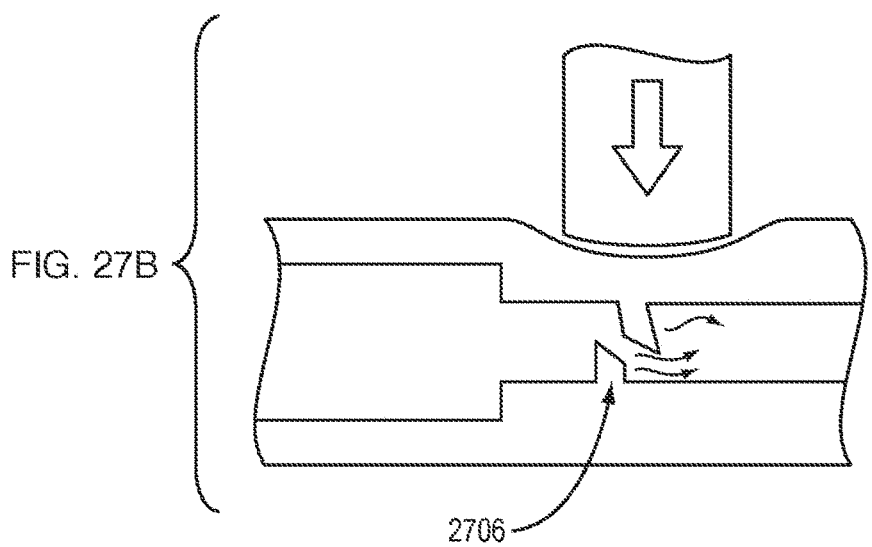

In some embodiments, rather than using a thin frangible membrane, other mechanisms can be employed for providing a breakable separation between the food chamber and the liquid reservoir. By way of example, FIGS. 27A and 27B show a modification of the cartridge 1900 in which a constriction, rather than a frangible membrane, separates a food chamber from a liquid chamber. More specifically, FIGS. 27A and 27B show partial schematic views of a cartridge 2700 according to an embodiment. Cartridge 2700 includes a chamber 2702 for receiving a solid and/or liquid food sample, and an adjacent chamber 2704 for containing a process liquid, e.g., an alcohol or an aqueous solution of an alcohol. A normally constricted channel 2706 separates the food chamber 2702 from the liquid chamber 2704, thus preventing the flow of the liquid into the food chamber. Once a food sample has been introduced into the chamber 2702, a user can apply pressure to a surface area above the constricted channel (as shown schematically by the vertical arrow) to cause at least partial opening thereof, as shown in FIG. 27B, so as to allow at least a portion of the process liquid in the chamber 2704 to be introduced into the food sample channel 2702. The process liquid can dissolve at least a portion of food sample and the resultant solution can then be introduced via a capillary tube through one or more filters onto the sensing element(s) of the cartridge, e.g., in a manner discussed above.

Figure 28A:
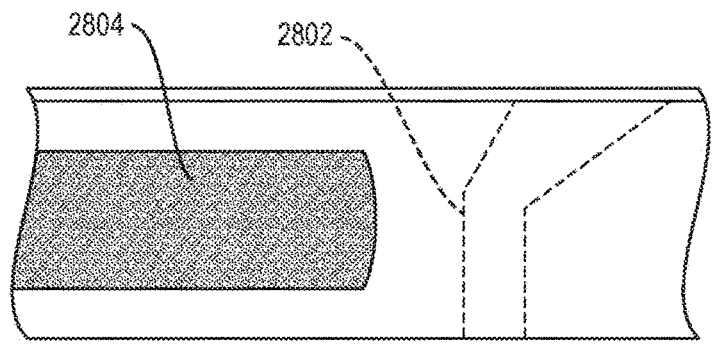
FIGS. 28A-28C, depict views of a cartridge employing a needle according to an embodiment.
Figure 28B:
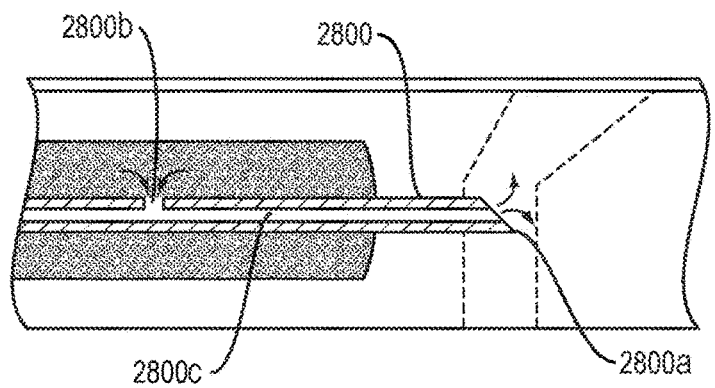

In yet another embodiment, as shown in FIGS. 28A and 28B, a sharp needle 2800 can be employed. Sharp needed 2800 can puncture a frangible membrane 2802 separating a liquid chamber 2804 of the cartridge from its food sample chamber 2806 to initiate analysis of a food sample previously introduced into the food chamber. In this embodiment, the needle 2800 extends at least partially across the process liquid chamber 2804 and includes a sharp tip portion 2800 a that can be pushed against the frangible membrane separating the liquid chamber from the food chamber so as to puncture the frangible membrane. Upon the puncture of the frangible membrane, the liquid in the liquid chamber can enter via an opening 2800 b provided in the needle into a central lumen 2800 c of the needle and exit through an output opening provide at the tip of the needle to enter the food chamber.

Figure 28C:
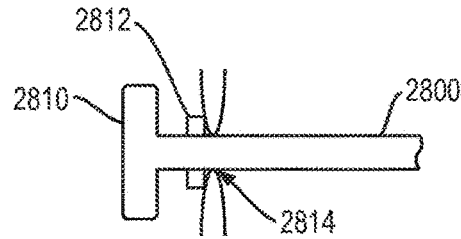

With reference to FIG. 28C, in some embodiments, a cap 2810 attached to the needle 2800 is externally accessible. The cap 2810 enables a user to push the needle toward the frangible membrane separating the liquid chamber from the food chamber. More specifically, the cap includes a low-profile collar 2812 that sits against an external wall of the cartridge when the needle is in a deactivated state. The low-profile collar 2812 prevents the axial motion of the needle unless activated by a user as discussed below. As the user presses the cap, the collar 2812 can flex and pass through the opening 2814 provided in the cartridge's wall. Pressing the cap can then push the tip of the needle into the frangible membrane separating the process liquid chamber from the food chamber. The passage of the collar through the opening 2814 can generate a clicking sound that can alert the user that the device has been activated.

Figure 29:
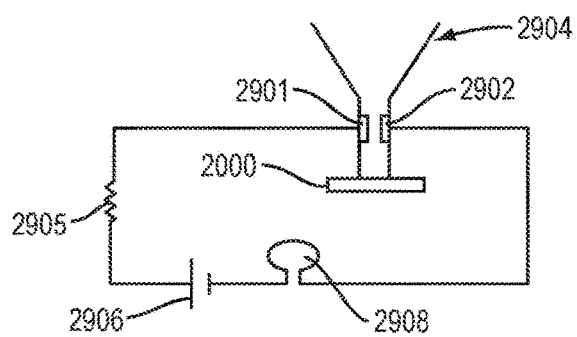
FIG. 29 depicts a mechanism for triggering a signal to a user according to an embodiment.

In some embodiments, a visual and/or audible signal can be employed to inform a user that the cartridge has been activated, i.e., the separation between the liquid reservoir and the food chamber has been broken. For example, the puncture of the frangible membrane can initiate the generation of an electrical signal that can in turn cause the illumination of a light source, such as an LED, and/or generation of an audible tone. By way of example, as shown schematically in FIG. 29, two electrodes 2901 and 2902 can be placed in a capillary tube 2904 through which a liquid mixture of a food sample and a process liquid passes to reach an underlying sensor. The electrode 2901 is electrically coupled via a resistor 2905 and a voltage source 2906, e.g., a battery, to a light source 2908. By way of example, the voltage source and/or the light source can be incorporated in an analyzer to which the cartridge 2501 can be coupled. The other electrode 2902 is coupled to the other side of the light source 2908. Before activation of the cartridge, the electrodes are separated by the space within the capillary tube, thus resulting in an open circuit. Once the cartridge is activated, a solution of a food sample will pass through the capillary tube, which can provide an electrical path between the two electrodes, thereby closing the circuit comprising the light source so as to activate the light source.

Figure 30:
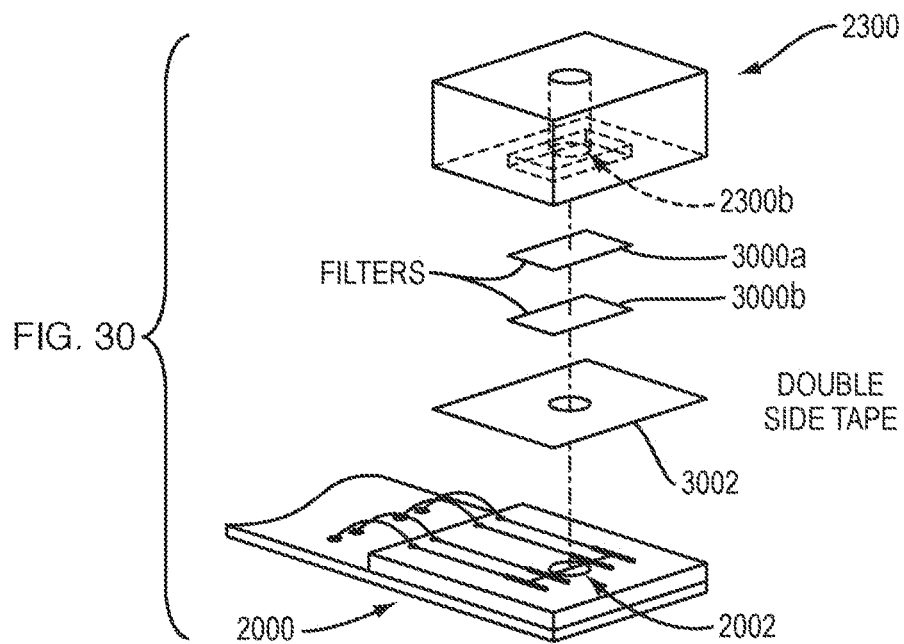
FIG. 30 is a schematic exploded view of a portion of a cartridge according to an embodiment.

Referring now to FIG. 30, after introduction of the process liquid (e.g., a solution of alcohol and water) into the food chamber, at least a portion of a mixture (e.g., a solution) of the food sample and the process liquid exits the food chamber via the output port 2300 *b*, e.g., via capillary action of the lower vertical portion of the food chamber. The mixture that exits is introduced onto two filters 3000 *a* and 3000 *b* that are disposed below the output port of the food chamber and above the sensing element(s) 2002 of the sensor 2000 (e.g., antibody-functionalized graphene layer in this embodiment).

The filters 3000 *a* and 3000 *b* are capable of blocking certain chemical species in a sample under study from reaching the sensing element(s) while allowing one or more other chemical species to pass through to reach those elements. A double sided tape 3002 having a central opening can facilitate fixating the filters 3000 *a* and 3000 *b* while allowing the liquid exiting the food chamber to reach the sensing element(s) 2002 via its central opening.

In some embodiments, one of the filters (e.g., 3000 *a*) can be an oleophobic filter that can block oily substances (e.g., substances including fat molecules) from reaching the sensing elements. By way of example, the oleophobic filter can be obtained from Donaldson Filtration Solutions of Minneapolis, U.S.A. under tradename Dura-life oleophobic filter or can be obtained from Gore of Newark Del. The other filter (e.g., filter 3000 *b*) can be hydrophobic so as to inhibit chemical species that are soluble in water from reaching the sensing element(s) 2002. By way of example, the hydrophilic filter can be a Teflon® coated filter.

In some embodiments, rather than employing two filters as discussed above, a single filter can be used that exhibits both hydrophobic and oleophobic properties. In some embodiments, such a filter can selectively allow the passage of chemical species soluble in an alcohol through the filter. An example of a suitable filter is disclosed in the section below, which discusses an oleophobic hydrophobic filter.

Briefly, such a filter includes a substrate having a top surface to which a polymeric material is applied. Such a polymeric material can be, for example, a polymer known as Nafion®, which is marketed by Dupont Chemical Company of Wilmington Del., U.S.A. A variety of substrates can be employed. In some embodiments, the substrate is porous and includes cellulose fibers. As discussed in more detail below, in some embodiments, such a filter can be employed in a device according to the present teachings for detecting gluten proteins in a sample.

Other filters can also be employed to practice the present teachings. By way of example, U.S. Pat. No. 8,695,810 entitled "Superoleophobic and superhydrophilic Fabric Filters for Rapid Water-Oil Separation," which is herein incorporated by reference in its entirety, discloses a filter that can be employed in some embodiments of the present teachings.

The portion of the solution that has passed through the filters 3000 *a* and 3000 *b* (herein also referred to as the filtrate) reaches the sensing element(s) of the underlying sensor. As discussed above and shown schematically in FIG. 21A, in this embodiment, the sensing element is a graphene layer that has been functionalized by a plurality of antibody molecules. By way of example, the graphene layer can be functionalized with antibody molecules that selectively bind to the gliadin protein. If gluten is present in the filtrate reaching the sensing element, the binding of the gliadin molecules to the antibody molecules can cause in a change in one or more electrical properties of the underlying graphene layer.

By way of example, the binding of the gliadin molecules to the antibody can modulate the electrical resistance of the underlying graphene layer. The modulation of the electrical resistance of the graphene layer can be detected and analyzed to determine whether gliadin protein is present in the food sample. It should be understood that the teachings of the present disclosure are not limited to detecting gluten proteins in a food sample, but can be employed to detect other chemical species, including a variety of proteins and other analytes in a food sample.

Referring again to FIG. 16A, the analyzer 1606 can be implemented in a manner discussed above in connection with analyzer 12 to receive electrical signal(s) associated with the sensing element(s) of the sensor and analyze those signals to determine, e.g., the probability that a species of interest (such as gluten) is present in a food sample, and optionally quantify the concentration of that species.

More specifically, FIG. 31 schematically shows an analyzer 1606 according to some embodiments. The analyzer 1606 can include a data acquisition module 3100 and a data analysis module 3102. The data acquisition module 3100 can detect electrical signal(s) generated by the sensing elements of the sensor in response to interaction with a food sample. The data analysis module 3102 can analyze the detected signals to determine whether at least one species of interest, such as gluten, in present in the food sample.

Figure 31A:
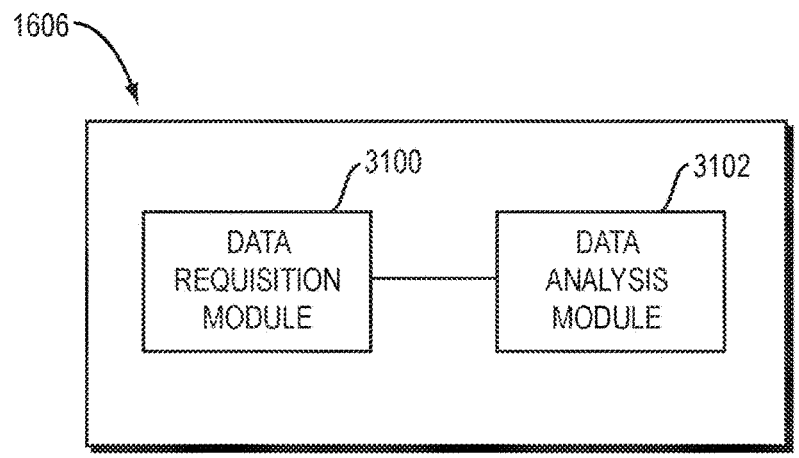
FIGS. 31A and 31B schematically shows an analyzer according to some embodiments.
Figure 33A:
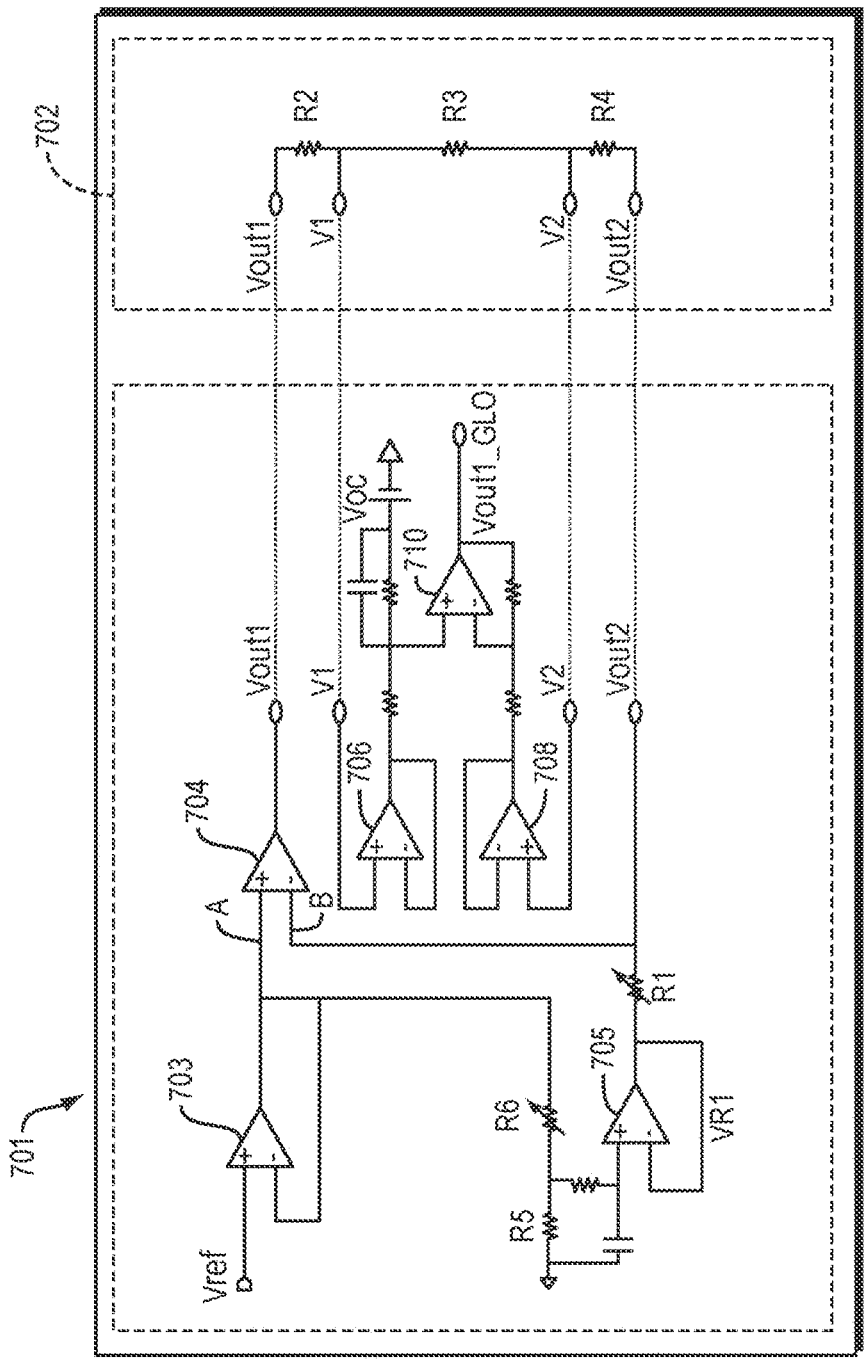
FIGS. 33A and 33B show exemplary circuits for measuring electrical resistance of a sensor according to some embodiments.

With reference to FIGS. 31A and 33A, in this embodiment, the data acquisition module 3100 can include a circuit 701 for measuring changes in the electrical resistance of the sensing elements of the sensor 1614. The changes may be caused by the interaction of the sensing element(s) of the sensor with one or more species present in a food sample under study. In some embodiments, the sensing elements can exhibit an electrical resistance, for example, in a range of about 300 kΩ to about 10 MΩ. The electrical resistance can change in response to interaction of the sensing elements with one or more analytes in a sample to which the sensing elements are exposed. Such a change in the electrical resistance, and in some cases the change in the electrical resistance as a function of time, can provide a signature of the analyte of interest.

More specifically, FIG. 33A shows an exemplary circuit 701 that can be employed for measuring electrical resistance of a sensor, e.g., sensor 702 that is depicted in this figure as an equivalent circuit diagram of a sensor according to the present teachings. A fixed voltage V (e.g., 1.2 V) is generated at the output of a buffer operational amplifier 703. This voltage is applied to one input (A) of a downstream operational amplifier 704 having another input B that is coupled to a variable voltage generator operational amplifier 705 via a variable resistor R1. The output of the operational amplifier 704 (Vout 1) is coupled to one end of the sensor 702 and the input B of operational amplifier 704 is coupled to the other end of the sensor 702. In this schematic diagram, resistor R2 denotes the resistance between two electrode pads at one end of a sensor, resistor R3 denotes the resistance of the nanotubes (or graphene or other fullerenes) of a sensor extending between two electrode pads of the sensor, and resistor R4 denotes the resistance between two electrode pads at the other end of the sensor. The operational amplifier 704 maintains the voltage at the input B at the fixed voltage applied to its input (A), e.g., 1.2 V. An adjustable current source is generated by operational amplifier 705 and adjustable resistor sR1 and R6, which push an adjustable current flow through the sensor 702. The voltage V1 and V2 generated across the resistor R3 are applied, respectively, to an input of each of the operational amplifiers 706 and 708. As the other input of each of the operational amplifiers 706 and 708 is coupled to their respective outputs, the voltage V1 and V2 appear at the outputs of the operational amplifiers 706 and 708. The voltages V1 and V2 are then applied to the two inputs of a differential operational amplifier 710 whose output is indicative of a difference between V1 and V2 (designated as Vout1_GLO). The voltage difference (V1–V2) together with the known current applied to R3 can then be used to determine the resistance of R3 (i.e., the resistance of one or more sensing elements). As discussed above, the measurement of the resistance as a function of time, in response to exposure of the sensing element to an liquid under test, can then be analyzed to determine the presence (or the probability of presence) of an analyte of interest in that liquid. The value of Vout1_GLO is equal to V1–V2+ Vdc. Vdc is another reference voltage generated by the circuit.

Figure 33B:
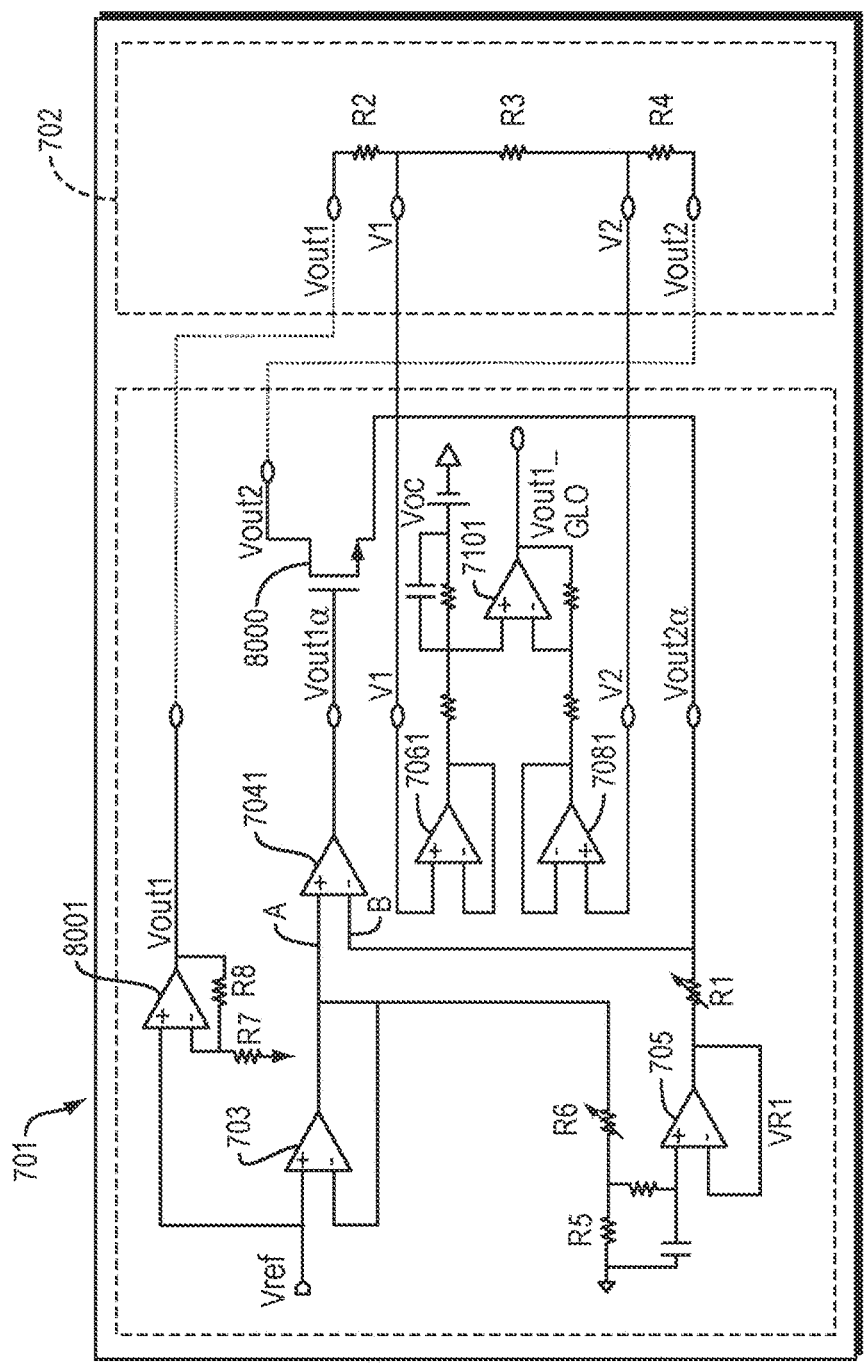

FIG. 33B shows a variation of the above circuit depicted in FIG. 33A according to an embodiment. In FIG. 33B, an NMOS, n-channel metal oxide semiconductor, transistor is added to the output and the minus input of the amplifier 7041. The voltage at the drain of the NMOS resistor provides the voltage Vout2 that is applied to one end of the resistor chain R2-R3-R4. Another voltage Vref provides, via operational amplifier 8001, the voltage Vout1 that is applied to the other end of the resistor chain R2-R3-R4.

In this circuit the adjustable current source generated by operational amplifier 705 and adjustable resistors R1 and R6 push the adjustable current flow through the NMOS transistor which is then forced into the sensor 7021.

The voltage difference (Vout1–Vout2) generates a current through the resistor R3 whose resistance is to be measured. The use of the NMOS transistor eliminates the connection of the minus input of the operational amplifier 7041 to the resistor R3, thereby eliminating the potential of oscillations that such connection might cause.

Referring back to FIG. 31B, the data analysis module 3102 receives the measured electrical data from the data acquisition module 3100 and operates on that data, e.g., in a manner discussed below. The operation determines whether a species of interest, e.g., gliadin, is present in a food sample. Such determination can be in the form of determining the probability that a species of interest is present in the sample. In some embodiments, if the concentration of the species of interest is less than the detection sensitivity of the device, the analysis module may indicate that the species is not present in the food sample.

In some embodiments, the data analysis module 3102 compares the temporal variation of an electrical signal generated by the sensing elements with a calibrated temporal profile of one or more species of interest to determine the probability of presence of those species in a sample under study. By way of example, in some embodiments, the probability that a food sample contains gluten proteins can be ascertained in the following manner.

In some embodiments, a visual inspection of a measured temporal variation and its comparison with a calibrated temporal profile can be employed to determine whether an analyte of interest is present in a food sample (or a measure of the probability that the analyte is present in the food sample). In other embodiments, an algorithm, such a curve matching algorithm, can be employed to compare a measured temporal profile with a calibration profile, as discussed in more detail below.

A food sample is brought into contact with an aqueous solution of ethanol, e.g., in a manner discussed above. A mixture of at least a portion of the food sample and the aqueous solution is passed through one or more filters and brought into contact with a graphene layer functionalized with anti-gliadin antibody molecules, in a manner discussed above. An electrical signal associated with the sensing elements in response to interaction of the mixture with the antibody-functionalized graphene layer (e.g., variation of voltage or current generated by the sensing elements) is collected via the data acquisition module 3100 over a period of time.

The data analysis module 3102 receives the electrical signal from the data acquisition module. The data analysis module 3102 may compare the temporal variation of the electrical signal with a previously-obtained calibration signal to determine how closely the measured electrical signal resembles the calibration signal. For example, a merit function can be employed for comparison of the measured electrical signal with the calibration signal to determine the probability that a species of interest is present in a sample. In some cases, pattern recognition techniques can be employed to assess whether the obtained signal matches a calibration signals.

Various embodiments may employ a curve matching technique. One example of such a technique is discussed in an article entitled "Curve Matching, Time Warping, and Light Fields: New Algorithms for Computing Similarity Between Curves." The techniques are employed to compare a temporal signal obtained in response to the interaction of the sensing elements with a food sample with at least one calibration signal associated with a species of interest. The comparison may assess how well a curve representing the temporal variation of the signal matches the calibration curve in order to estimate the probability that the species is present in the sample.

By way of example, when the chemical species of interest is one or more gluten proteins, one or more calibration samples containing known amounts of one or more gluten proteins can be employed. The electrical signals associated with the sensing elements of the sensor in response to interaction (e.g., contact) with one or more calibration samples can be measured to generate calibration signals. In some cases, measurements of multiple calibration samples can be performed and averaged to generate an average calibration signal (curve). The probability that one or more gluten proteins are present in a food sample can then be determined by comparing a curve representing temporal variation of an electrical signal generated by the sensing elements in response to interaction with the food sample with the calibration curve(s).

In embodiments in which one or more filters and antibody functionalized graphene are employed, the presence of an analyte of interest can be determined by detecting a statistically significant variation of the electrical signal in response to interaction of the functionalized graphene with the sample.

Figure 31B:
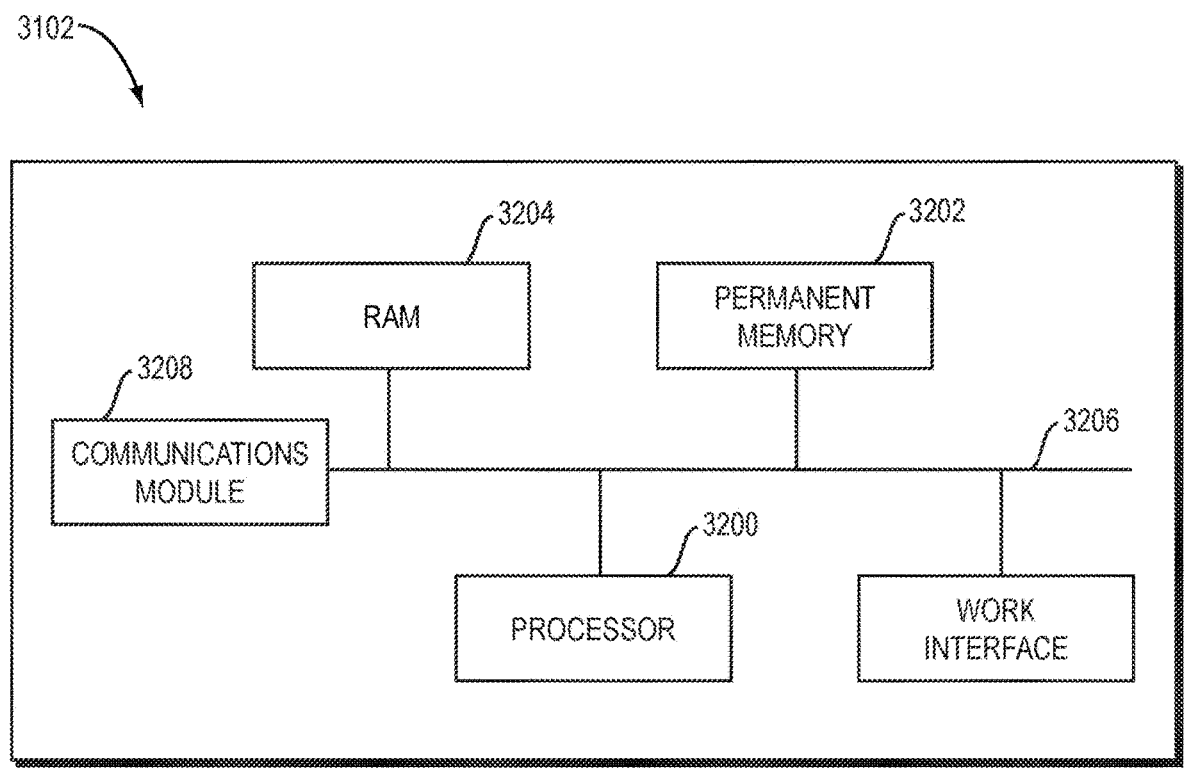

Returning to FIGS. 31A and 31B, the data analysis module 3102 can be implemented in hardware, software, firmware or a combination thereof. By way of example, as depicted in FIG. 31B, the data analysis module 3102 can include a processor 3200, permanent memory 3202, random access memory (RAM) 3204, a communication bus 3206, and a communication module 3208. The communication bus 3206 may connect the processor with the memory 3202 and 3204. The communication module 3208 may communicate with the data acquisition module 3100, among other components known in the art. Instructions for operating on the received data in a manner discussed above, as well as calibration data, can be stored in the permanent memory 3202. Upon receipt of electrical data from the data acquisition module, such data can be stored in the RAM 3204 under control of the processor 3200. The process can then effect the transfer of the data analysis instructions (or at least the needed portions thereof) and the calibration data into the RAM 3204. The processor will utilize the instructions and the calibration data to operate on the received data so as to determine whether the species of interest in the present in the food sample in a manner discussed above.

In some embodiments, the result of the analysis performed by the data analysis module 3102 can be transferred to a mobile device for presentation to a user via a graphical user interface (GUI) of the mobile device. For example, the results can be transferred via a wireless protocol (e.g., Bluetooth or WiFi protocols) to a user's mobile device (e.g., mobile phone, tablet, etc.) to be presented to the user. By way of example, a client program residing on the mobile device can communicate with data analysis module 3102 to receive the analysis result. The client program can be, for example, a downloadable app operating under off-the-shelf standard mobile operating systems (e.g., IOS, Android, Microsoft, etc.).

Referring again to FIG. 31B, the data analysis module 3102 can further include a network communication interface (e.g., a wireless communication interface) 3208 to allow the analysis module to communicate with other network-enabled devices to transfer the results of the analysis of the data to those devices. By way of example, as noted above, the data analysis module 3102 can communicate via a wireless protocol to other devices. In some embodiments, the data analysis module 3102 can communicate via the Bluetooth protocol to send the results of analysis of a sample under study to a user's device, e.g., a mobile device such as a mobile phone or a tablet, for presentation to the user.

Figure 31C:
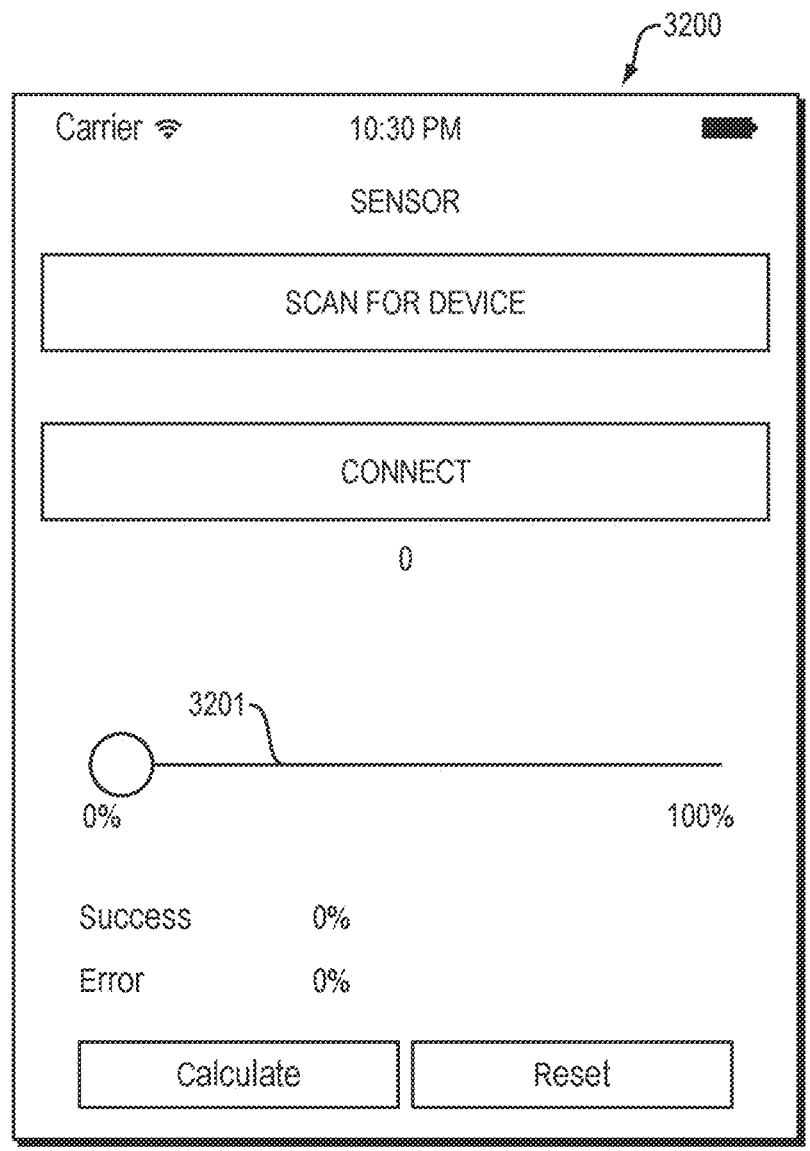
FIG. 31C shows a graphical user interface according an embodiment.

Some embodiments employ a software application (herein also referred to as an app) for presenting the analysis results to a user. The software application can be configured to be executable on a mobile device, such as a mobile phone, and can receive the analysis data from the data analysis module 3102 and present that data to a user. By way of example, FIG. 31C shows the graphical user interface (GUI) 3200 of such an app. GUI 3200 can present the result of analysis of a food sample to determine the probability of presence of gluten proteins in that sample. A graphical element 3201 graphically depicts the probability that one or more gluten proteins are present in a food sample. The GUI 3200 allows a user to scan for the analyzer and connect, e.g., via Bluetooth, to the analyzer. The GUI 3200 further allows a user to instruct the analyzer to calculate the probability that gluten is presence in the sample.

B. FOOD GRINDING MECHANISMS

Some embodiments use food grinding mechanisms to grind or press a food sample before exposing it to a process liquid. Doing so may increase the surface area of the food sample and cause it to better mix and interact with the process liquid. Different embodiments may use different food grinding mechanisms. Some of these mechanisms are discussed below.

Referring now to FIGS. 24A-24D, in some embodiments, a device is employed to grind and/or crush a food sample prior to introducing it into the food chamber of a cartridge according to the present teachings. Such a device can be a stand-alone device or can be integrated with the cartridge, as discussed below. By way of example, FIGS. 24A-24D depict such a device 2400 for grinding a food sample. The device 2400 includes a base 2402 that includes a helical structure 2404. Helical structure 2404 provides an internal serpentine path 2404 a. The internal path terminates in a well 2406 in which the ground food sample can be collected, as discussed below. The device 2400 further includes a cover 2408 that is hingedly attached to the base 2402. A rotatable pinion 2410 is disposed in the cover, which is coupled to a rack 2412. The pinion 2410 includes a groove 2410 a in which a grinding element 2414 is engaged. The grinding element 2414 is configured such that upon closure of the cover it engages at an end thereof within the internal serpentine path provided by the helical structure. A knob 2416 is attached to the rack to allow linearly moving the rack and hence rotating the pinion.

In use, a user opens the cover 2408 and places a food sample within the serpentine path and closes the cover. The user then uses the knob 2416 to rotate the pinion 2410. The rotation of the pinion in turn causes the grinding element to move along the serpentine internal path provided by the helical element and hence grind the food sample and push the ground food sample into the well 2406. The user can open the cover and collect the crushed food sample and introduce it into the food chamber of the cartridge 1900.

Alternatively, in some embodiments, the food grinding device is integrated with the cartridge 1900. In such embodiments, the well 2406 of the grinding device can be modified to be an opening in register with the input port of the food chamber of the cartridge. In such cases, the ground food sample may be introduced into the food chamber at the distal end of the serpentine path provided by the helical element.

Figure 25:
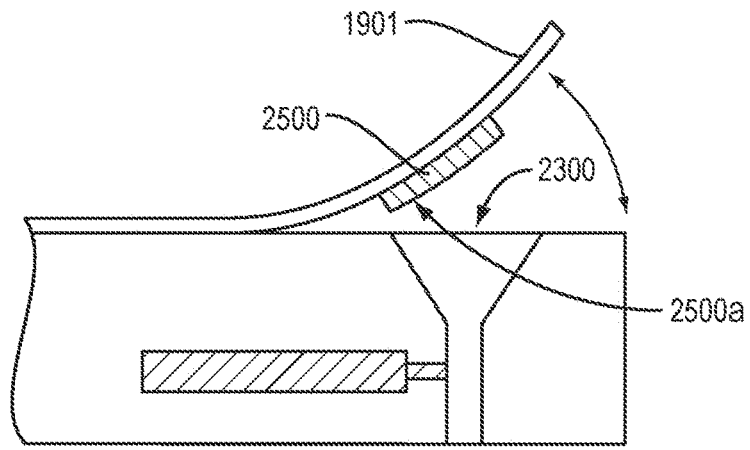

Other devices for grinding the food sample can also be employed. FIG. 25 schematically shows another grinding mechanism according to some embodiments. In particular, FIG. 25 schematically depicts that in some embodiments, the protective cover 1901 of the cartridge can include a protrusion 2500 having an abrasive, corrugated surface 2500a for grinding a food sample introduced in the food chamber 2300 of the cartridge. Specifically, the user can partially peel off the cover 1901 to expose the cartridge's food chamber. A food sample can then be introduced into the food chamber. Upon reapplication of the protective cover 1901, the abrasive surface 2500a of the protrusion 2500 will compress and grind the food sample.

Figure 26:
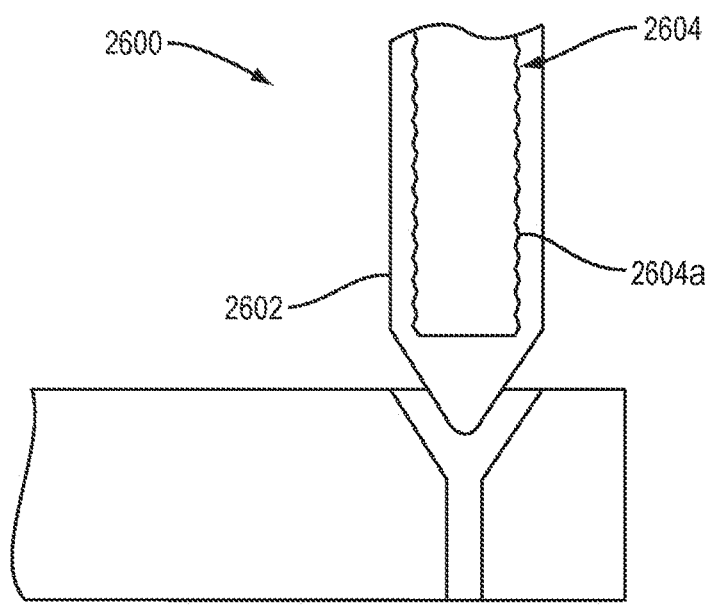

FIG. 26 schematically shows yet another grinding mechanism according to some embodiments. In FIG. 26, a food crushing device 2600 includes a barrel 2602 and a plunger 2604 that is movable within the barrel. In this embodiment, the outer surface of the plunger is an abrasive surface so as to crush a food sample drawn into the barrel as the plunger advances in the barrel.

Figure 32A:
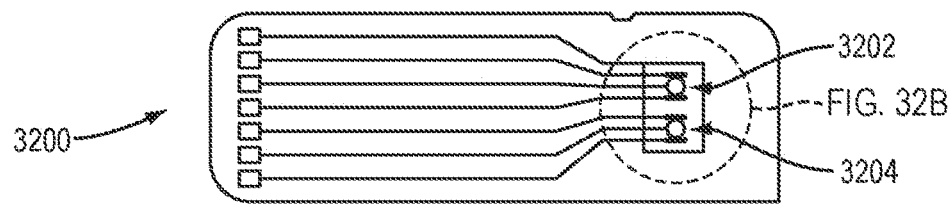
FIGS. 32A and 32B schematically depict a cartridge that incorporates two sensors according to an embodiment.
Figure 32B:
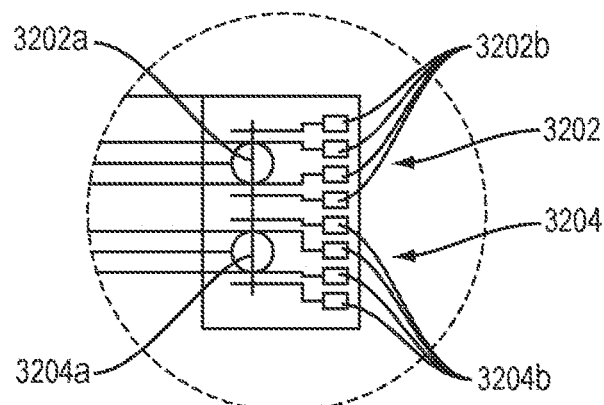

In some embodiments, a cartridge according to the present teachings can comprise a plurality of sensors. By way of example, FIGS. 32A and 32B schematically depict a cartridge 3200 in accordance with some embodiments in which two sensors 3202, 3204 are incorporated. Each of the sensors can be constructed in a manner discussed above. For example, as shown schematically in FIG. 32B, sensors 3202 and 3204 include, respectively, sensing elements 3202 a and 3204 a. These sensing elements may include as a plurality of carbon nanotubes, graphene and/or other fullerenes. A plurality of metallic pads 3202 b and 3204 b are electrically coupled to the sensing element 3202 a/3204 a, respectively, to allow reading variation of at least one electrical property of the sensing element(s), e.g., electrical resistance, in response to interaction with one or more species in a food sample.

Without any loss of generality, in the present embodiment, one of the sensors (e.g., sensor 3202) includes a graphene layer that is functionalized with an anti-gliadin antibody in a manner discussed above. The other sensor (e.g., sensor 3204) also includes a graphene layer. But the graphene layer of the sensor 3204 may be functionalized with an isotype of the anti-gliadin antibody employed to functionalize the sensor 3202. The isotype antibody is similar to the anti-gliadin antibody except that it does not selectively bind to gliadin. In some embodiments, the graphene layer of one sensor can be functionalized with one gluten protein and the graphene layer of the other sensor can be functionalized with another gluten protein.

The sensors 3202/3204 are configured such that they can concurrently, or sequentially, receive different portions of a sample under study to determine the presence (or the probability of the presence) of one or more species of interest in the sample. In this embodiment, the signal generated by the sensor 3204 in response to interaction with a food sample is employed as a calibration signal against which the signal generated by the sensor 3202 is evaluated.

C. OLEOPHOBIC HYDROPHOBIC FILTERS

Some embodiments use oleophobic filters. In some embodiments, an oleophobic filter can be concurrently hydrophilic or hydrophobic.

There is a need in a variety of applications for separating constituents of a sample. In particular, there is a need for enhanced filters and separation methods.

In one aspect, a filter is disclosed, which comprises a substrate, and a polymeric material applied to a top surface of the substrate, where said polymeric material comprises a polymer having the following chemical structure:

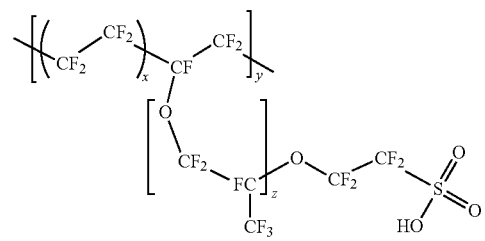

A variety of different substrates can be employed. For example, in some embodiments the substrate can be hydrophilic while in other embodiments the substrate can be hydrophobic. By way of example, in some embodiments, the substrate can comprise cellulose fibers.

In some embodiments, the filter can be concurrently oleophobic and hydrophilic. In some other embodiments, the filter can be concurrently oleophobic and hydrophobic. In some embodiments, the filter can be oleophobic but allow the passage of alcoholic solutions.

Figure 34A:
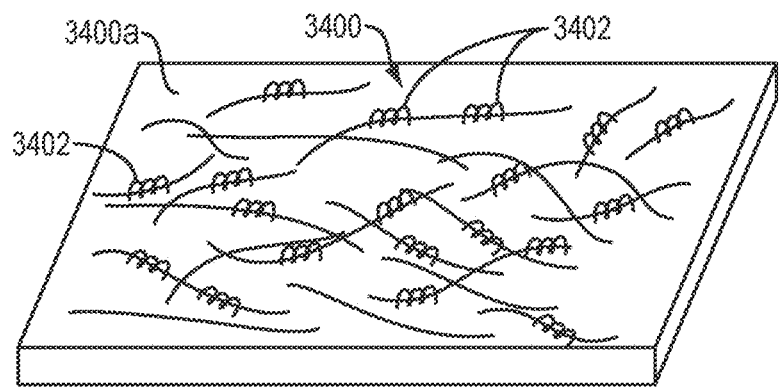
FIGS. 34A and 34B schematically depict a filter according to an embodiment.
Figure 34B:
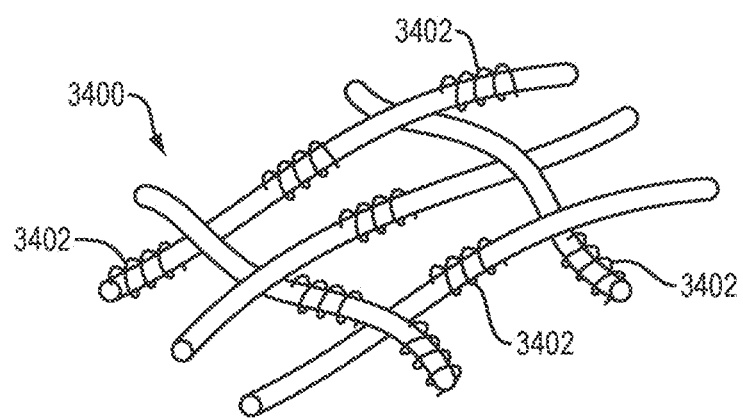

FIGS. 34A and 34B schematically depict a filter according to an embodiment of the present teachings, which includes a cellulose-based substrate 3400 having a top surface 3400 a that is treated with a polymeric material 3402. The substrate 3400 can be formed of a variety of different materials, which can exhibit hydrophobicity or hydrophilicity. In some other embodiments, the substrate may be formed of polytetrtaethylene (e.g., Teflon®).

In some embodiments, the substrate 10 is a porous substrate. By way of example, the substrate 10 can have pores with sizes in a range of about 1 micrometer to about 100 micrometers.

In some embodiments, the polymeric material 3402 is dispersed over the top surface 3400 a. While in some embodiments, the polymeric material 3402 can substantially cover the entire surface 3400a of the substrate 3400, in other embodiments, it can cover only portions of the surface 3400 a. Without loss of generality, in the following discussion, the substrate 3400 is assumed to have a porous cellulose structure.

In this embodiment, the polymeric material is sulfonated tetrafluoroethylene based fluoropolymer-copolymer. For example, the polymeric material can be ethanesulfonyl fluoride, 2-[1-[difluoro-[(trifluoroethenyl)oxy]methyl]-1,2,2,2-tetrafluoroethoxy]-1,1,2,2,-tetrafluoro, copolymer with tetrafluoroethylene. In some embodiments, the polymeric material can be tetrafluoroethylene-perfluoro-3, 6-dioxa-4-methyl-7-octenesulfonic acid copolymer.

An example of such a polymeric material is a polymer commonly known at Nafion®, which is marketed by Dupont Chemicals Company of Wilmington Del., U.S.A. Nafion® is a synthetic polymer with long strands of CF2 moiety as its backbone and branches of H-503, known as sulfonate, which can be a source of protons. Nafion® has the following molecular structure:

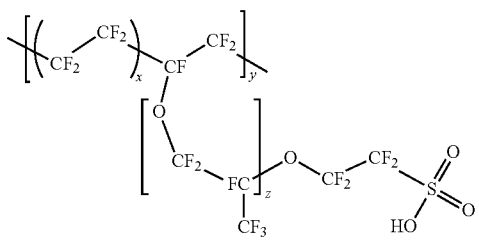

Without being limited to any particular theory, the Nafion® backbone is hydrophic, but under certain conditions the sulfonic functional groups can self-organize so as to create a plurality of channels through which water molecules can be transported.

As discussed further below, a filter according to the present teachings can be oleophobic, i.e., it can impede and preferably prevent the passage of fatty molecules through the filter. Without being limited to any particular theory, the CF groups of Nafion impart such oleophobic character to the filter. In addition, the cellulose substrate can be hydrophobic. Hence, the combination of Nafion and the cellulose substrate can provide a filter that is concurrently oleophobic and hydrophic.

In some embodiments, the filter can impede the passage of fatty molecules but allow the passage of alcohol (e.g., methanol or ethanol), or an aqueous solution of alcohol through the filter.

A filter according to the present teachings can be used in a variety of different applications. For example, as discussed above, the filter can be employed in a cartridge according to the present teachings for detecting the presence of an analyte, e.g., a gluten protein, in a food sample.

In some exemplary embodiments, Cellulose filter papers with a porosity of 200 were obtained from Sigma Aldrich (GE filter 42). Each filter paper was used as a supporting substrate onto a surface of which Nafion® was applied.

In order to obtain a substantially uniform distribution of the Nafion particles on the cellulose filter surface, ink spraying method was used for applying the Nafion dispersion onto the cellulose filter surface. More specifically, the cellulose filter paper was placed in a tubular structure with a substantially uniform diameter of D (approximately 2-3 inches) and a length of equal to or greater than 10 D. An exhaust fan was placed downstream of the tubular structure so as to generate a negative pressure in the upstream of the flow.

More specifically, the filter paper was introduced into a conduit provided by the tubular structure and was secured in its place at a length of about 2D from downstream end side of the conduit. To prevent the filter paper from bulging and possibly rupturing the surface of the holder, a fine metallic mesh was placed around the holder to secure the filter. At a distance of D from the inlet of the conduit, a spraying nuzzle was disposed to ensure uniform application of the Nafion particles onto the filter surface. The spray nozzle was then used to coat the exposed surface of the filter paper with the aforementioned Nafion® dispersion.

The coated filter was kept in an oven maintained at a temperature of 86° C. for 1 hour so as to form more stable bonds between Nafion® and cellulose structures.

Figure 35A:
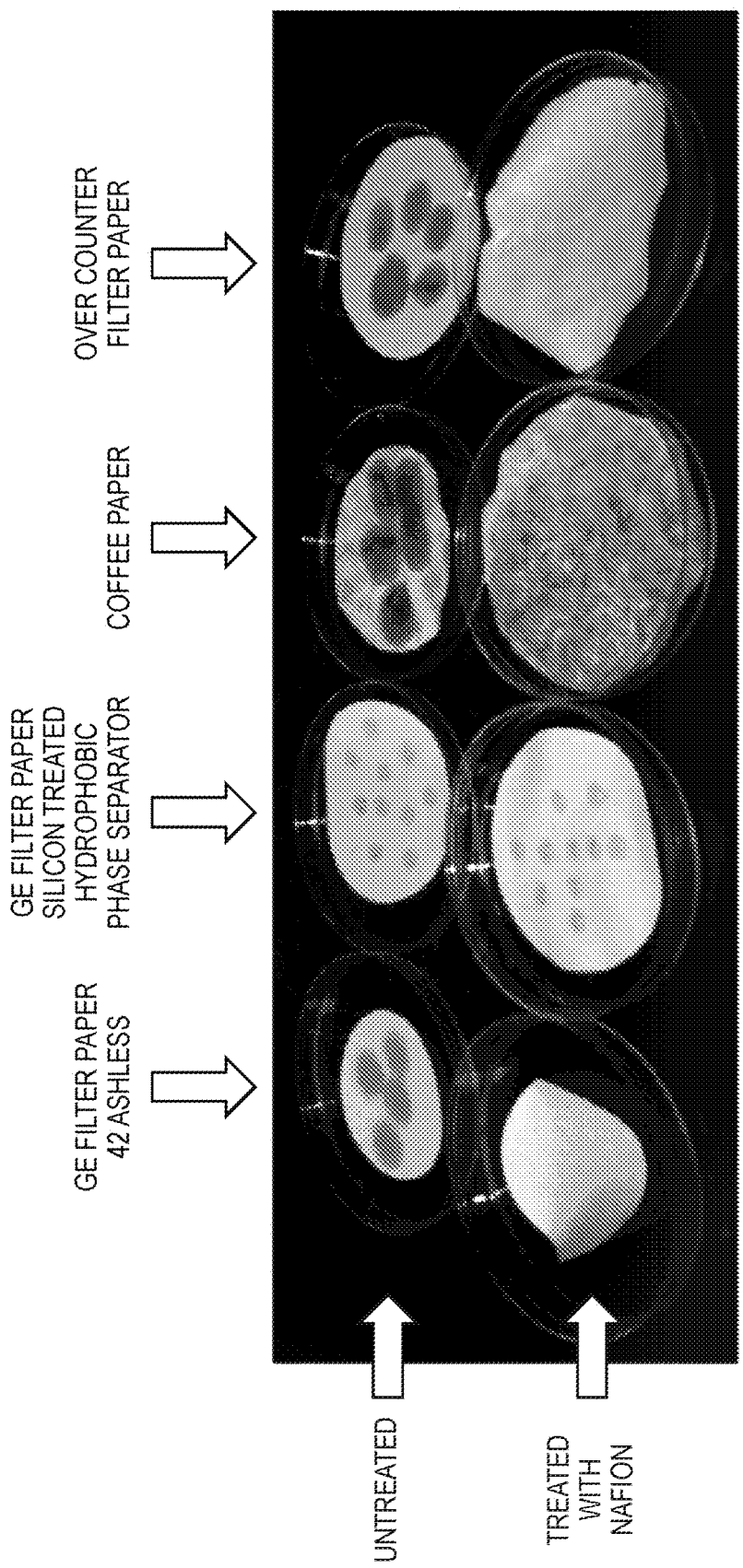
FIG. 35A shows an image of untreated and Nafion-treated GE filters when exposed to cooking oil.
Figure 35B:
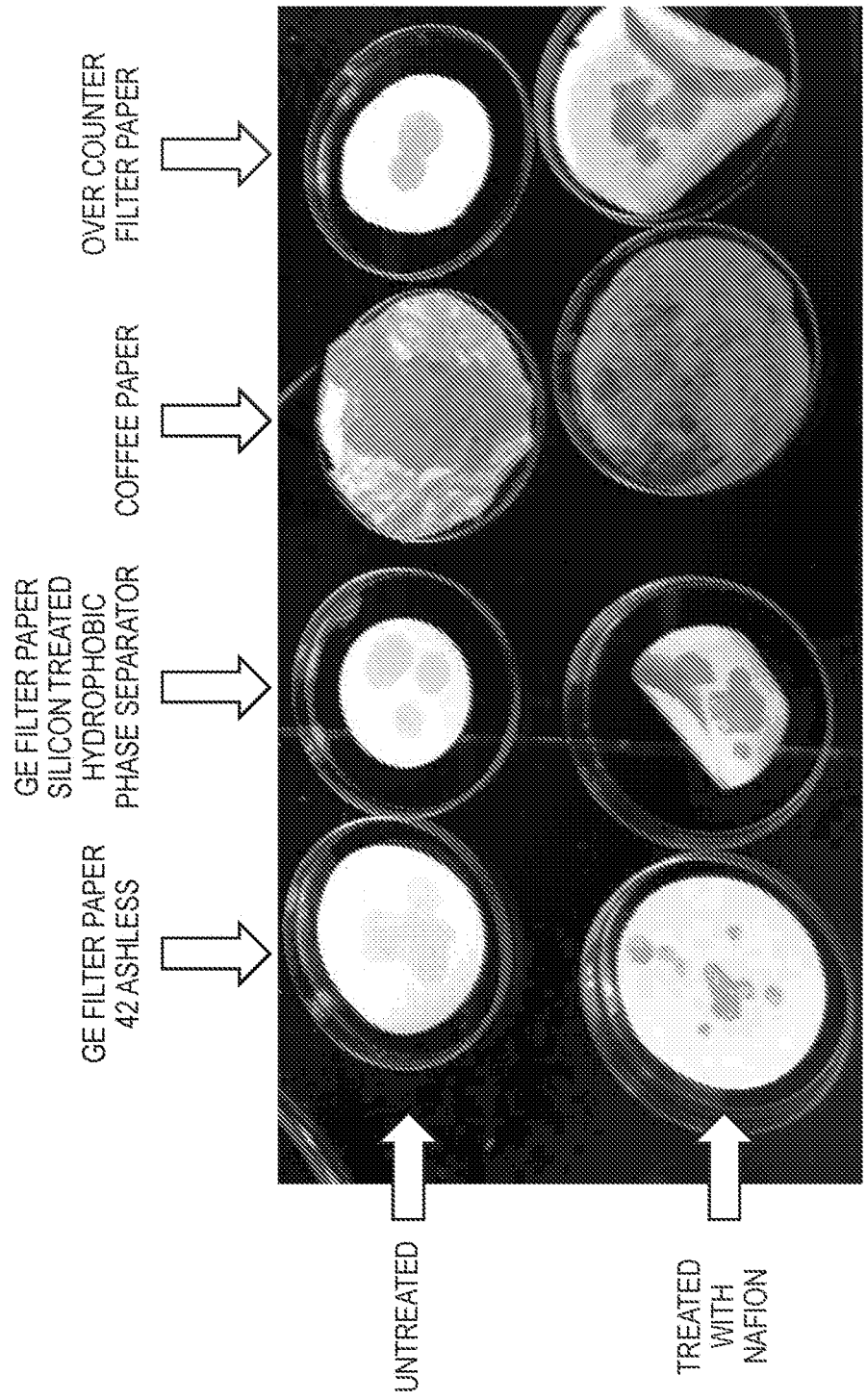
FIG. 35B shows images of untreated and Nafion-treated GE filters when exposed to ethanol.
Figure 35C:
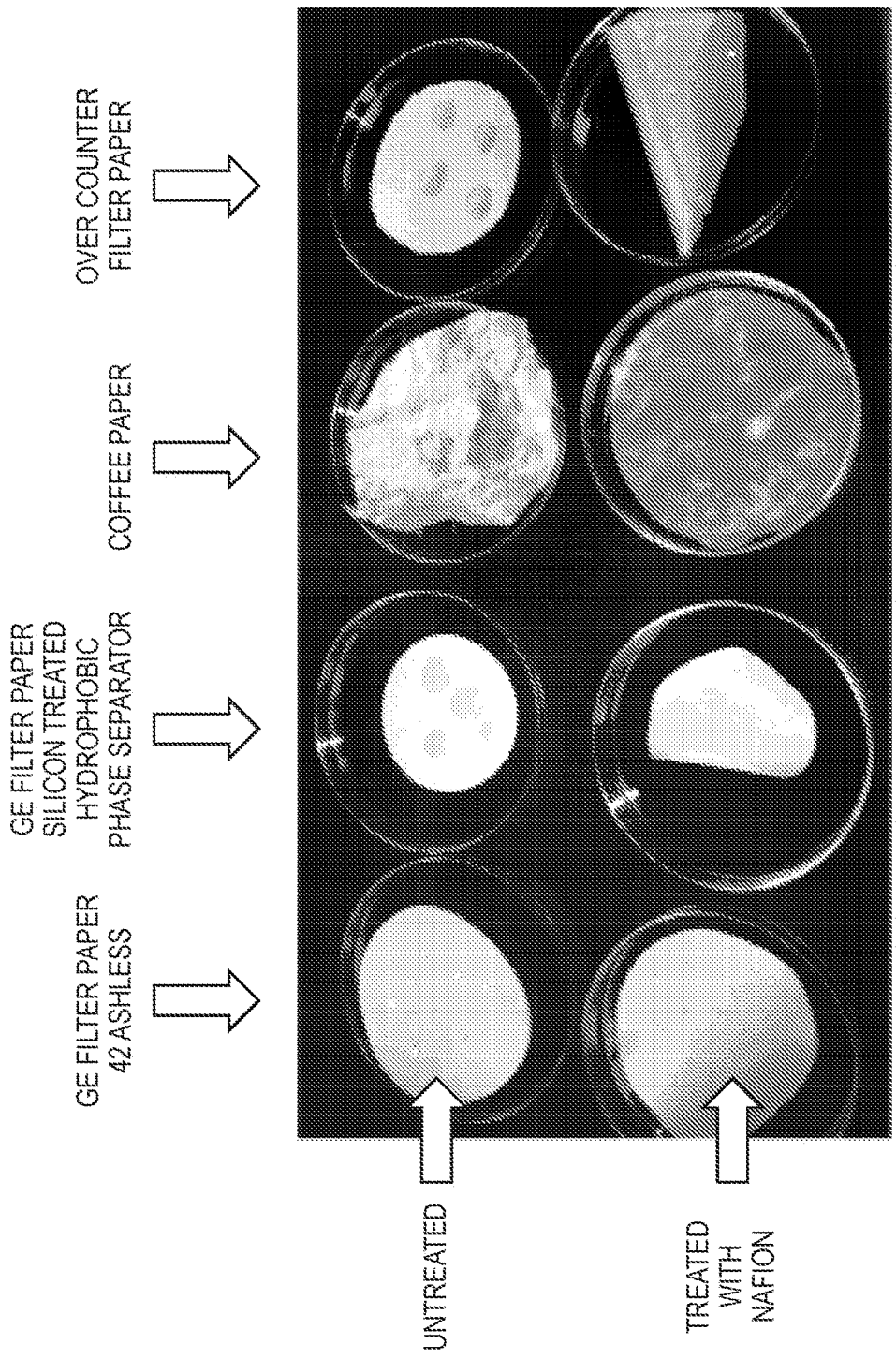
FIG. 35C shows images of untreated and Nafion-treated GE filters when exposed to deionized (DI) water.

FIG. 35A shows an image of untreated and Nafion-treated GE filters when exposed to cooking oil. FIG. 35B shows images of untreated and Nafion-treated GE filters when exposed to ethanol. FIG. 35C shows images of untreated and Nafion-treated GE filters when exposed to deionized (DI) water. The images show that the Nafion-treated filters prevent passage water as well as oily substances while allowing ethanol to pass through.

D. PROCESSING AND DETECTION SYSTEMS

Some embodiments employ a processing and detection system to detect presence of a molecule, such as a gluten protein, in a food sample. In some embodiments, the processing and detection system includes a food processor and a detector. In some embodiments, the food processor is configured to receive a food sample and process it by mixing it with a process liquid and extracting a processed food liquid, which can be analyzed by the detector. In some embodiments, the detector includes a cartridge, which can analyze the processed food liquid and detect presence of the molecule in the processed food liquid.

FIGS. 36A-36D schematically depict a food processor 3600 according to an embodiment. The food processor 3600 includes a tubular body 3602, a plunger 3606, a liquid reservoir 3614, and a strainer plate 3616.

As further detailed below, the tubular body 3602 is configured to receive a solid food sample. The plunger 3606 is configured to push and crush the received food sample inside the tubular body 3602. The liquid reservoir 3614 contains a process liquid for processing the crushed food sample. The strainer plate 3616 is configured to hold the liquid reservoir 3614 at a distal end of the tubular body 3602, and enables the plunger to puncture and squeeze the liquid reservoir and cause the crushed food sample to mix with the process liquid.

One or more of the tubular body 3602, the plunger 3606, and the strainer plate 3616 can be manufactured using methods such as injection molding method using polyurethane plastics.

The tubular body 3602 is in the form of a hollow cylinder having a proximal end 3602 *a* and a distal end 3602 *b*. The tubular body 3602 has an opening 3604 at the proximal end 3602 *a* for receiving the plunger 3606. Moreover, the peripheral cylinder of the tubular body 3602 forms a sample opening 3603 for receiving the sold food sample.

The plunger 3606 extends from a proximal end 3606 *a* to a distal end 3606 *b*. At the proximal end 3606 *a*, a disk 3608 is attached to the plunger 3606. The disk 3608 allows a user to push the plunger into, or retract the plunger from, the hollow tube 3602. The distal end 3606 *b* of the plunger forms a pressing surface that is configured to press on the food sample or on liquid reservoir 3614, as detailed below. The pressing surface contains a plurality of pins 3610 disposed on the plunger 3606 for facilitating the crushing of the food sample, as discussed below in more detail.

In some embodiments, the pins 3610 can have conical, pyramidal, or other shapes that provide a sharp tip for facilitating the crushing of the solid food sample introduced into the tubular body 3602. A pin may have a cylindrical body (A) and a conical tip (B). The pins can be formed of any suitable material. By way of example, in some embodiments, the pins can be formed of a metal, such as stainless steel. In other embodiments, the pins can be formed of other materials, such as plastic.

Referring again to FIGS. 36A-36D, the plunger 3606 can be pulled back beyond the opening 3603 to allow the introduction of the food sample into the interior of the cylinder of the tubular body 3602 via the opening 3603.

Figure 36C:
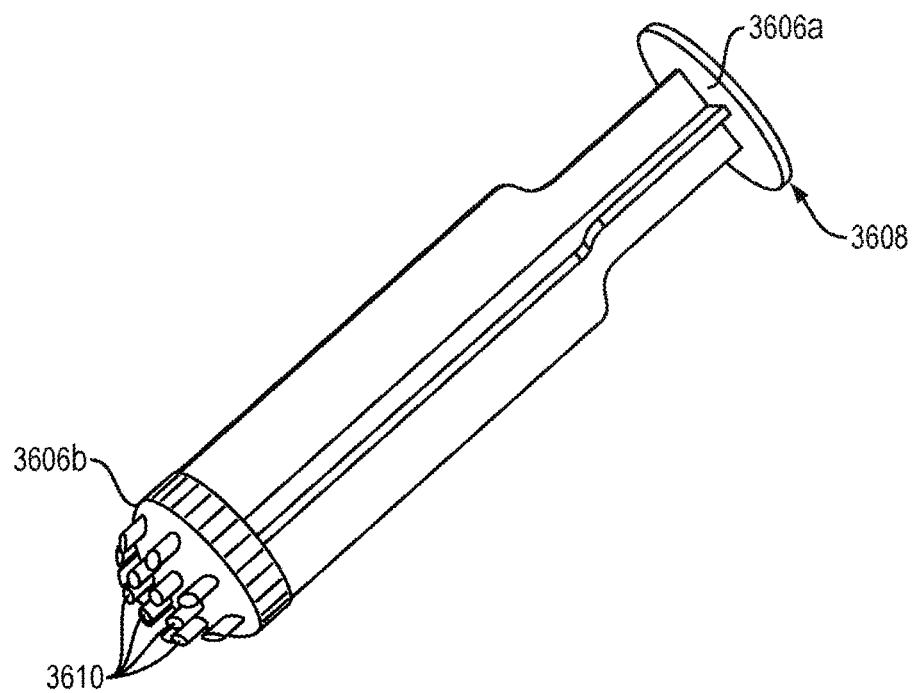
Figure 36D:
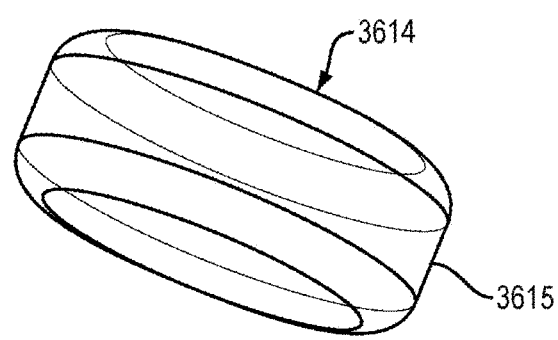

The liquid reservoir 3614 contains a process liquid 3615 and is disposed in the hollow tubular body 3602 close to its proximal end 3602 b. As shown in FIG. 36D, in this embodiment, the liquid reservoir 3614 is in the form of a bag that is placed within the hollow cylinder of the tubular body 3602. The liquid reservoir 3614 can be maintained within the tubular body 3602, e.g., via a friction fit or other known mechanisms. In this embodiment, the liquid reservoir 3614 is formed of a soft polymeric material. Some examples of suitable polymeric materials include, without limitation, polyurethane, low density polyethylene (LDPE), polyvinyl chloride, polyisobutane (PIB), and poly (ethylene-vinylacetate). The wall of the liquid reservoir 3614 may be sufficiently thin so that it can be punctured by the pins 3610 as the user pushes the plunger into the hollow cylinder and presses the pins against the bag. By way of example, the thickness of the bag's wall can be in a range of about 0.0002 inches to about 0.001 inches, e.g., about 0.0005 inches.

The strainer plate 3616 is disposed between the liquid reservoir 3614 and the distal end 3602 b of the tubular cylinder. Moreover, the strainer plate 3616 is disposed such that a cavity 3620 remains between the strainer plate and the distal end 3602 b. The strainer plate 3616 forms a plurality of through openings or holes 3618, each of which is configured to receive one of the pins 3610. When the plunger 3606 is pushed through the hollow cylinder, the pins 3610 may pierce the bag and reach the openings 3618. Further, the pins 3610 may proceed through the openings 3618, thus allowing the distal end 3606 b of the plunger to squeeze the liquid out of the liquid reservoir 3614.

In various embodiments, the strainer plate 3616 may be formed as a separate unit and then fitted in the tubular body 3602, or it may be made as an integral unit with the rest of the tubular body 3602.

The cavity 3620 separates the strainer plate 3616 from a nozzle 3622 disposed at the distal end 3602 b of the hollow cylinder 3602. As discussed in more detail below, the use of the food processor results in the accumulation of at least a portion of the process liquid in the cavity 3620, which can be subsequently injected into a cartridge.

More specifically, when using the food processor 3600, a user may initially pull back the plunger 3606 such that the plunger 3606 is positioned between opening 3603 and proximal end 3602 a. The user can then introduce a food sample into the tubular body 3602 via the opening 3603, and push the plunger 3606 toward the bag 3614. After the distal end 3606b of the plunger reaches the bag 3614, the user may continue to press the plunger towards the distal end 3602 b and against the bag 3614. This pressing may cause the pins 3610 to pierce the bag to release the process liquid contained in the bag. The process liquid interacts with the food sample to extract an analyte of interest that may be present in the food sample. For example, when the analyte of interest is gliadin, the process liquid can be a mixture of alcohol and water. As discussed above, such a mixture can dissolve gliadin therein.

In some embodiments, when the food sample is a solid, the pressing of the plunger against the bag 3614 may also cause crushing of the food sample by the distal end 3605 b, including pins 3610. The food sample can be crushed as the pins 3610 press against the liquid bag 3614, pierce the bag, or engage with the openings 3618. The crushing of the food sample can provide more surface area for the interaction of the process liquid with the food sample, thereby facilitating the extraction of the analyte of interest from the food sample. More specifically, as the pins enter the openings 3618 of the strainer plate 3616 the food sample is further crushed mixed with the process liquid. The liquid part of the resulting mixture, here called the processed food liquid, which may contain the analyte of interest via interaction with the food sample, can enter the cavity 3620.

Figure 37A:
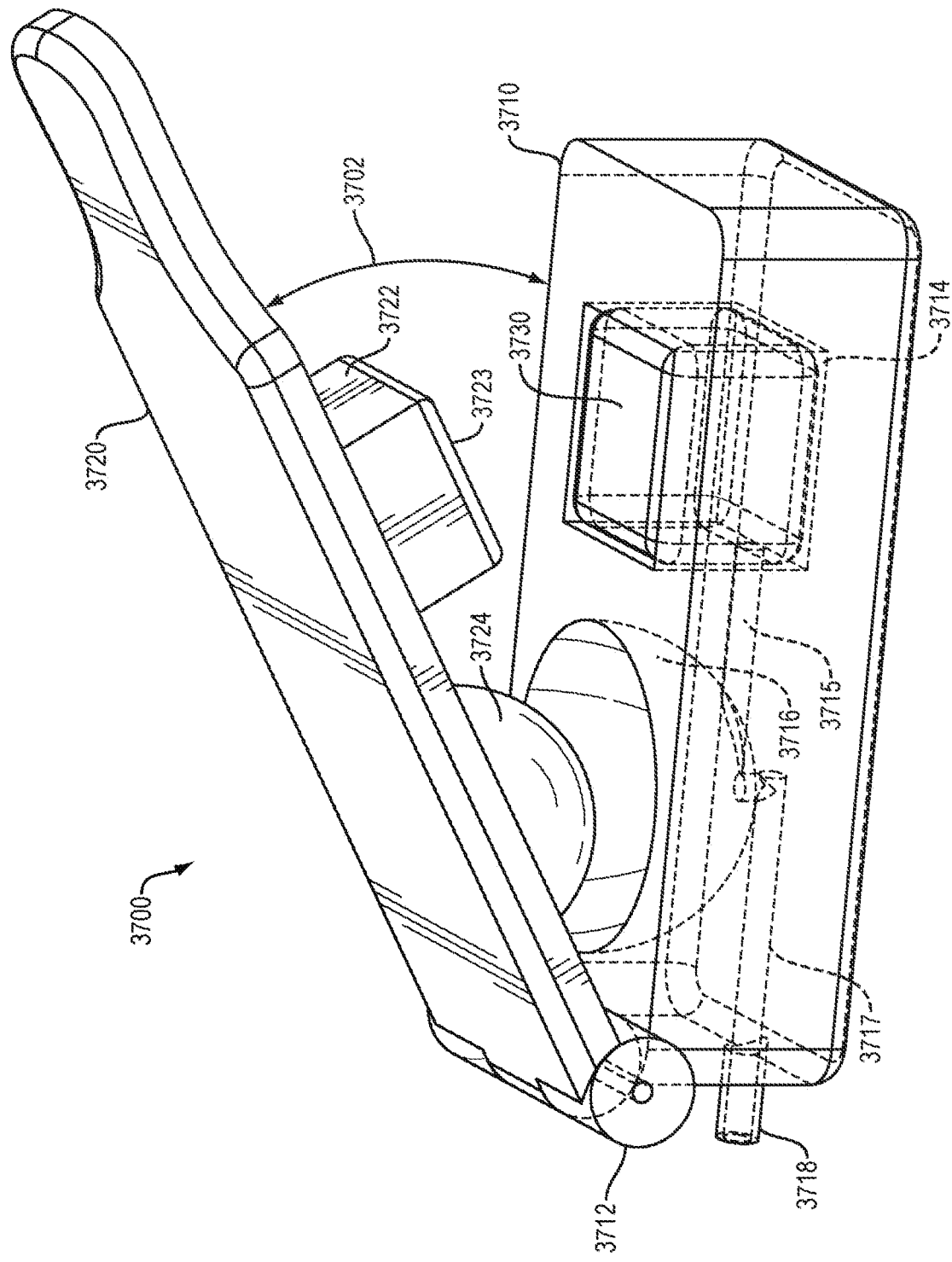
FIGS. 37A-C schematically depict a food processor according to another embodiment.

FIG. 37 schematically depicts a food processor 3700 according to another embodiment. The food processor 3700 includes a body 3710, an arm 3720, and a liquid reservoir 3730. Different parts of food processor 3700 may be made of a variety of different materials and using different manufacturing methods. By way of example, each of body 3710 and arm 3720 may be formed of a plastic using injection molding or other suitable techniques.

Liquid reservoir 3730 may contain a process liquid for processing the food sample. Liquid reservoir 3730 may be in the form of a bag fabricated of a soft polymeric material such as polyurethane or other suitable polymeric materials. The bag's wall can be sufficiently thin, e.g., it can have a thickness in a range of about 0.0005 inches More generally, the bag's wall may have a thickness or a weakened section, which allows a user to use a pressing or puncturing mechanism, as detailed below, to puncture the bag by exerting a moderate pressure on the bag. The pressure may be in a range of about 1 psi to about 3 psi. While in general a plurality of different process liquids can be stored in reservoir 3730, in some embodiments the process liquid can be alcohol or an aqueous solution of alcohol. As discussed earlier, when a food processor is employed together with a cartridge for detecting gluten in a food sample, the alcohol can dissolve one or more gluten proteins, if any, in the food sample under study. In some embodiments, reservoir 3730 can have a liquid volume in a range of, e.g., from about 0.5 ml to about 1 ml.

Body 3710 includes a hinge 3712, a reservoir enclosure 3714, a liquid channel 3715, a food chamber 3716, a processed liquid channel 3717, and an exit port 3718. Hinge 3712 is configured to provide a hinge between body 3710 and arm 3720. Reservoir enclosure 3714 is configured to house liquid reservoir 3730. Liquid channel 3715 connects reservoir enclosure 3714 to food chamber 3716. Liquid channel 3715 is configured to provide a conduit for the process liquid to flow from reservoir enclosure 3714 to food chamber 3716. Food chamber 3716 is configured to contain a food sample that can be, for example, solid, liquid, or a sold-liquid mixture. Processed liquid channel 3717 connects food chamber 3716 to exit port 3718. Processed liquid channel is configured to provide a conduit for a processed food liquid to flow to exit port 3718 after it is generated in food chamber 3716. Exit port 3718 provides a conduit for the processed food liquid to exit body 3710 and, for example, enter a cartridge, as further detailed below.

Figure 37B:
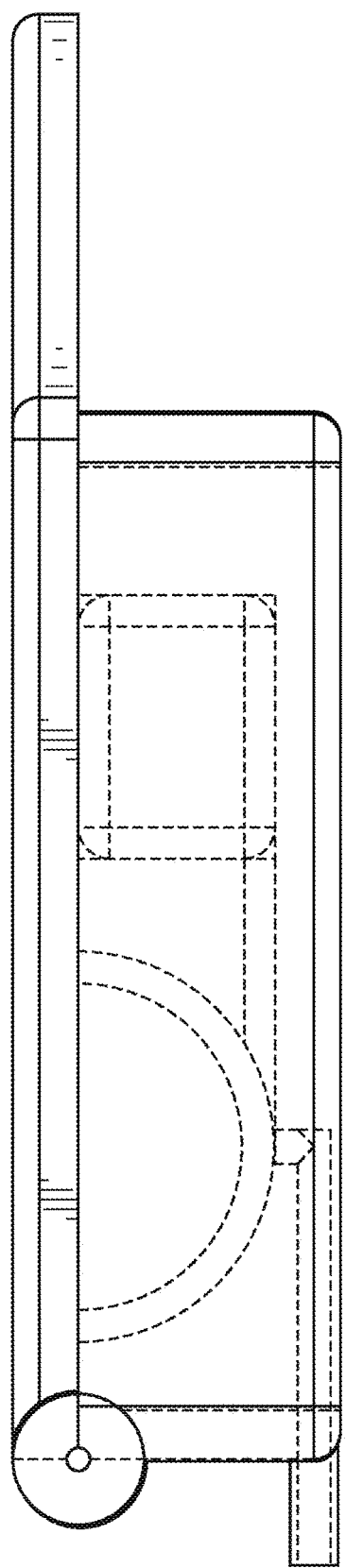
Figure 37C:
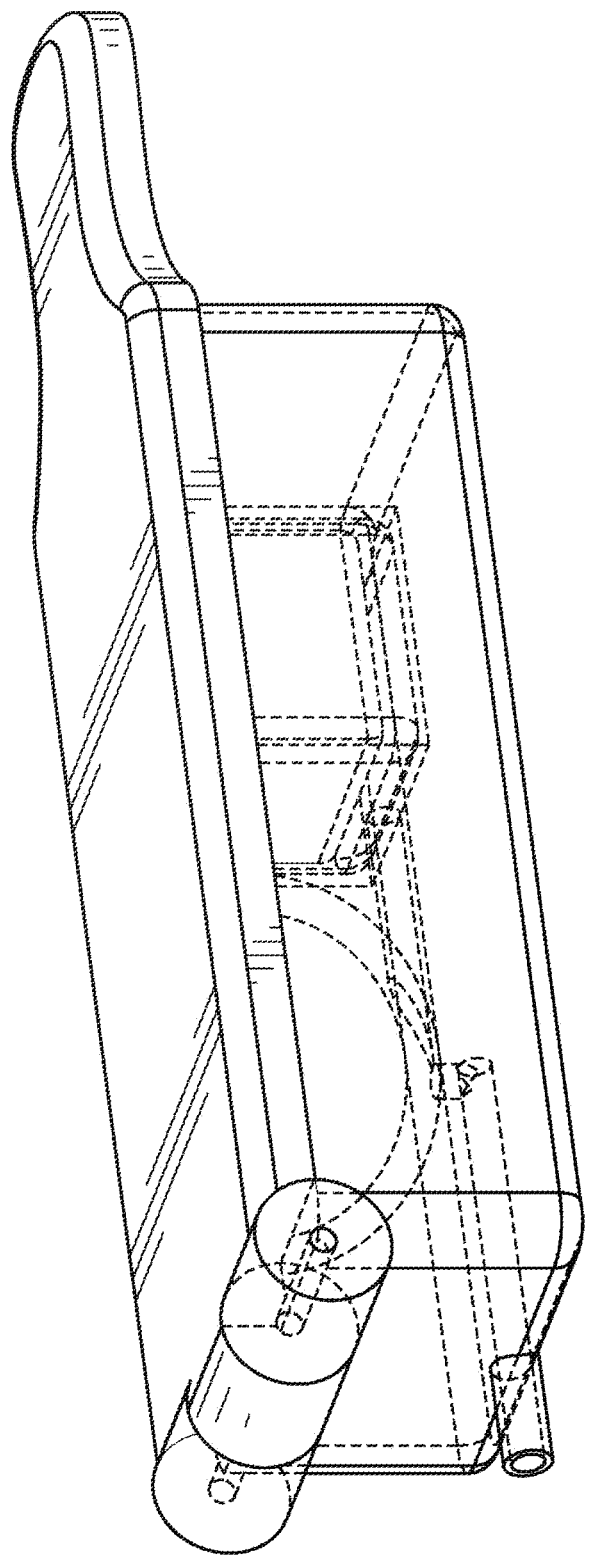

In food processor 3700, body 3710 and arm 3720 are elongated. Further, hinge 3712 hingedly attaches body 3712 to atm 3720. In different configurations, arm 3720 rotates about hinge 3712, such that the elongation axes of the two form different angles, shows as angle 3702. For example, to close food processor 3700, arm 3720 is lowered to rest on body 3710, such that angle 3702 is approximately zero. FIGS. 37B and 37C show two views of a closed food processor 3700 according to an embodiment.

To open food processor 3700, on the other hand, arm 3720 is rotated away from body 3710 to form a non-zero angle 3702, such as the one shown in FIG. 37. In the open configuration, food chamber 3716 may receive the food sample.

Arm 3720 includes a protrusion 3722 and a food grinder 3724. Protrusion 3722 and food grinder 3724 are positioned along arm 3720 such that when the food processor is closed, protrusion 3722 enters reservoir enclosure 3714, and grinder 3724 enters food chamber 3716.

Reservoir enclosure 3714 may have a shape and dimensions that snug fits liquid reservoir 3730. In food processor 3700, for example, both liquid reservoir 3730 and reservoir 3714 have cuboid shapes, with the latter having slightly larger dimensions. Moreover, protrusion 3722 may have a similar shape, such that, when the food processor is closed, protrusion 3722 presses down upon liquid reservoir 3730 and forces it to rupture. In particular, protrusion 3722 may include a pressure surface 3723, which contacts and presses on liquid reservoir 3730 during the closing. In the embodiment shown in FIG. 37, pressure surface 3723 is the lower surface of the cuboid that forms protrusion 3722. In some embodiments, pressure surface 3723 may have other shapes or include other parts, such as sharp pins, to facilitate the rupturing of liquid reservoir 3730.

Also, grinder 3724 may have a shape that partially or fully fills the volume inside food chamber 3716 when the food processor is closed. Closing food processor 3700 thus causes grinder 3724 to press or grind a solid sample food that may be in food chamber 3716. Moreover, this pressing may facilitate mixing of the sample food and any process liquid that may be in food chamber 3716. In food processor 3700, for example, food chamber 3716 is shaped as a hollowed sphere portion. Food grinder 3724, on the other hand, is also shaped as an inverted solid sphere portion, such that it substantially fits inside food chamber 3716 when food processor 3700 is closed. Other embodiments may employ other shapes for reservoir enclosure 3714, food chamber 3716, protrusion 3722, and food grinder 3724.

In some embodiments, a user may use a food processor such as food processor 3700 by performing two stages, a placement stage, and a grinding and mixing stage.

In the placing stage, the user may open food processor 3700 by rotating arm 3720 around hinge 3712 such that angle 3702 increases. After that, the user may place a food sample, e.g., a solid food sample, inside food chamber 3716. In various embodiments, liquid reservoir 3730 may already be placed inside reservoir enclosure 3714 or may be placed there by the user during the placing stage.

After the placing stage, the user may perform the grinding and mixing stage. In this stage, the user closes the food processor by rotating arm 3720 about the hinge 3712 to decrease angle 3702. During this closing, pressure surface 3723 may come into contact with the surface of liquid reservoir 3730. The user may further press arm 3720 in a direction of reducing angle 3702 and thus pressing pressure surface 3723 on liquid reservoir 3730. This pressure may rupture liquid reservoir 3730 and release the process liquid to flow to food chamber 3716 through liquid channel 3715.

Moreover, the pressure of arm 3730 may also cause food grinder 3724 to press down on the food sample in food chamber 3716. If the food sample is solid, this pressure may grind or press it. This may increase the surface area of the food sample and cause it to better mix with the in-flowing process liquid. In some embodiments, the surface of grinder 3724 can be textured in a way that facilitates the grinding, crushing, or mixing of the food sample. A textured surface may be, for example, a roughed surface or a surface with a plurality of spikes.

During the grinding stage, in food chamber 3716, the process liquid may interact with the food sample to generate a processed food mixture. This interaction may extract an ingredient of the interest from the food sample to generate a mixture of the process liquid and that ingredient. For example, when the ingredient of interest in a gluten protein, the process liquid may include alcohol (e.g., it can be an aqueous solution of alcohol). The alcohol in the process liquid can dissolve at least a portion of gluten in the food sample, thereby generating a processed food mixture that contains gluten. The processed food mixture may have a liquid part, called the processed food liquid, which can flow through processed liquid channel 3717. The processing liquid may dissolve the food sample in full and create a solution. In this case, the processed food liquid may be all or part of the resulting solution, which flows through processed liquid channel 3717. The processing liquid may also dissolve the food sample in part and create a sold-liquid mixture. In this case, the processed food liquid may be some or all of the liquid part in the mixture, which flows out of food chamber 3716 and through processed liquid channel 3717.

After the grinding and mixing stage, the processed food liquid can flow out of food processor 3700 through exit port 3718. The processed food liquid may, for example, enter a cartridge. In some embodiments, the cartridge may have an input port coupled to exit port 3718 of food processor 3700. The cartridge may, for example, be configured to detect a protein such as gluten.

Food processor 3700 may have a variety of sizes. By way of example, in some embodiments, body 3710 may have a length (L1) in a range of, e.g., about 0.75" to about 1.25", a width (W1) in a range of, e.g., about 0.5" to about 0.75", and a height (H1) in a range of, e.g., about 0.2" to about 0.3". Arm 3720 may have a length (L2) in a range of, e.g., about 1" to about 1.25".

FIGS. 38A-38E show five examples of processing and detection system s 3800, 3850, 3860, 3870, and 3880 for food samples according to different embodiments. Systems s 3800, 3850, 3860, 3870, and 3880 each include a food processor 3810 and a cartridge 3820. Food processor 3810 is configured to receive a food sample, have it interact with a process liquid, and extract a processed food liquid, e.g., liquid 3830, resulting from the interaction. In processing and detection system 3860 and 3870, on the other hand, food processor 3810 is similar to food processor 3700 of FIG. 37. The food processor may also be of other forms.

In each system, cartridge 3820 is configured to receive processed food liquid (e.g., liquid 3830) and detect the presence of molecule of interest. In some embodiments, cartridge 3820 includes at least one sensor that performs the detection. Further, in some embodiments, cartridge 3820 also includes an input port that is coupled to an output port of food processor 3810 to receive the processed food liquid.

In various embodiment, cartridge 3820 may be similar to one or more of the cartridges discussed above. In some embodiments, cartridge 3820 detects presence of at least one gluten protein in the processed food liquid. In some embodiments, cartridge 3820 generates at least one electrical signal that indicates the presence of the molecule, e.g., at least gluten protein. In some embodiments, the electrical signal may also indicate other information, such as the amount of the molecule, e.g., its concentration.

Figure 38B:
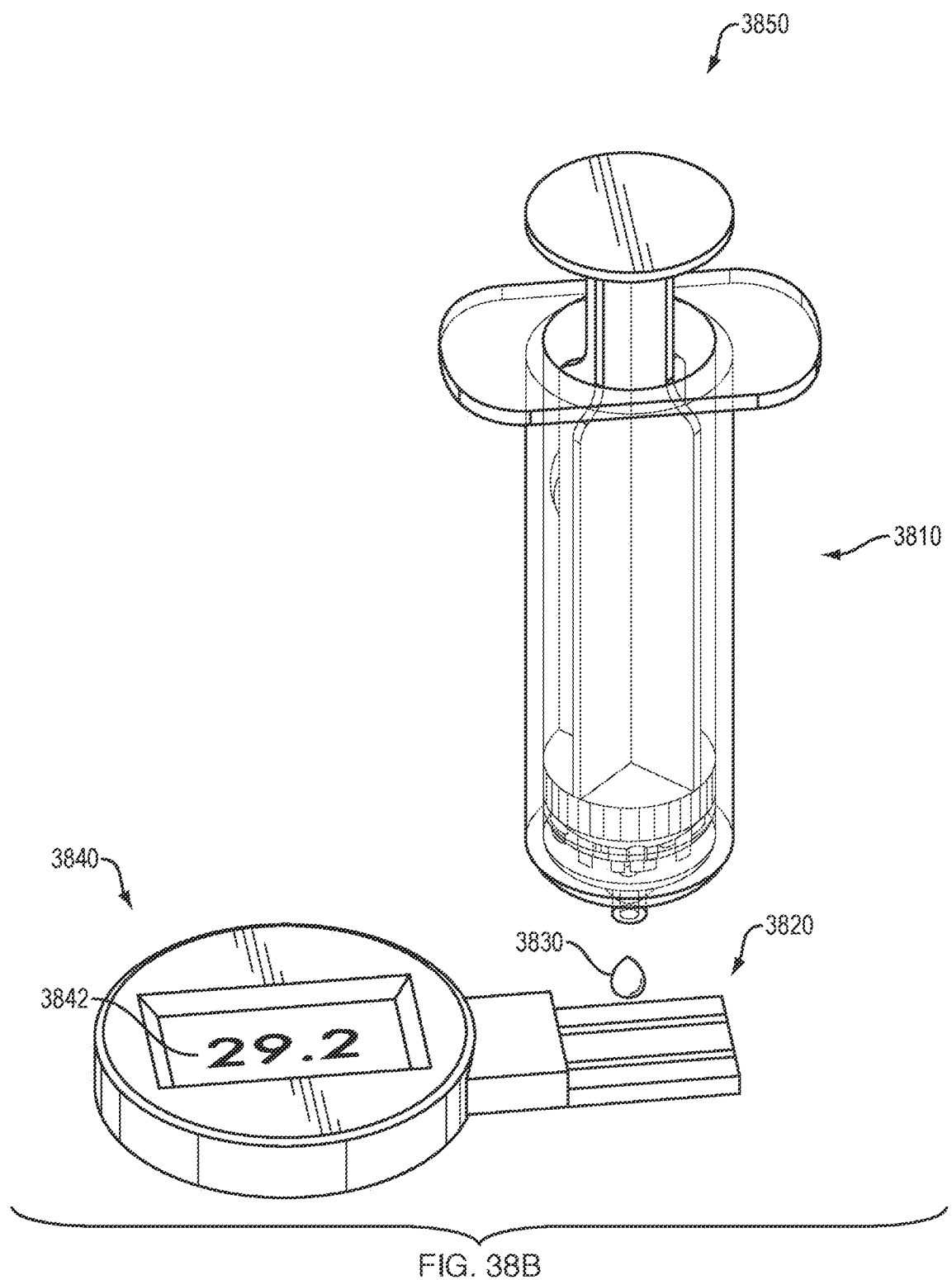
Figure 38C:
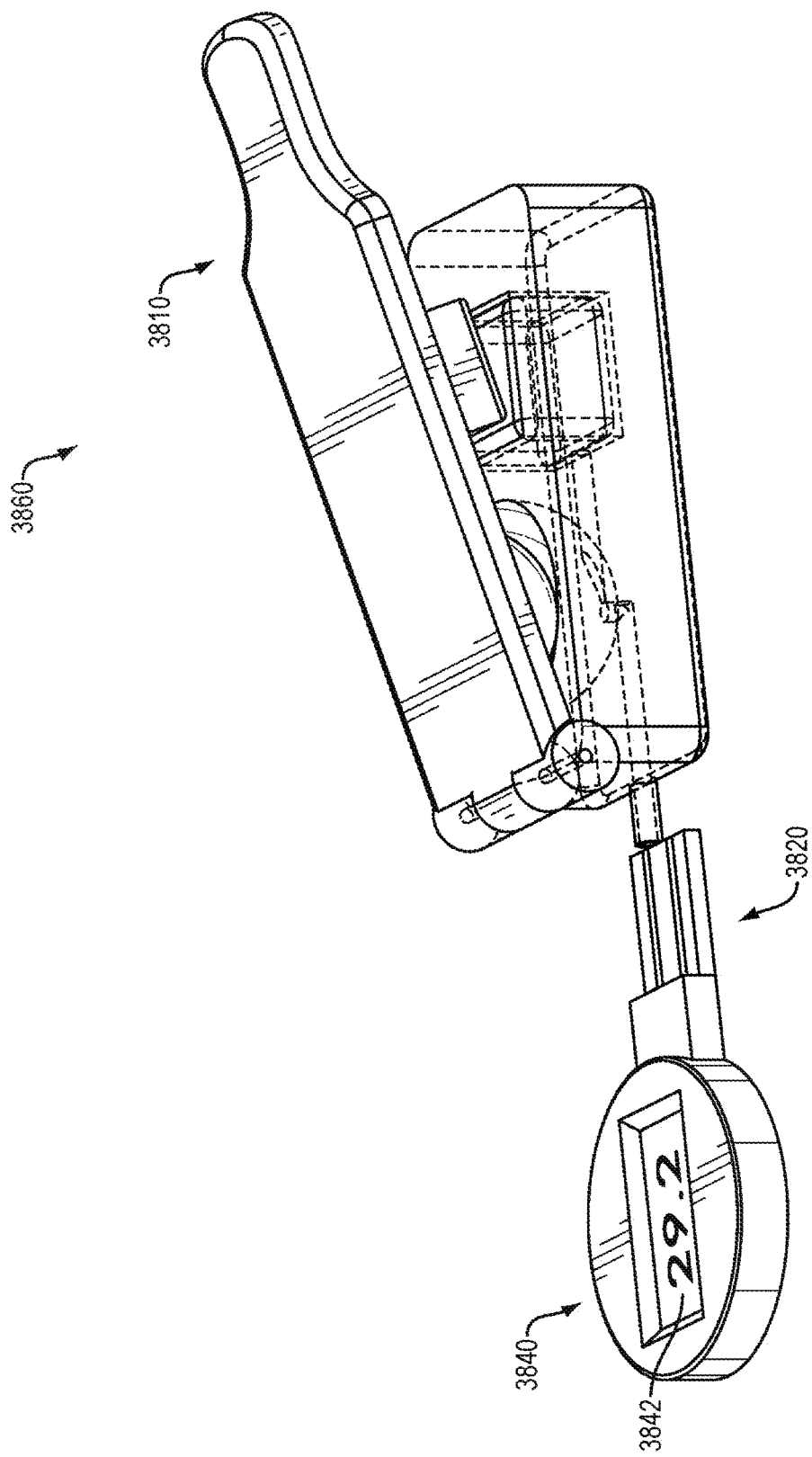
Figure 38D:
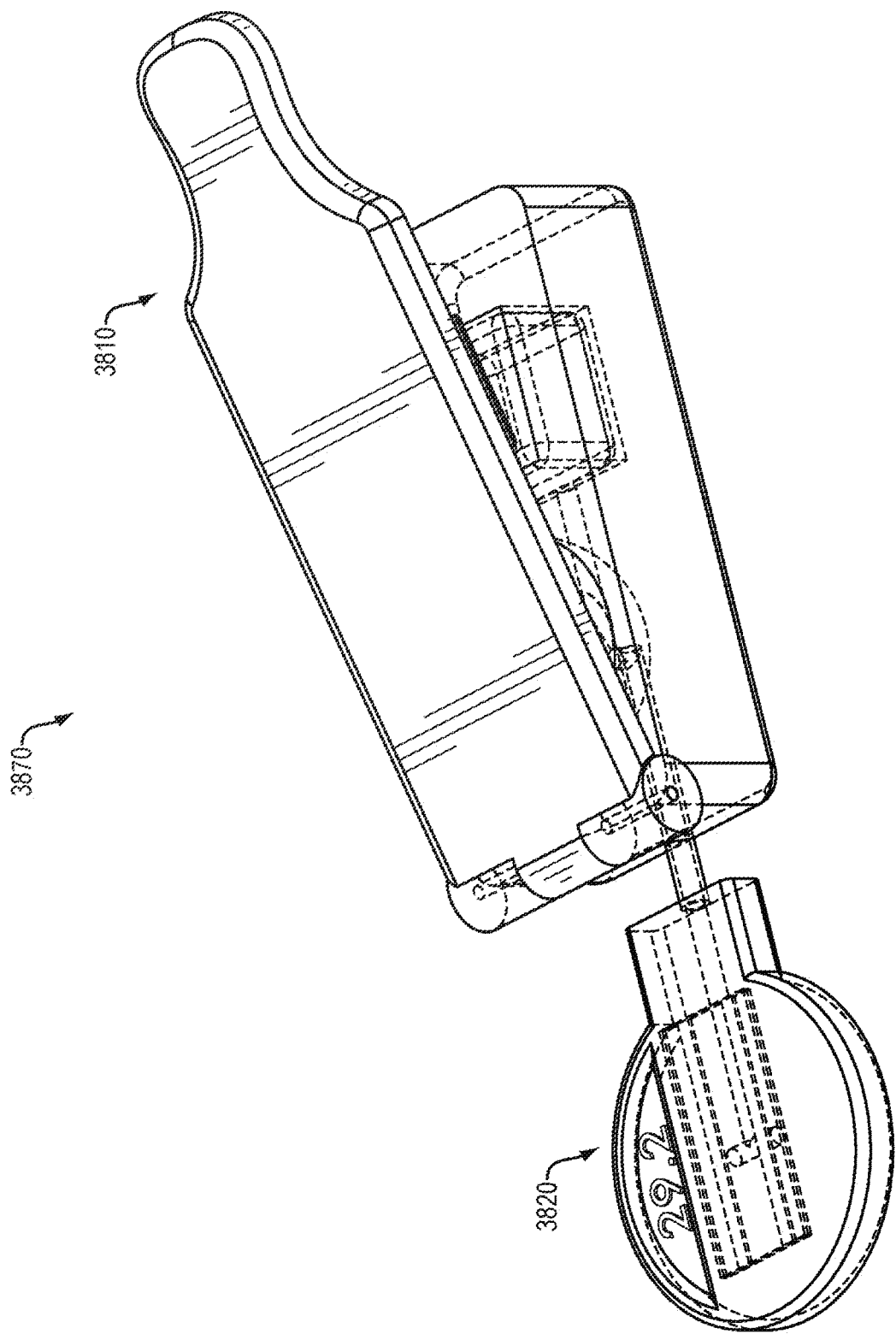

Systems 3850 and 3860 of FIGS. 38B and 38C further include an analyzer 3840. In system 3870, the analyzer may be part of cartridge 3820. Analyzer 3840 may be configured to receive the electrical signal generated by the cartridge, analyze the signal to determine the presence of the molecule of interest, and further display the results on a display 3842. In some embodiments, the analyzer may further determine from the electrical signal other information, e.g., the concentration of the molecule, and show that information on display 3842.

In various embodiments, a processing and detection system may be packed and distributed as one unit, or may be packed and distributed in separate sub-units. In some embodiments, for example, two or more of the food process, the cartridge and the analyzer may be included in one package. In some other embodiments, the cartridge and the analyzer may be included in one package that is separate from the food processor. The food processor may be, for example, disposable. The system may use a disposable food processor for one or a few times of detection, before replacing the food processor with a new food processor. Each food processor can function with the same cartridge. In some embodiments, one or more of the used food processors are configured such that the exit port for each of them can couple to an input port in the cartridge. In some embodiments, the exit port and input port can couple if one of them can fit into the other.

It should be understood that the principles of operation of various embodiments of the wearable device discussed above can also be implemented in a system that is not wearable. For example, the analyzer can be implemented as a desktop device that can receive cartridges according to the present teachings for detecting, and optionally quantifying, an analyte of interest, e.g., a gluten protein, in a food sample.

Further examples are provided in the Appendices for further illustration of various aspects of the present teachings and to show the feasibility of implementing the teachings of the disclosure. These examples are provided only for illustrative purposes and are not intended to present necessarily the optimal ways of practicing the teachings of the disclosure or optimal results that can be obtained.

While several exemplary embodiments and features are described here, modifications, adaptations, and other implementations may be possible, without departing from the spirit and scope of the embodiments. Accordingly, unless explicitly stated otherwise, the descriptions relate to one or more embodiments and should not be construed to limit the embodiments as a whole. This is true regardless of whether or not the disclosure states that a feature is related to "a," "the," "one," "one or more," "some," or "various" embodiments. Instead, the proper scope of the embodiments is defined by the appended claims. Further, stating that a feature may exist or can exist indicates that the feature exists in one or more embodiments.

E. EXPERIMENTAL RESULTS FOR SOME EMBODIMENTS

This section includes an explanation of experimental setups and results based on some embodiments. Some embodiments use graphene. The honey comb lattice structure of this material enables functionalizing it with organic materials such as antibodies to detect targeted materials. Some of the experiments demonstrated the ability to detect Gluten family proteins by making graphene based sensor functionalized by antibody and transient measurement of ohmic resistance of the sensor. The results showed patterns of ohmic resistance by exposing the sensor to targeted protein samples.

Experimental Setup and Procedures
Materials:

1 g of 1-pyrenebutanoic acid succinimidyl ester with 95% purity was purchased from Sigma-Aldrich. Sheets of 5 cm×10 cm monolayer graphene coated PET were ordered from ACS materials and sliced into squares of 1 cm length. The mouse monoclonal [14D5] to Gliadin as Anti-Gliadin antibody [14D5] was purchased at the batches of 100 µg with concentrations of 1 mg/ml. Also anti-mouse IgG monoclonal [UPC-10] (Mouse IgG2A isotype control) was ordered from Sigma-Aldrich in batches of 1 mg, solution in 0.01 M phosphate buffered saline, pH 7.4, containing 1% bovine serum albumin and 15 mM sodium azide.

Sensor Fabrication:

Pieces of 1 cm by 1 cm of the coated PET sheets by CVD monolayer graphene were placed separately inside the Eppendorf tubes. Each tube was then filled with Methanol and washed by water. Then 1 ml of 5 mM 1-pyrenebutanoic acid succinimidyl ester in dimethylformamide (DMF) was added to the tubes for 2 hrs at room temperature. Tubes were washed after wards with pure DMF and later with DI water. Tubes were incubated with 5 µg/ml of Anti-Gluten antibody in Sodium Carbonate buffer, pH 9.0, overnight at 4 degrees. In the next morning the chips were rinsed with DI water and PBS. Tubes then filled with 0.1M Ethanolamine pH 9.0 and chips left for incubation for 1 hr at room temperature. Then, they were rinsed with 0.1% Tween 20 solution. The chips then were incubated in 0.1% Tween 20 solution for 1 hr at room temperature to passivate uncoated graphene area. After incubation with Tween 20, the tubes were filled with TBST+ 0.5% BSA (BLOCKING BUFFER) and left for 1 hr at room temperature. All chips then were rinsed by PBS and DI water and dried slowly in room temperature. The same protocol was applied for fabrication of sensors functionalized by anti-mouse IgG and IgM antibody.

Spectrophotometry:

The untreated chips were conjugated to HRP (1:2500 dilution) for 1 hr at room temperature, and then were washed by TBST 4 times. Then HRP was added to substrate's tube an allowed to develop for 5 minutes. The chips and sample then were read for A450 on spectrophotometer.

Galvanometric Measurements:

Two droplets of high conductive silver glue were placed on the corners of the chips and let them dry in room temperature for at least half an hour up to 2 hrs. The functionalized chips then were located separately on probe station connected to Agilent 34401A multimeter setup for measuring transient resistant over time. The multimeter was connected to a laptop for recording the data. Different samples of Gluten solutions with different concentration were studied and the transient sensors' resistant were recorded.

Experimental Results
Spectrophotometry:

The first test was to determine if an mAb could be covalently linked to a graphene-coated chip. To accomplish this, an HRP-conjugated antibody was linked to a graphene-coated chip which could be detected colorimetrically if bound. The test was positive, indicating that the HRP-labeled mAb was bound to the chip.

Figure 39:
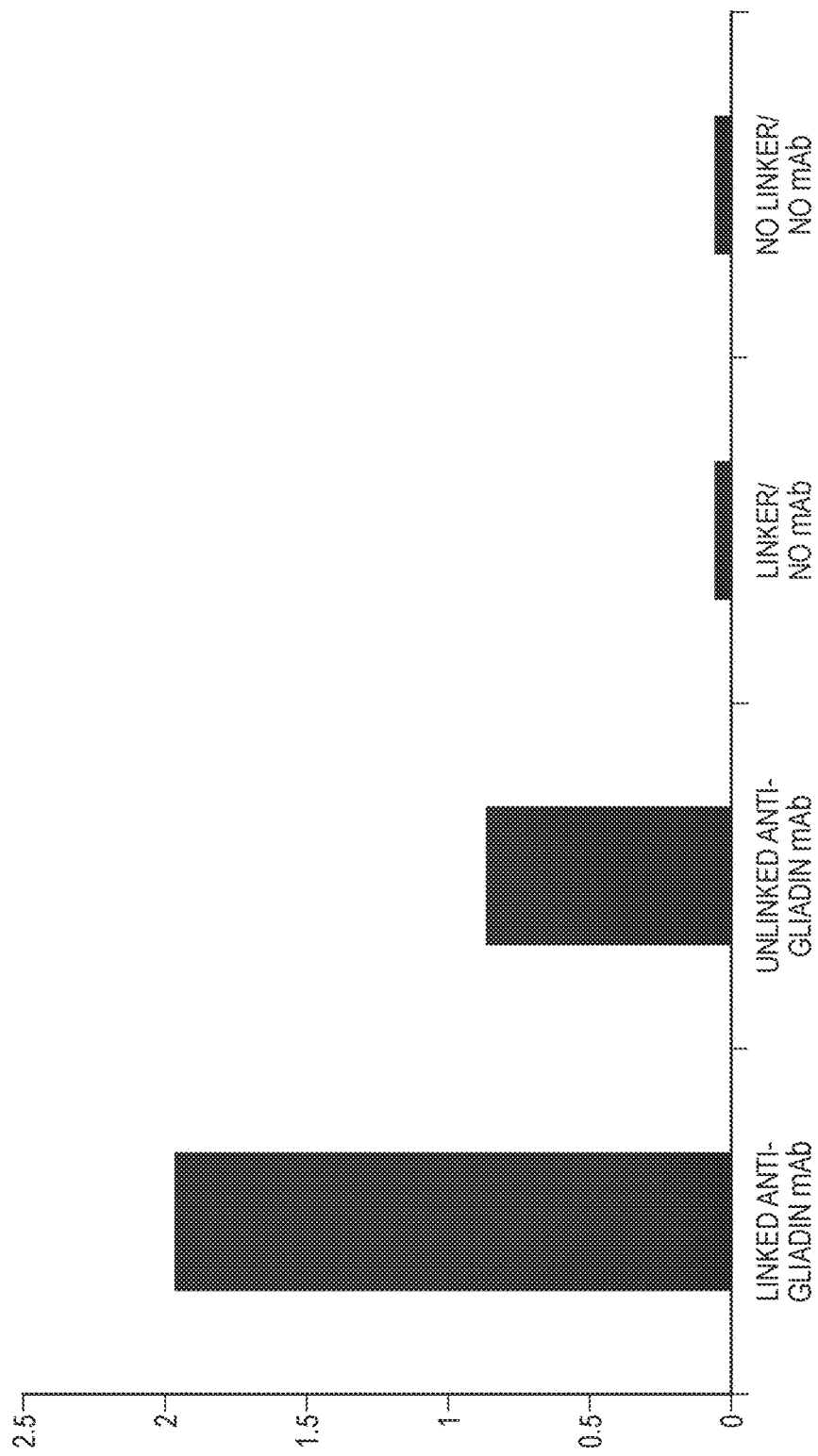
FIG. 39 shows some experimental results related to Anti-Gliadin mAb linkage to graphene-coated chips according to an embodiment.

Next experiment tried to demonstrate that the Abeam anti-gliadin mAb could be bound to a graphene-coated chip. Since the Abcam mAb is not labeled, but binds gliadin, the gliadin was conjugated to biotin so it could be detected by HRP-conjugated streptavidin (which binds specifically to biotin). So, the anti-gliadin mAb was linked covalently to the graphene-coated chips or just allowed to bind the chip without crosslinking. If the mAb was bound, it would bind the biotinylted gliadin, which in turn would bind the HRP-streptavidin and there would be a detectable color. The results are shown in FIG. 39, which shows some experimental results related to Anti-Gliadin mAb linkage to graphene-coated chips according to an embodiment. In the experiments, covalent linkage showed more intense color than simple adherence without linkage. Chips without antibody were negative in this study. One may conclude that mAb specifically recognizes the biotinylated-gliadin.

Figure 40A:
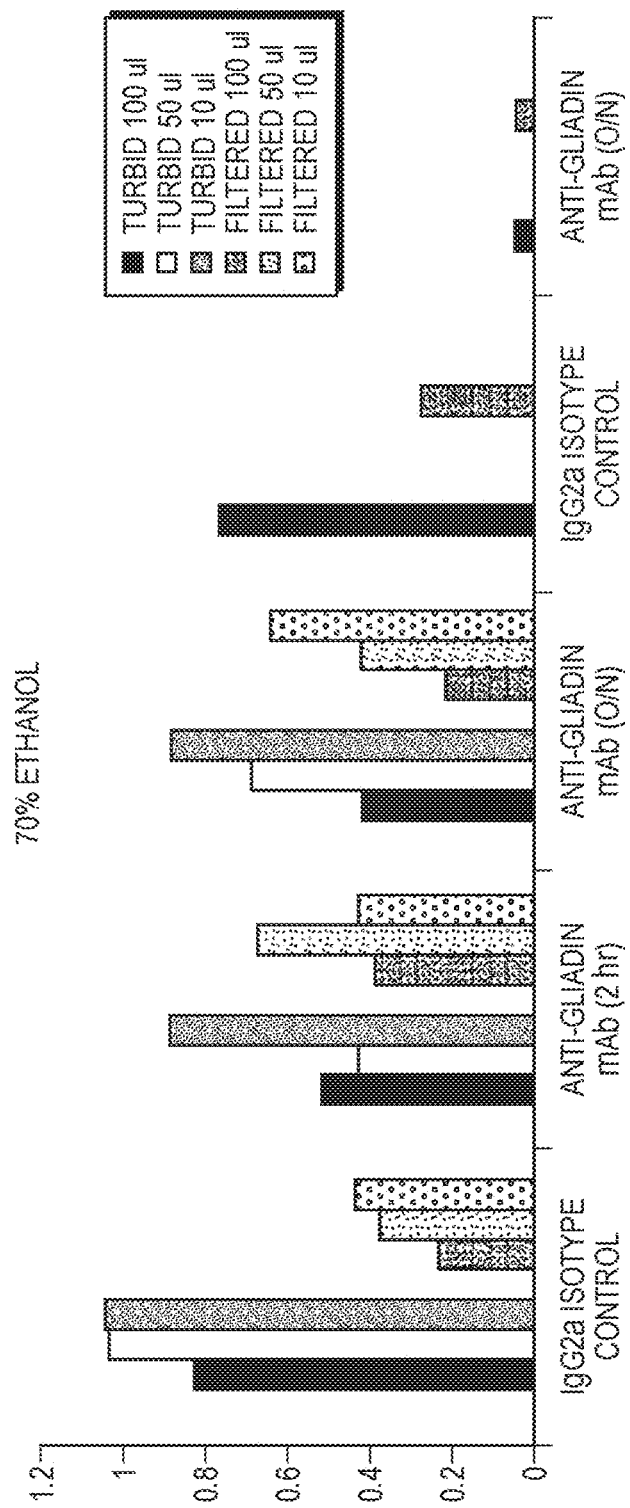
FIGS. 40A and 40B demonstrate effect of Biotinylated-Gliadin Binding at Different Concentrations of Ethanol according to an embodiment.
Figure 40B:
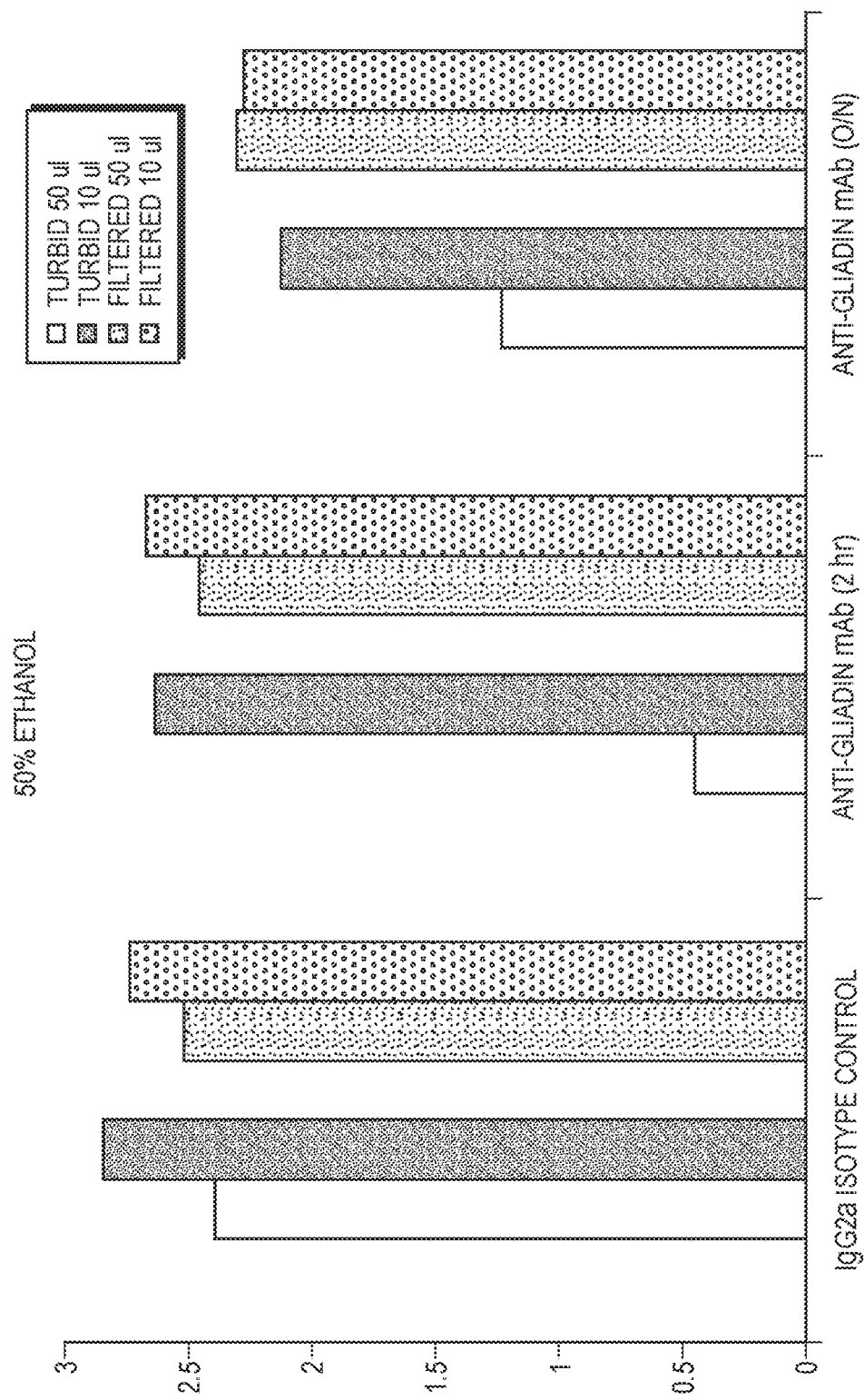

Next experiment attempted to study the effect of ethanol concentration on reaction, since the gliadin is extracted in ethanol. A challenge is that gliadin does not readily dissolve in ethanol. A 1 mg/ml solution was attemoted in 70% ethanol only to achieve a turbid suspension, even after sonication. Filtering removed the turbidity but also a significant amount of the gliadin. Anti-gliadin-bound ELISA plates were used for this test. The results are shown in FIGS. 40A and 40B, which demonstrate effect of Biotinylated-Gliadin Binding at Different Concentrations of Ethanol according to an embodiment. In this experiment, the turbid gliadin signal was stronger than the filtered gliadin in all cases tested. The mouse IgG2a isotype control did bind gliadin, but the turbid gliadin did stick to it, indicting a significant amount of non-specific binding was occurring. The amount of gliadin being used appears to be in vast excess. Also, 50% ethanol yielded a stronger signal than the 70% ethanol indicating it could be affecting the binding of gliadin to the antibody.

In order to determine whether ethanol was adversely affecting the results, a working concentration range for the gliadin was determined. The filtered biotinyated-gliadin solution was diluted from 1:10 using a dilution factor of 10 to home in on a usable decade range (FIGS. 41A, 41B) employing the mAb bound ELISA plates. FIGS. 41A and 41B illustrate results of determining a working gliadin concentration range according to one embodiment. The usable range was between 1:1000 and 1:100,000. This range was narrowed further to between 1:4000 and 1:8000. 1:5000 dilution was selected to be used going forward.

Figure 42A:
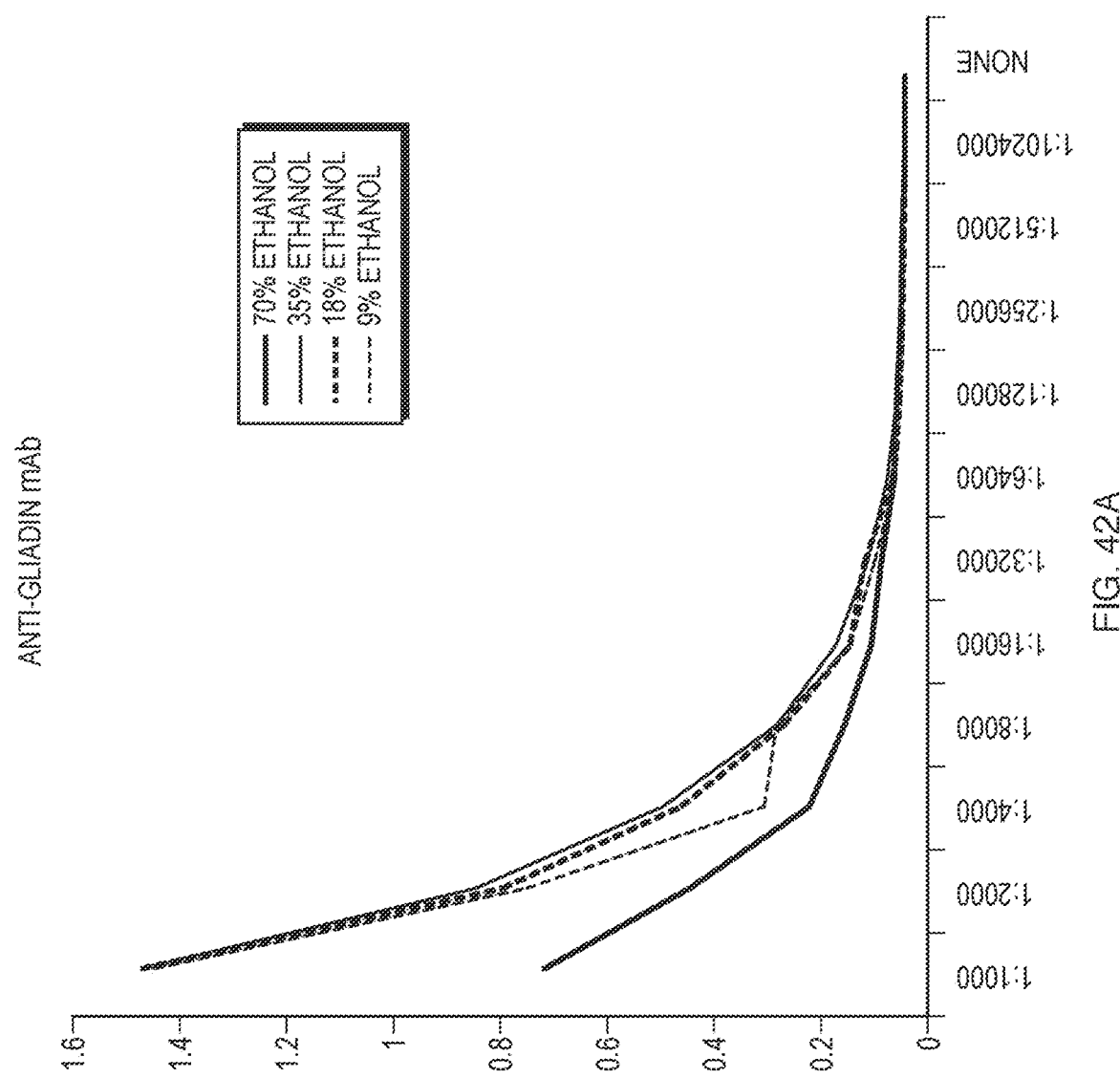
FIGS. 42A-B illustrate some effects of ethanol concentration on gliadin binding according to some embodiments.
Figure 42B:
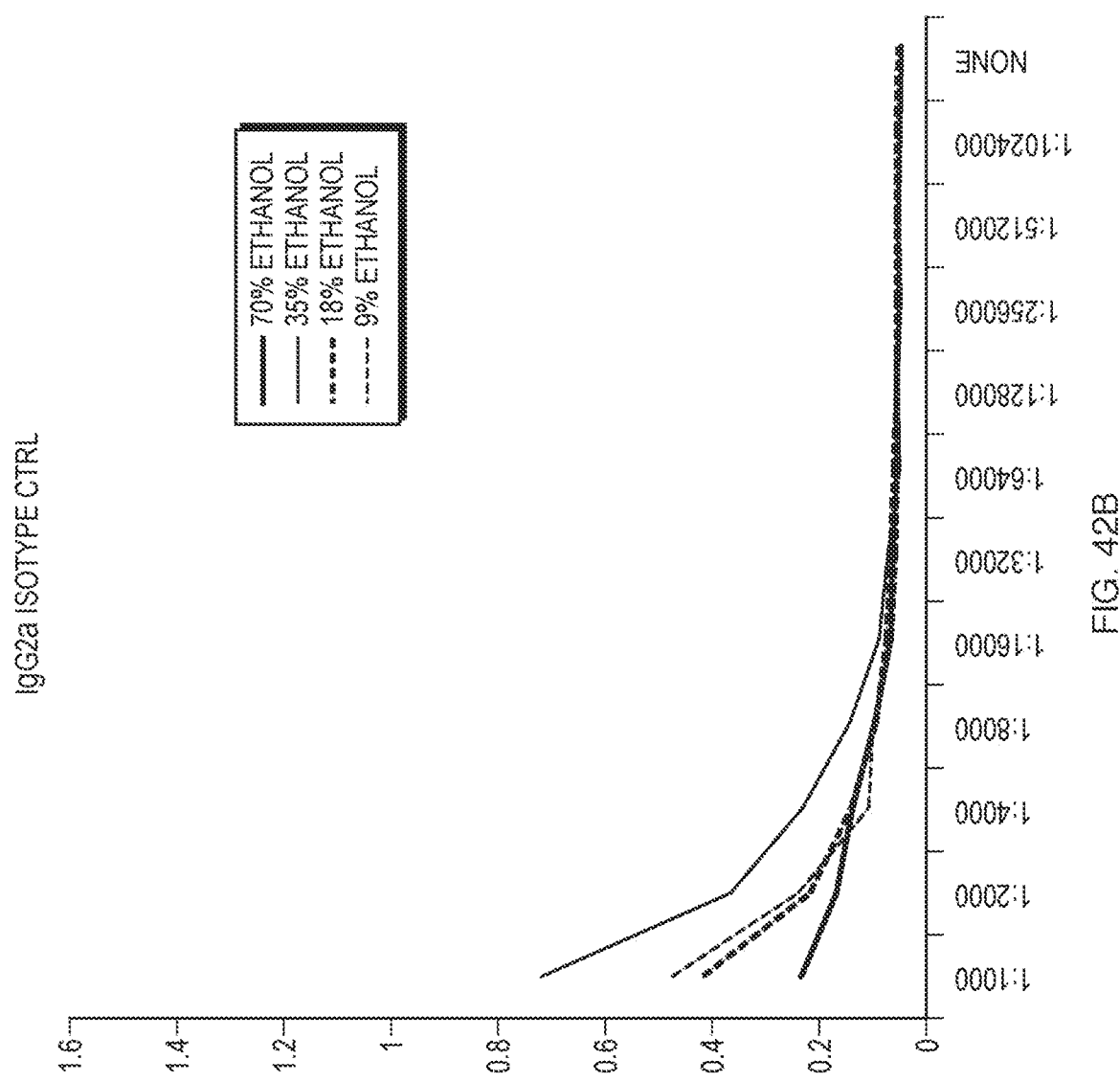
Figure 43A:
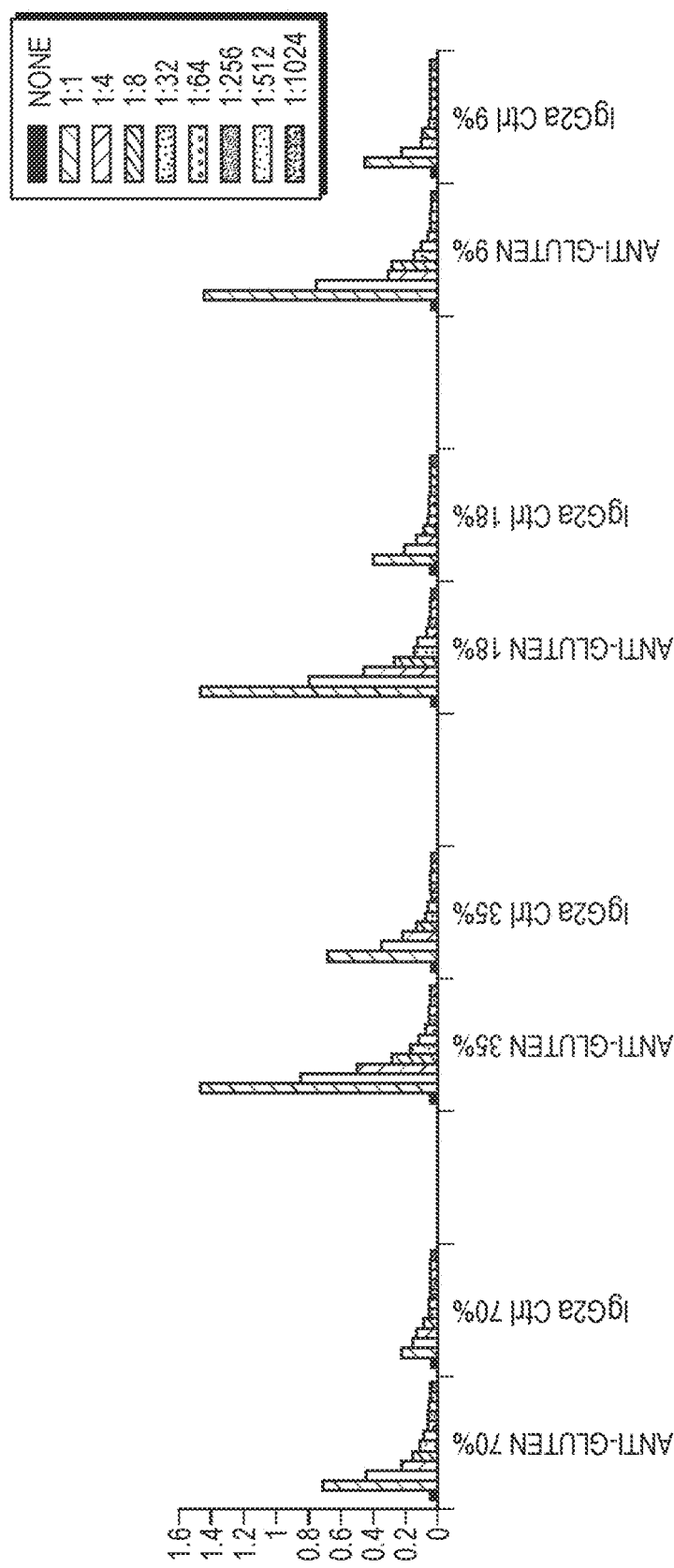

Then, the effect of ethanol concentration was examined in mAb bound ELISA plates. Biotinylated-gliadin was diluted at 1:5000 in different concentrations of ethanol (0%, 9%, 18%, 35% and 70%) (FIGS. 42A-B and 43A-B). FIGS. 42A-B illustrate some effects of ethanol concentration on gliadin binding according to some embodiments. 43A-B also illustrate some effects of ethanol concentration on gliadin binding from different perspectives according to some embodiments. In some cases, the assay does not work as well at 70% ethanol. 35% seems to provide acceptable results but there appear more non-specific binding on the isotype control mAb. In some embodiments, a suitable ethanol concentration is between 10%-20%.

Figure 44:
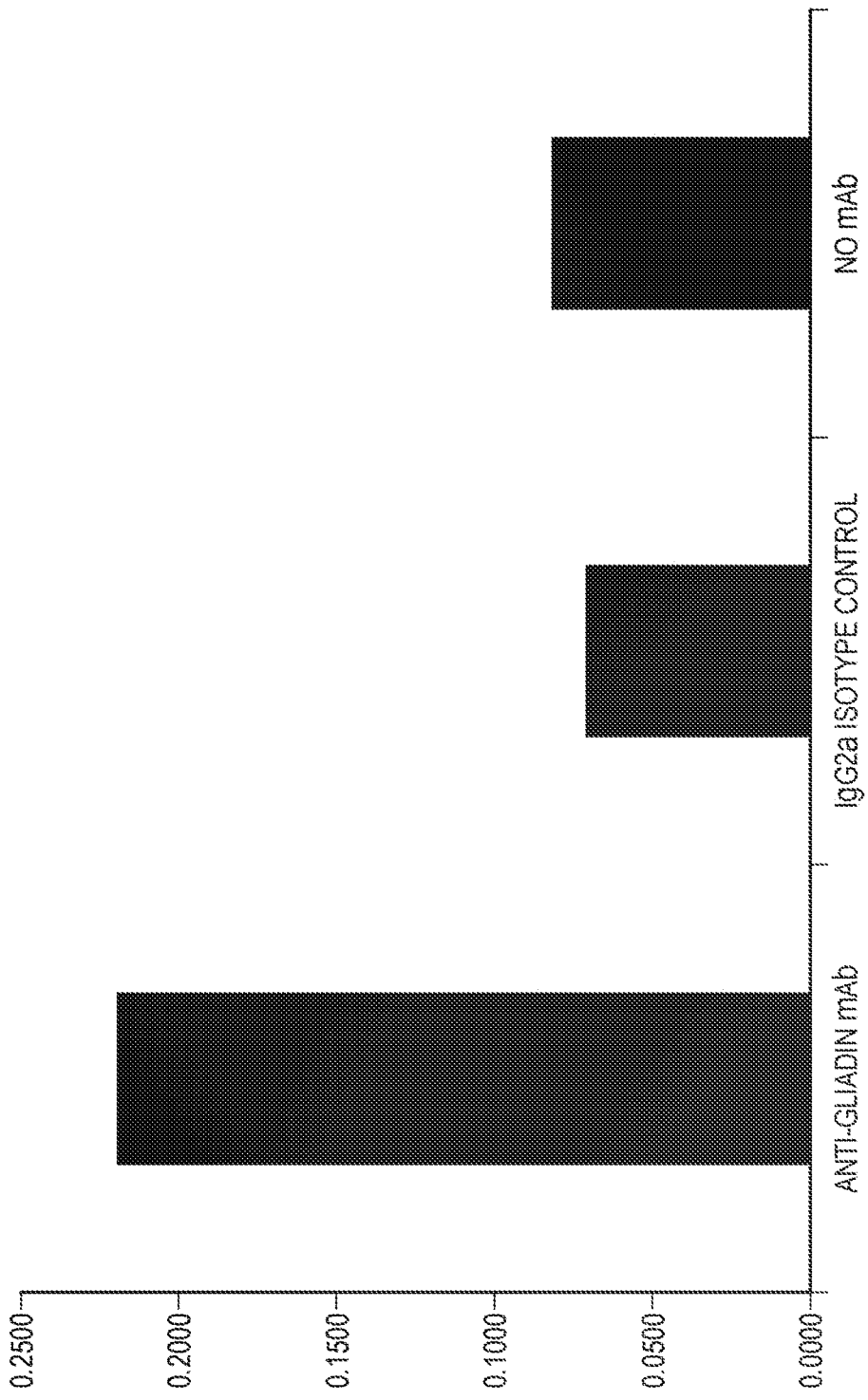
FIG. 44 shows results for proof of concept according to an embodiment.

Next experiments tried the protocol out on the graphene-coated chips using 15% ethanol with 1:5000 dilution of gliadin. FIG. 44 shows results for proof of concept according to an embodiment. More specifically, FIG. 44 shows the protocol with different the pieces assembled: anti-gliadin mAb covalently linked to graphene-coated chips, reacted with biotinylated-gliadin and detected with HRP-Streptavidin. In FIG. 44, the assay conditions were as follows: Antibody concentration: 3 ug/ml; Biotinylated-Gliadin dilution: 1:5000; Ethanol concentration: 15%; Streptavidin-HRP dilution: 1:5000; and Absorbance readout: 450 nm. The test was successful and specific. The final step to show proof of concept should be testing whether unlabeled gliadin can be detected binding to the graphene-coated chips with linked anti-gliadin mAb.

Figure 45A:
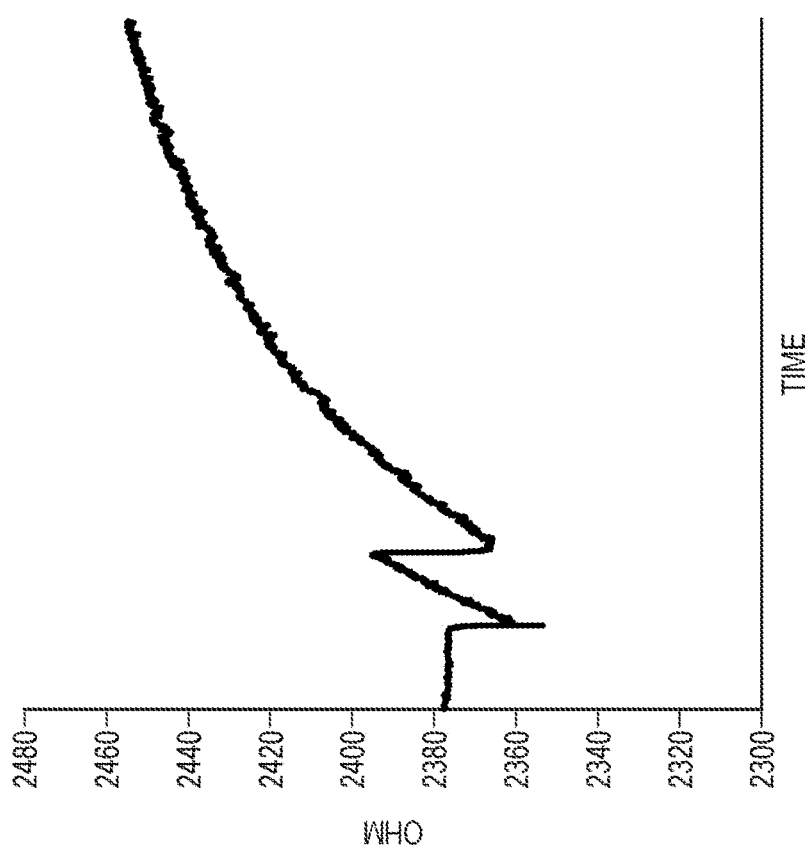
FIGS. 45A-B show ohmic measurements for, respectively, a naked graphene sensor and a graphene sensor functionalized by anti-gluten antibody, according to an embodiment.
Figure 45B:
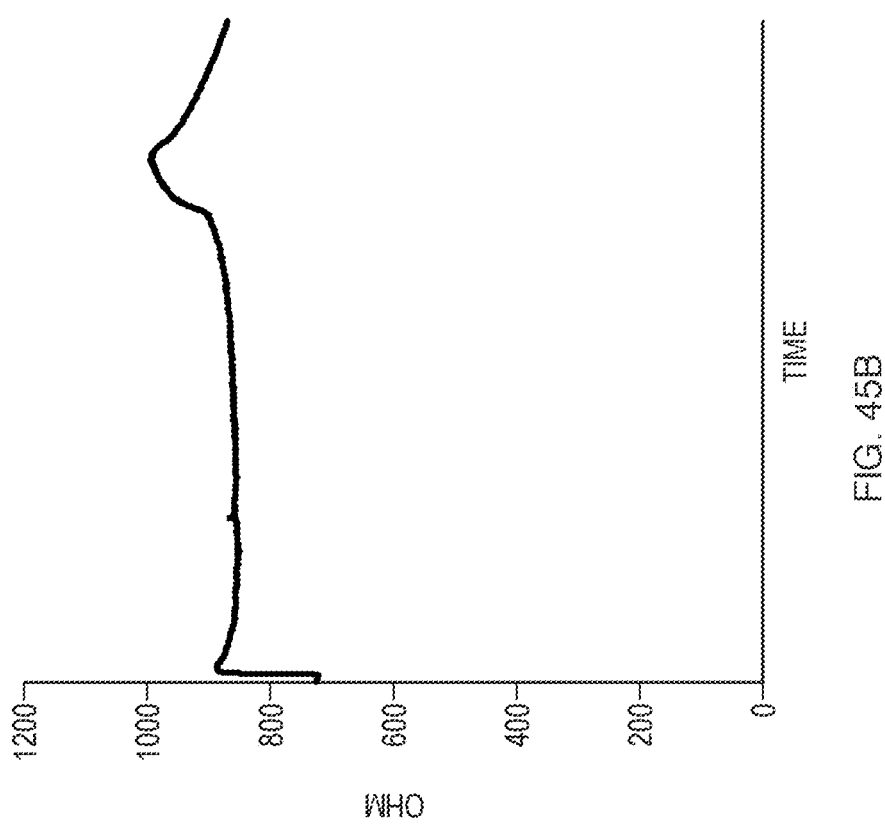

Galvanometric Measurements:

Some experiments studied effect of anti-gliadin antibody on signal enhancement. The studies compared the results of high concentrated gluten solutions on two sensor chip with functionalized antibody and untreated one. Some of the experimental results are shown in FIGS. 45A-48D FIGS. 45A-B show the distinguished pattern between the treated graphene and untreated one according to one embodiment. More specifically, FIG. 45A shows the results for naked graphene sensor, while FIG. 45B shows the results for a graphene sensor functionalized by anti-gluten antibody. For untreated graphene, the signal of resistance is similar to a ramp shape that gradually increases. For the treated surface, on the other hand, the signal change has a form that resembles a step function. The results indicate enhancing effect of gluten detection by functionalizing the graphene with antibody.

Figure 46A:
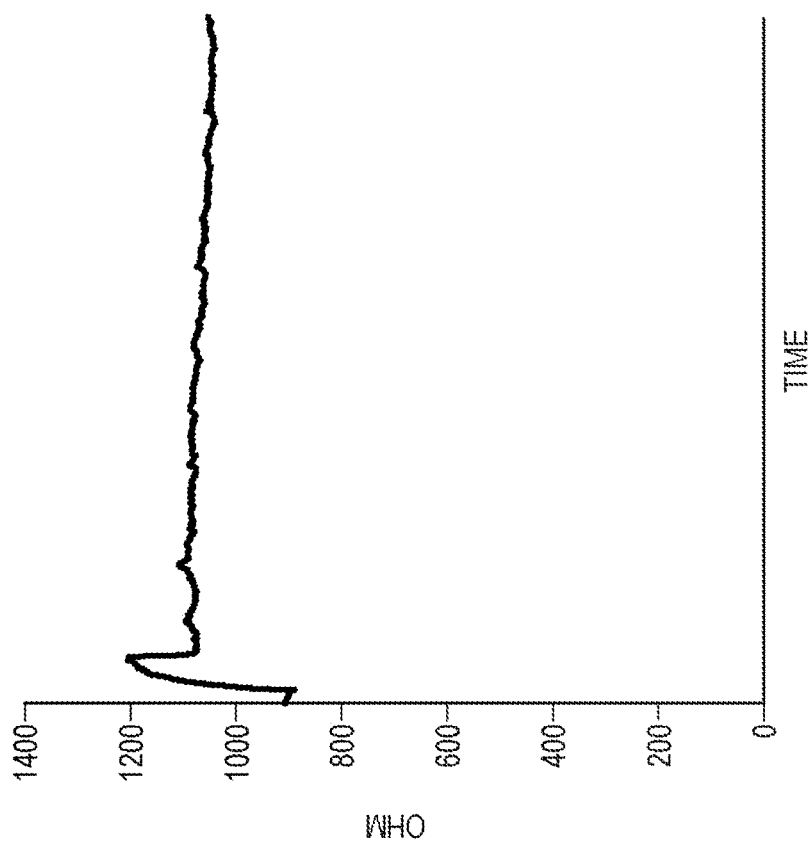
FIGS. 46A-B show ohmic measurements for sensors functionalized with anti-gliadin antibody and those functionalized with mouse monoclonal IgG antibody, according to an embodiment.
Figure 46B:
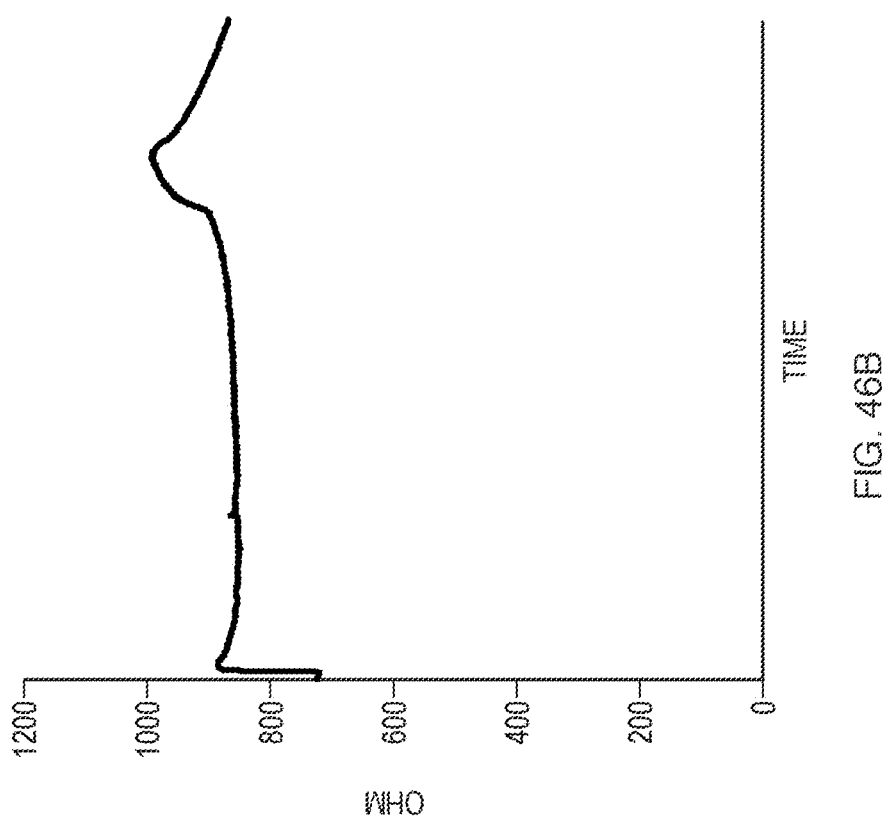

Further experiments showed the consistency of patterns in both cases and according to some embodiments. FIGS. 46A-B, for example, compare the results for sensors functionalized with anti-gliadin antibody and those functionalized with mouse monoclonal IgG antibody, according to one embodiment. More specifically, FIG. 46A shows sensor behavior functionalized by mouse IgG control antibody, and exposed to high dosage of Gluten. FIG. 46B, on the other hand, is similar to FIG. 45B and shows sensor behavior functionalized by anti-Gluten antibody and exposed to high dosage of Gluten. FIGS. 46A-B show a pattern of resistance change that is similar to the one discussed above, in exposure to high dosage of gluten in alcohol samples. One different is that, according to these results, when using anti-gliadin antibody, the signal is about 10% stronger than the other cases.

Further studies showed that solutions without gliadin content have different resistant pattern as compared to those with the gliadin solutions. FIG. 47A shows ohmic behavior of a sensor functionalized by anti-Gluten antibody, and exposed to none-Gluten solution according to an embodiment. FIG. 47B, on the other hand, shows ohmic behavior of a sensor covered with Tween 20 and exposed high dosage of Gluten according to an embodiment. FIGS. 47A and 47B indicate distinct patterns in the two cases.

As seen in FIG. 47B, some embodiments studied the effect of Tween20 to passivate the graphene surface, by treating the surface area of the sensor with Tween 20 only and without functionalizing it by any type of antibodies. The resistant measurements showed no changes in sensor resistance in experimental time when the sensor was exposed to the gliadin solution sample.

Figure 48B:
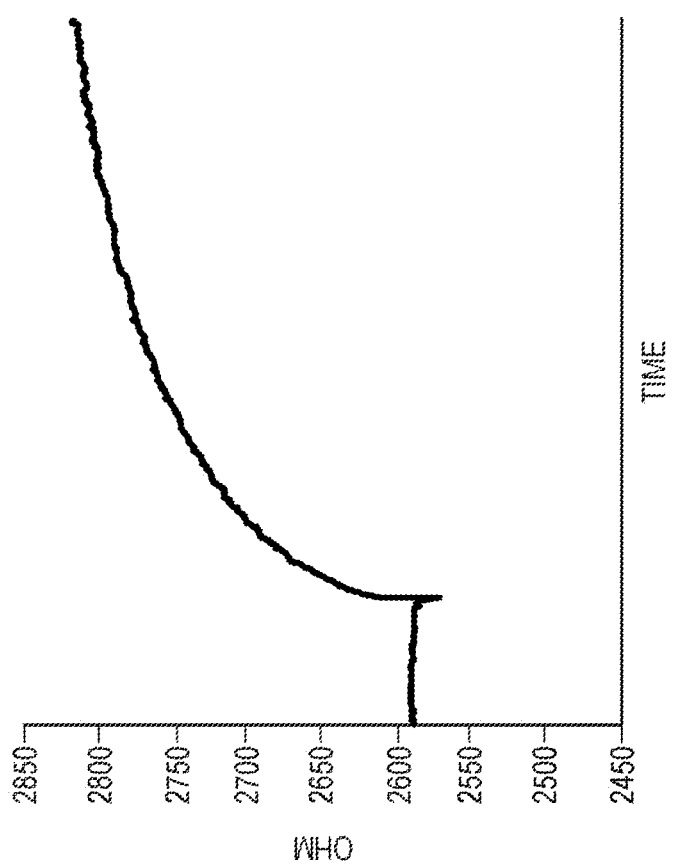
FIG. 48B shows the ohmic behavior of a sensor functionalized by mouse IgG control antibody, exposed to concentrated gluten-alcohol solution according to an embodiment.
Figure 48C:
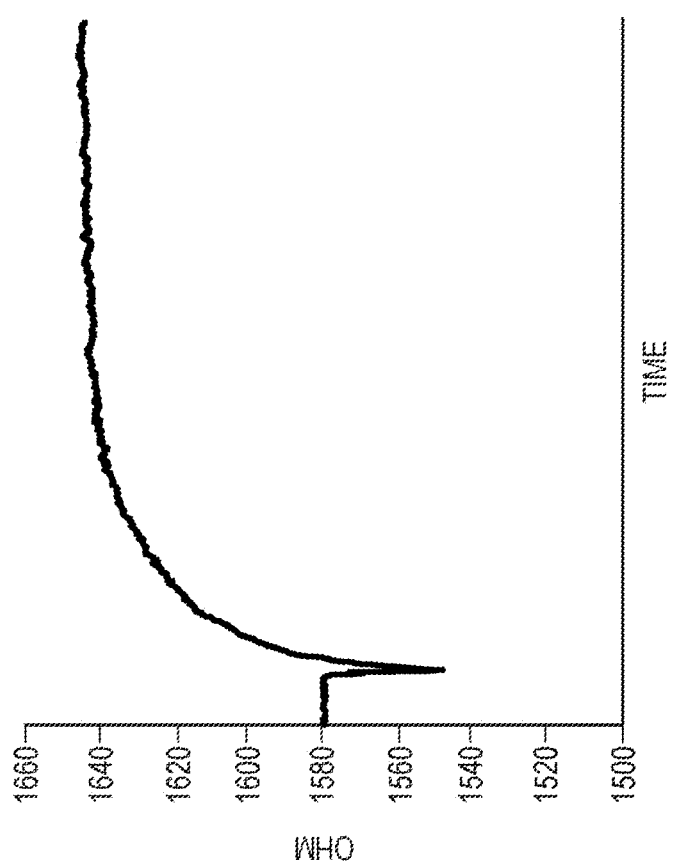
FIG. 48C shows the ohmic behavior of a sensor functionalized by anti-Gluten antibody, exposed to diluted gluten-alcohol solution according to an embodiment.
Figure 48D:
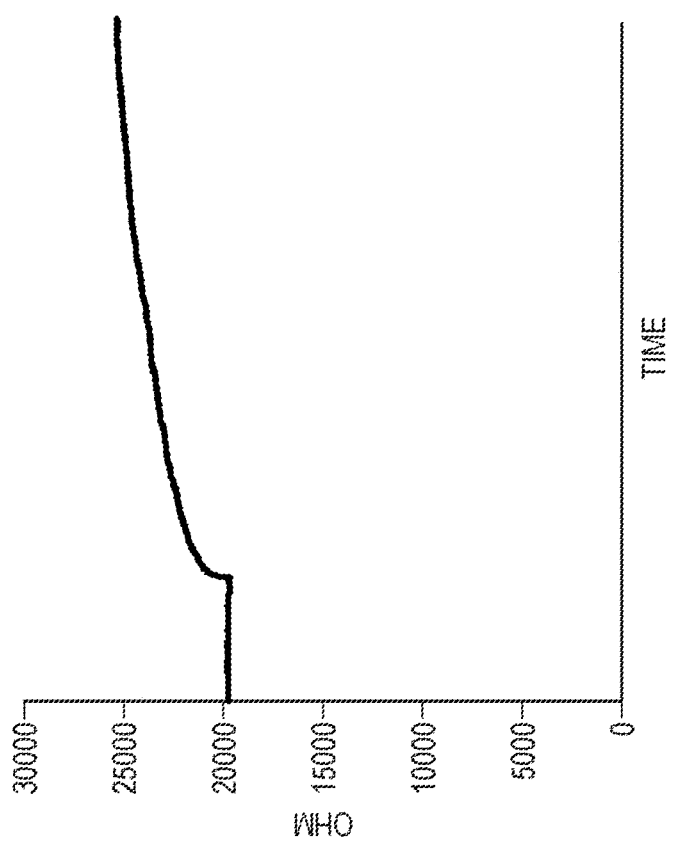
FIG. 48D shows the ohmic behavior of a sensor functionalized by anti-Gluten antibody, exposed to concentrated gluten-alcohol solution according to an embodiment.

FIG. 48A-D show results of experiments that studied the effect of gliadin concentration on functionality of the antibody in the sensor according to an embodiment. More specifically, FIG. 48A shows the ohmic behavior of a sensor functionalized by mouse IgG control antibody, exposed to diluted gluten-alcohol solution; FIG. 48B shows the ohmic behavior of a sensor functionalized by mouse IgG control antibody, exposed to concentrated gluten-alcohol solution; FIG. 48C shows the ohmic behavior of a sensor functionalized by anti-Gluten antibody, exposed to diluted gluten-alcohol solution; and FIG. 48D shows the ohmic behavior of a sensor functionalized by anti-Gluten antibody, exposed to concentrated gluten-alcohol solution. In these experiments, two concentration of gliadin protein in alcohol were chosen for this study. The concentration effects then were studied on the graphene surfaces functionalized with anti-gliadin antibody and also with mouse IgG antibody as the control. The results showed the same electrical resistance pattern for both substrates when they were exposed to high dosage of antibodies.

On the other hand in a much diluted concentrations only anti-gliadin antibodies were responsible to enhance the signal. This study showed that the Abcam anti-Gliadin antibodies are able to attached to graphene substrate through the linkers and keep their functionality. Also studies showed functionalizing the graphene with antibody can enhance the signal capturing and also enhance detection of low concentration of gliadin proteins in the samples.

In some embodiments, a sensor according to the present teachings can include a reference electrode that is positioned in vicinity of an antibody-functionalized graphene layer to which an AC voltage can be applied for establishing a time-varying electric field at the surface and/or in the vicinity of the antibody-functionalized graphene layer.

Figure 49:
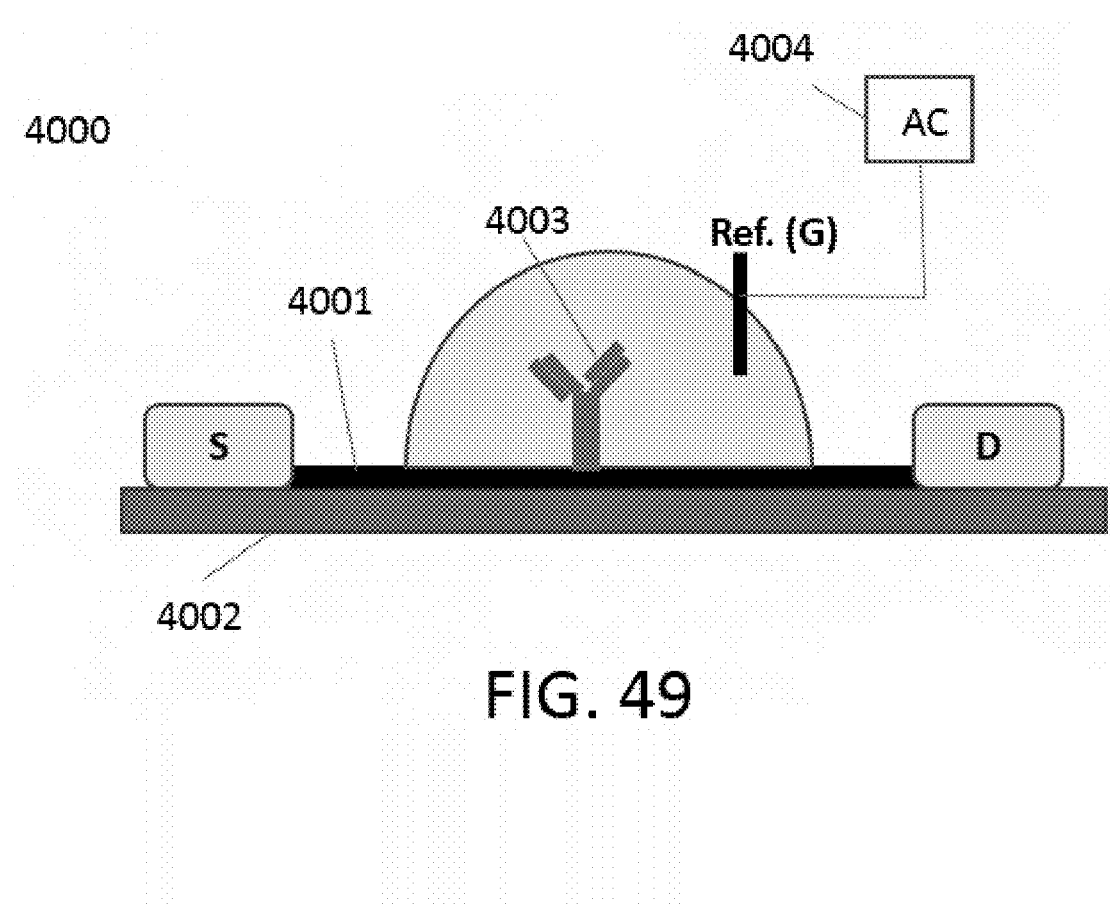
FIG. 49 schematically depicts a sensor according to an embodiment of the present teachings, which includes an antibody-functionalized graphene layer and a reference electrode positioned in proximity of the graphene layer.

By way of example, FIG. 49 schematically depicts another embodiment of a sensor 4000 according to the present teachings, which includes a graphene layer 4001 that is disposed on an underlying substrate 4002, e.g., a semiconductor substrate, and is functionalized with an antibody of interest 4003. The antibody 4003 can be selected to exhibit specific binding to an antigen of interest. Although in many embodiments, the antigen is a gluten protein, in other embodiments, the antigen can be other allergens. Further, in some embodiments, the antigen can be a pathogen, such as a bacterium and/or a virus, or a biomarker.

A source electrode (S) and a drain electrode (D) are electrically coupled to the graphene layer to allow measuring a change in one or more electrical parameters of the functionalized graphene layer in response to interaction of the functionalized graphene layer with a sample. The sensor 4000 further includes a reference electrode (G) that is disposed in proximity of the graphene layer.

In use, in some embodiments, a change in the electrical resistance of the functionalized graphene layer can be measured in response to the interaction of the functionalized graphene layer with a sample to identify and optionally quantify an analyte of interest, e.g., a gluten protein, in the sample. For example, when the sample includes an analyte that specifically binds to the antibody 4003, the interaction of the antibody with the analyte can modulate the electrical resistance of the graphene layer. A measurement of such a modulation of the electrical resistance of the graphene layer can be employed to identify that analyte in a sample under study.

It has been discovered that the application of an AC (alternating current) voltage via an AC voltage source 4004 to the graphene layer can facilitate the detection of one or more electrical properties of the functionalized graphene layer, e.g., a change in its resistance in response to the interaction of the antibody with an analyte exhibiting specific binding to the antibody. In particular, it has been discovered that the application of an AC voltage having a frequency in a range of about 1 kHz to about 1 MHz, e.g., in a range of about 10 kHz to about 500 kHz or in a range of about 20 kHz to about 100 kHz or in a range of about 30 kHz to about 60 kHz or in a range of about 100 kHz to about 200 kHz or in a range of about 200 kHz to about 300 kHz or in a range of about 400 kHz to about 500 kHz, can be especially advantageous in this regard. By way of example, the amplitude of the AC voltage applied to the reference electrode can be in a range of about 1 millivolt to about 3 volts, e.g., 0.5 volts to 1 volt. Further, in some cases, the voltage applied to the reference electrode can have an AC component and a DC offset, where the DC offset can be in a range of about −40 volts to about +40 volts, e.g., −1 volt to about +1 volt.

Without being limited to any particular theory, in some embodiments, it is expected that the application of a such a voltage to the reference electrode can minimize, and preferably eliminate, an effective capacitance associated with a sample, e.g., a liquid sample, with which the functionalized graphene layer is brought into contact as the sample is tested, thereby facilitating the detection of a change in the resistance of the underlying graphene layer in response to the interaction of the antibodies 4003 with a respective antigen. In some cases, the effective capacitance of the sample can be due to ions present in the sample.

F. CONCLUSION

In this disclosure the following qualifications apply, unless stated otherwise or deducted otherwise from the context. The terms "include," "comprise," "contain," and "have," when used after a set or a system, mean an open inclusion and do not exclude addition of other, non-enumerated, members to the set or to the system. Further, the conjunction "or" is used not exclusively but inclusively to mean and/or. Moreover, a subset of a set may include one or more than one, including all, members of the set. Also, the qualifier "some" may refer to a subset of a set that, therefore, may sometimes include all members of the set.

The foregoing description of the embodiments has been presented for purposes of illustration only. It is not exhaustive and does not limit the embodiments to the precise form disclosed. Those skilled in the art will appreciate from the foregoing description that modifications and variations are possible in light of the above teachings or may be acquired from practicing the embodiments. For example, the described steps need not be performed in the same sequence discussed or with the same degree of separation. Likewise various steps may be omitted, repeated, combined, or performed in parallel, as necessary, to achieve the same or similar objectives. Similarly, the described systems need not necessarily include all parts described in the embodiments, or may include multiple number of the described parts or other parts that are not described. Moreover, some parts of a system may perform tasks that are here described as being performed by one or more other parts. Accordingly, the embodiments are not limited to the above-described details, but instead are defined by the appended claims in light of their full scope of equivalents.

The invention claimed is:

1. A system for detecting an analyte in a sample, comprising:
 a processor,
 a sensor, comprising:
  a graphene layer,
  a plurality of antibodies coupled to said graphene layer to form an antibody-functionalized graphene layer, said antibodies exhibiting specific binding to said analyte,
  a reference electrode disposed in vicinity of said graphene layer,
  a plurality of electrical conductors electrically coupled to said graphene layer for measuring an electrical property of said graphene layer in response to an interaction of said sample with the graphene layer,
 said system further comprising an AC voltage source configured for electrically coupling to said reference electrode,
 wherein said processor is configured to control said AC voltage source to apply an AC voltage to said reference electrode so as to generate a time-varying electric field at or near a vicinity of said functionalized graphene layer.

2. The system of claim 1, wherein said AC voltage applied by said AC voltage source to said reference electrode has a frequency in a range of about 1 kHz to about 1 MHz.

3. The system of claim 2, wherein said applied AC voltage has an amplitude in a range of about 1 millivolt to about 3 volts.

4. The system of claim 1, wherein said analyte comprises an allergen.

5. The system of claim 4, wherein said analyte comprises a protein.

6. The system of claim 1, wherein said analyte comprises a gluten protein.

7. The system of claim 1, wherein said analyte comprises a pathogen.

8. The system of claim 7, wherein said pathogen comprises a bacterium.

9. The system of claim 7, wherein said pathogen comprises a virus.

10. The system of claim 1, wherein said reference electrode is positioned at a distance in a range of about 1 to about 2 mm above said graphene layer.

11. The system of claim 1, wherein said graphene layer is disposed on an underlying substrate.

12. The system of claim 11, wherein said underlying substrate comprises a semiconductor.

13. The system of claim 12, wherein said semiconductor comprises silicon.

14. The system of claim 11, wherein said underlying substrate comprises a plastic substrate.

15. The system of claim 1, wherein said analyte comprises a biomarker.

16. The system of claim 1, wherein said sensor comprises at least one port for receiving a sample.

17. The system of claim 16, wherein said sensor further comprises one or more microfluidic channels for directing the sample from said port to said functionalized graphene layer.

18. The system of claim 1, further comprising a passivation layer covering at least a portion of the graphene layer that is not functionalized by the plurality of antibodies.

19. The system of claim 18, wherein the passivation layer is configured to inhibit interaction of the analyte with the portion of the graphene layer that is not functionalized by the plurality of antibodies.

\* \* \* \* \*